US010799522B2

(12) United States Patent
Gelovani et al.

(10) Patent No.: US 10,799,522 B2
(45) Date of Patent: Oct. 13, 2020

(54) COMPOSITIONS AND METHODS RELATING TO GALECTIN DETECTION

(71) Applicant: Wayne State University, Detroit, MI (US)

(72) Inventors: Juri G. Gelovani, Detroit, MI (US); Nashaat Turkman, Wixom, MI (US); Vadim Popov, Detroit, MI (US); Robin Bonomi, Livonia, MI (US); Aleksandr Shavrin, Walled Lake, MI (US); Philip Alther, Walled Lake, MI (US); Andrei Borisov, Ann Arbor, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 15/747,649

(22) PCT Filed: Jul. 27, 2016

(86) PCT No.: PCT/US2016/044263
§ 371 (c)(1),
(2) Date: Jan. 25, 2018

(87) PCT Pub. No.: WO2017/019770
PCT Pub. Date: Feb. 2, 2017

(65) Prior Publication Data
US 2018/0221400 A1    Aug. 9, 2018

Related U.S. Application Data

(60) Provisional application No. 62/197,338, filed on Jul. 27, 2015.

(51) Int. Cl.
| | | |
|---|---|---|
| *A61K 31/70* | (2006.01) | |
| *G01N 33/58* | (2006.01) | |
| *A61K 31/7056* | (2006.01) | |
| *A61K 31/7016* | (2006.01) | |
| *G01N 33/60* | (2006.01) | |
| *G01N 33/68* | (2006.01) | |

(52) U.S. Cl.
CPC ...... *A61K 31/7056* (2013.01); *A61K 31/7016* (2013.01); *G01N 33/582* (2013.01); *G01N 33/60* (2013.01); *G01N 33/68* (2013.01); *G01N 2333/4724* (2013.01); *G01N 2800/7028* (2013.01)

(58) Field of Classification Search
CPC .............................. A61K 31/70; G01N 33/582
See application file for complete search history.

(56) References Cited

U.S. PATENT DOCUMENTS

2011/0130553 A1    6/2011   Nilsson

FOREIGN PATENT DOCUMENTS

| WO | WO-2012116196 A2 * | 8/2012 | ......... A61K 51/0491 |
|---|---|---|---|
| WO | WO-2014067986 A1 * | 5/2014 | ............. A61K 31/70 |
| WO | WO-2014078655 A1 | 5/2014 | |

OTHER PUBLICATIONS

Hanwen Zhang et al., Synthesis and evaluation of 18F-labeled benzylguanidine analogs for targeting the human norepinephrine transporter, Eur J Nucl Med Mol Imaging, 41, 322-332. (Year: 2014).*
Bacchi et al., Metabolism under hypoxia in Tm1 murine melanoma cells is affected by the presence of galectin-3, a metabolomics approach, SpringerPlus, 3:470, 2014.
De Oliveira, J. et al., Hypoxia up-Regulates Galectin-3 in Mammary Tumor Progression and Metastasis, PLoS One, 10(7):e0134458, Jul. 29, 2015.
Fernandez, A. et al., Expression of cathepsin D and galectin 3 in tubular carcinomas of the breast, AMPIS, 116(1):33-40, Jan. 2008.
Gallegos, I. et al., Expression of antigen tf and galectin-3 in fibroadenoma, BMC Research Notes, 5:694, 2012.
Ikemori, R. et al., Galectin-3 up-regulation in hypoxic and nutrient deprived microenvironments promotes cell survival, PLoS One, 9(11):e111592, Nov. 4, 2014.
Nangia-Makker, P. et al., Galectin-3 induces endothelial cell morphogenesis and angiogenesis, the American Journal of Pathology, 156(3):899-909, Mar. 2000.
Rego, M. et al., The glycomic profile of invasive ductal carcinoma of the breast is altered in patients with hypoxic regions: implications for tumor behavior, Folia histochemica et cytobiologica, Polish Academy of Sciences, Polish Histochemical and Cytochemical Society, 52(2):96-103, 2014.
Sarwat, A. et al., Expression of HIF-1, galectin-3, cox-2 and Wilms tumor-1 protein in multiple schwannomas of the conus medullaris, Journal of Neuro-Oncology, 92(1):111-5, Mar. 2009.
Selemetjev, S. et al., Changes in the expression pattern of apoptotic molecules (galectin-3, Bcl-2, Bax, survivin) during progression of thyroid malignancy and their clinical significance, Wiener klinische Wochenschrift, 127(9-10):337-44, May 2015.
Shekhar, M. et al., Interaction with endothelial cells is a prerequisite for branching ductal-alveolar morphogenesis and hyperplasia of preneoplastic human breast epithelial cells: regulation by estrogen, Cancer Res., 60(2):439-49, Jan. 15, 2000.

(Continued)

*Primary Examiner* — Michael G. Hartley
*Assistant Examiner* — Jagadishwar R Samala
(74) *Attorney, Agent, or Firm* — Julie K. Staple; Dinsmore & Shohl LLP

(57) ABSTRACT

Compositions and methods for detection and assessment of galectins are provided by the present invention, including labeled compositions, pharmaceutical composition including a labeled composition for galectin detection and a pharmaceutically acceptable carrier, method of aiding in diagnosis and/or treatment of a condition characterized by upregulation of one or more galectins in a subject in need thereof and precursor compositions for synthesis of chemical compositions, including but not limited to labeled compositions for detection and assessment of galectins.

20 Claims, 23 Drawing Sheets

(56) References Cited

OTHER PUBLICATIONS

Shekhar, M., Alterations in galectin-3 expression and distribution correlate with breast cancer progression: functional analysis of galectin-3 in breast epithelial-endothelial interactions, the America Journal of Pathology, 185(6):1931-41, Dec. 2004.

Zhang, H. et al., Galectin-3 as a marker and potential therapeutic target in breast cancer, PLoS One, 9(9):e103482, Sep. 2014.

Zhang, H. et al., Synthesis and Evaluation of [18F]Fluorine-labeled Benzylguanidine Analogs for Targeting the Human Norepinephrine Transporter, European Journal of Nuclear Medicine and Molecular imaging, 41(2): 322-332, Feb. 2014.

D'Alessandria, C. et al., Noninvasive in Vivo Imaging and Biologic Characterization of Thyroid Tumors by ImmunoPET Targeting of Galectin-3, *Cancer Research*, 76(12): 3583-3592, Jun. 15, 2016.

Chen, G. et al., Expression of galectin-3 and Sambucus nigra agglutinin and its clinicopathological significance in benign and malignant lesions of breast, Journal of Central South University Medical Sciences, 35(6): 584-9, Jun. 2010 (Abstract).

Mayoral, M. et al., Identification of galectin-3 and mucin-type O-glycans in breast cancer and its metastasis to brain, Cancer Invest., 26(6):615-23, Jul. 2008 (Abstract).

* cited by examiner

Scheme 1a

Scheme 1b

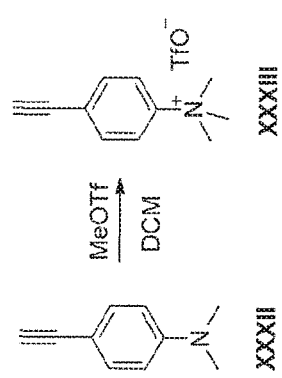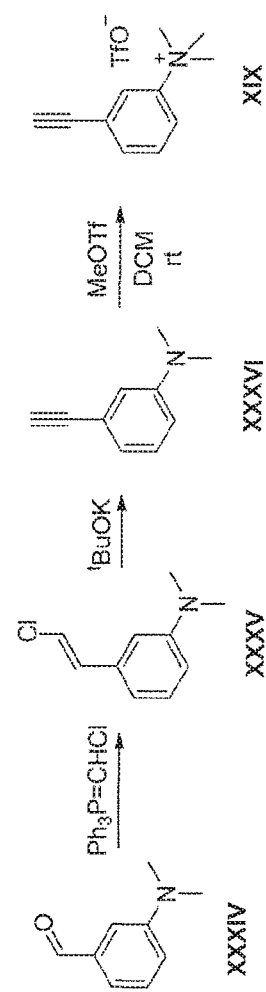
FIG. 3

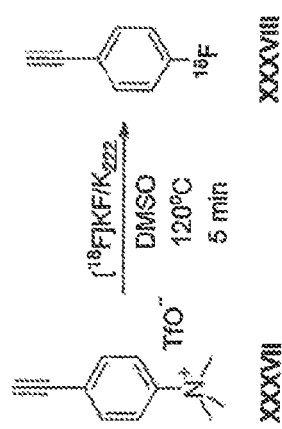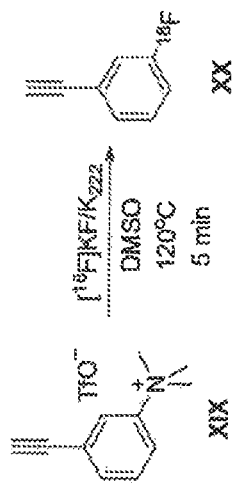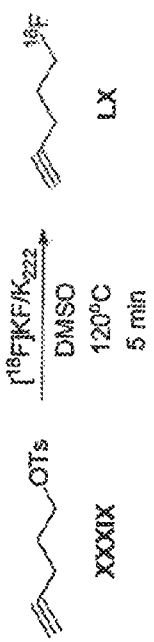
FIG. 4

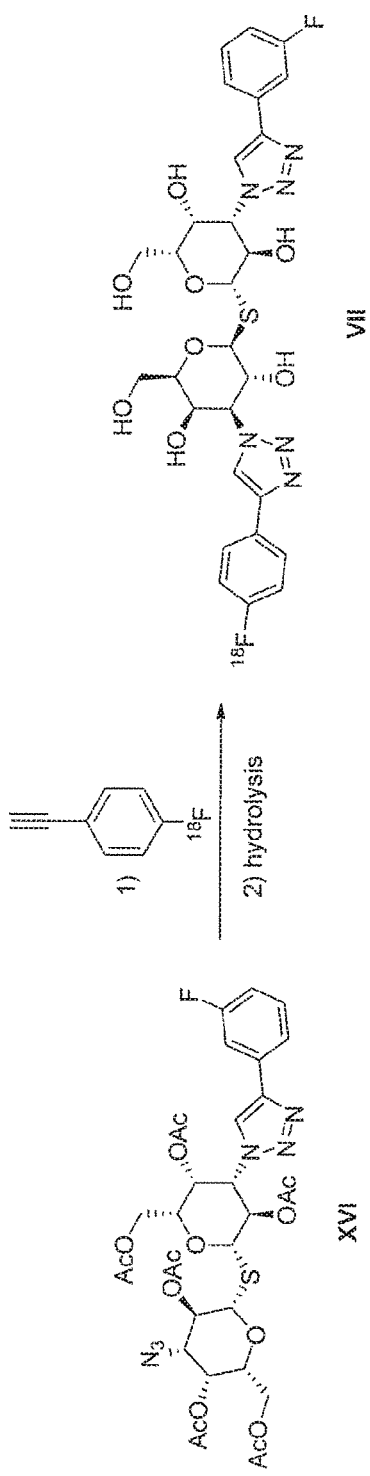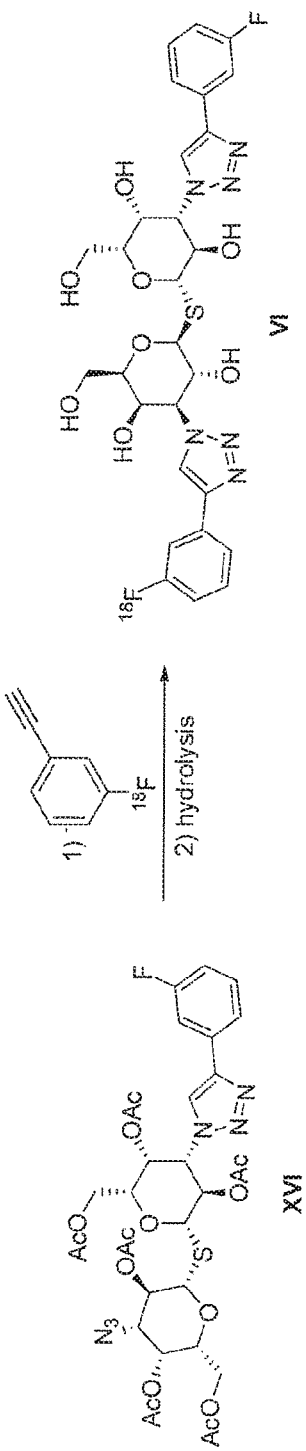
FIG. 5

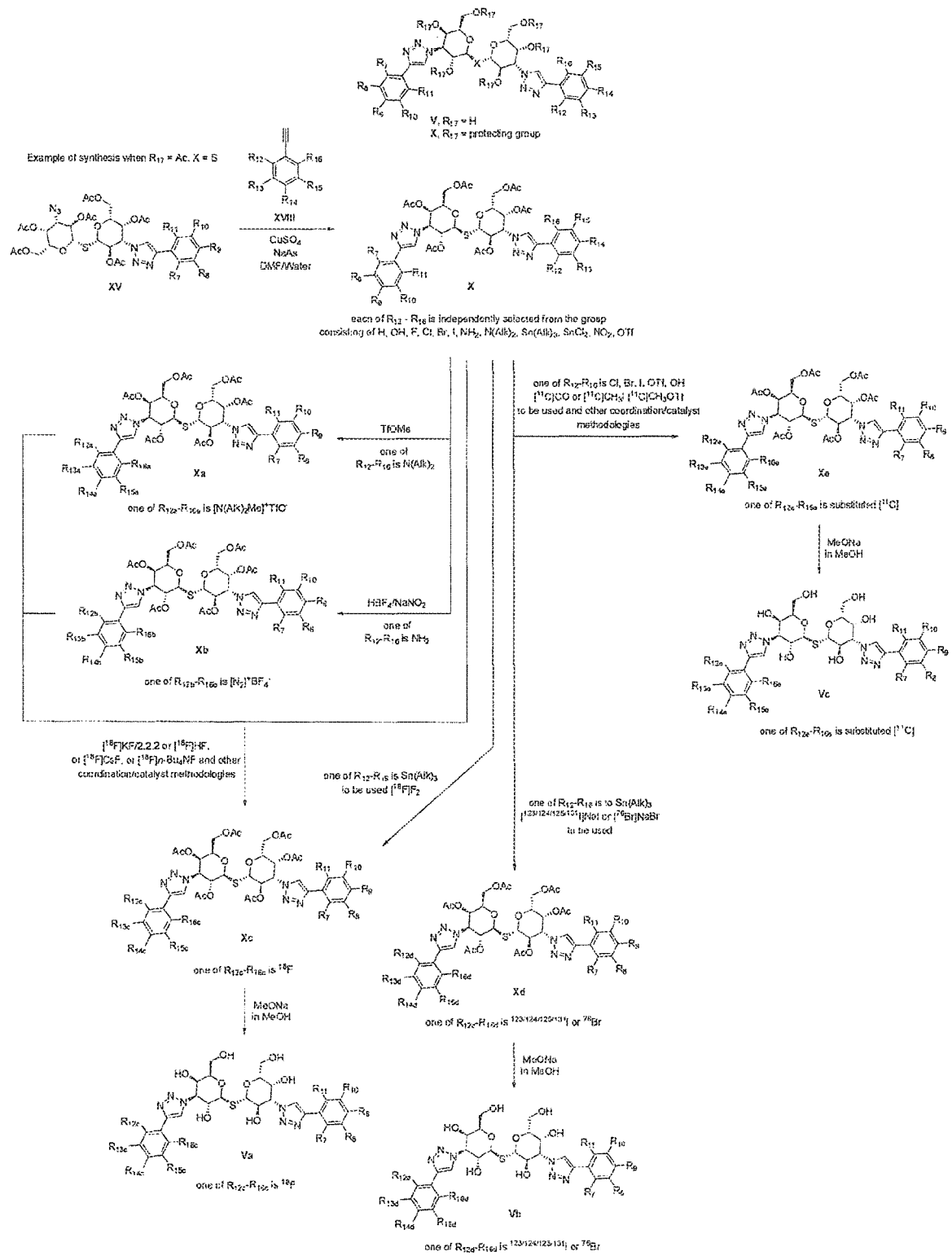
FIG. 7 Scheme 5: Synthesis of compounds of structural formula V and X, specifically shown in this figure as radiolabeled phenyltriazolothiodigalactosides.

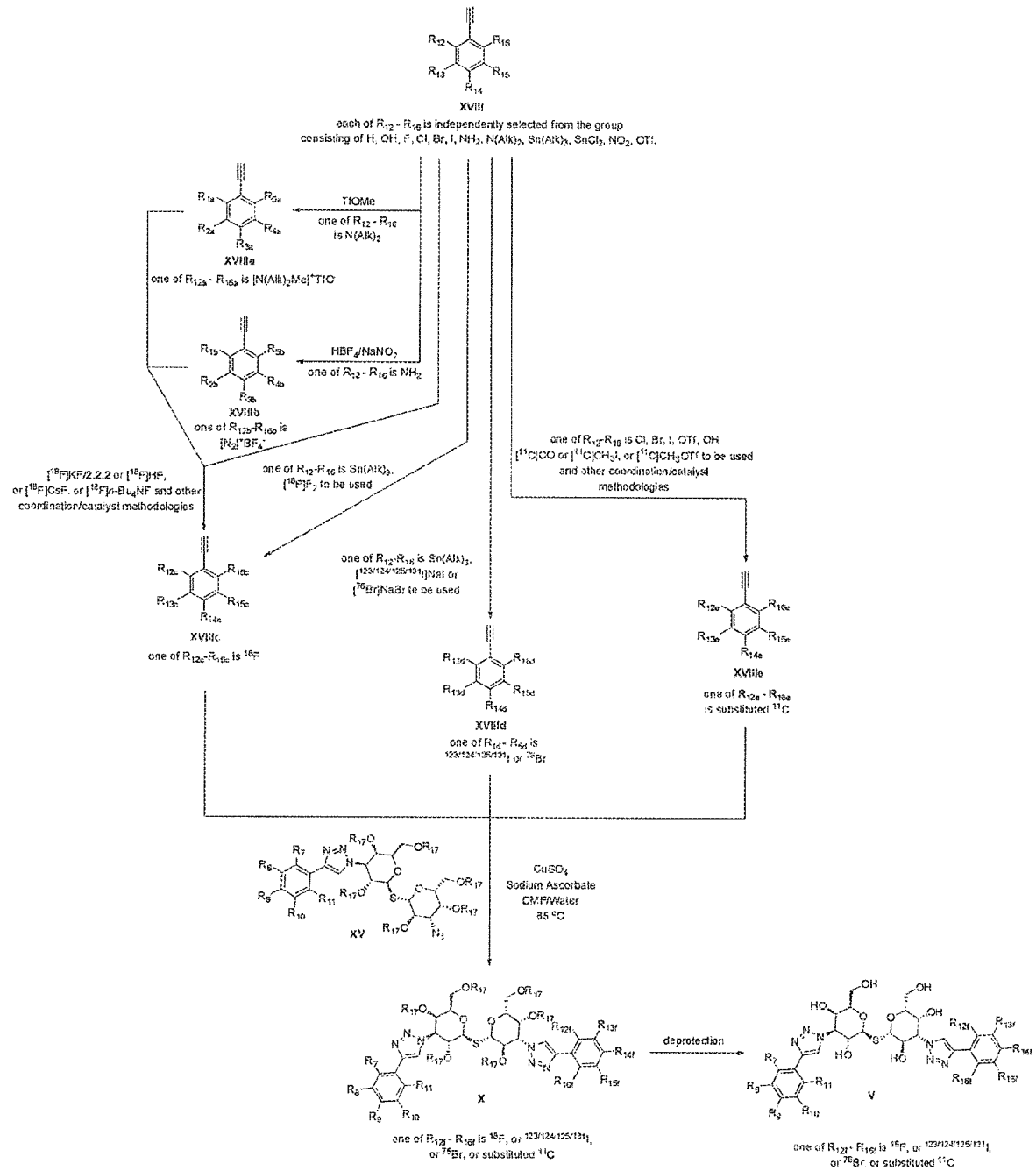
FIG. 8 Scheme 6: Synthesis of compounds of structural formula XVIII radiolabeled phenylacetylenes.

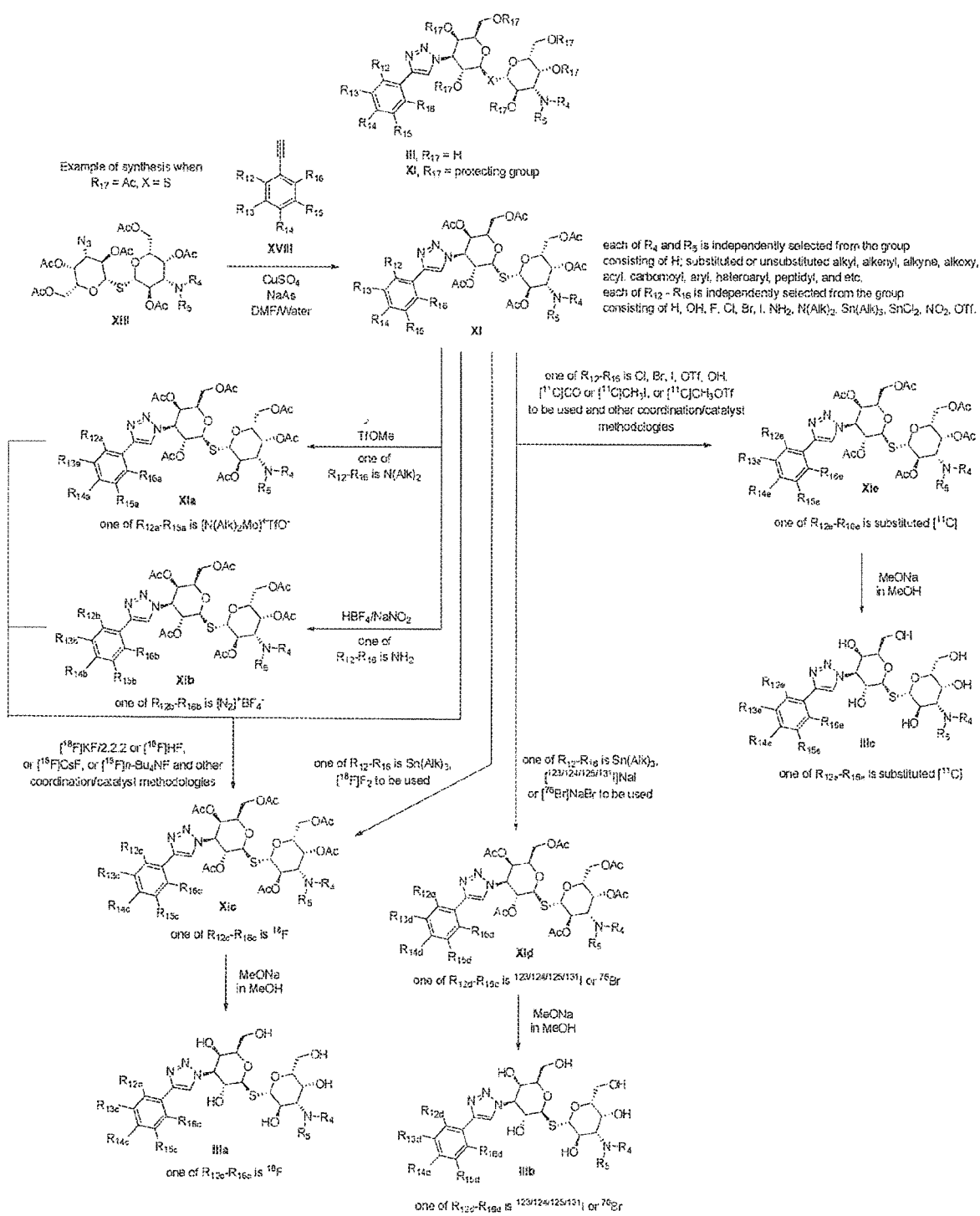
FIG. 9 Scheme 7: Synthesis of compounds of structural formula III and XI, specifically shown in this figure as radiolabeled thiodigalactosides.

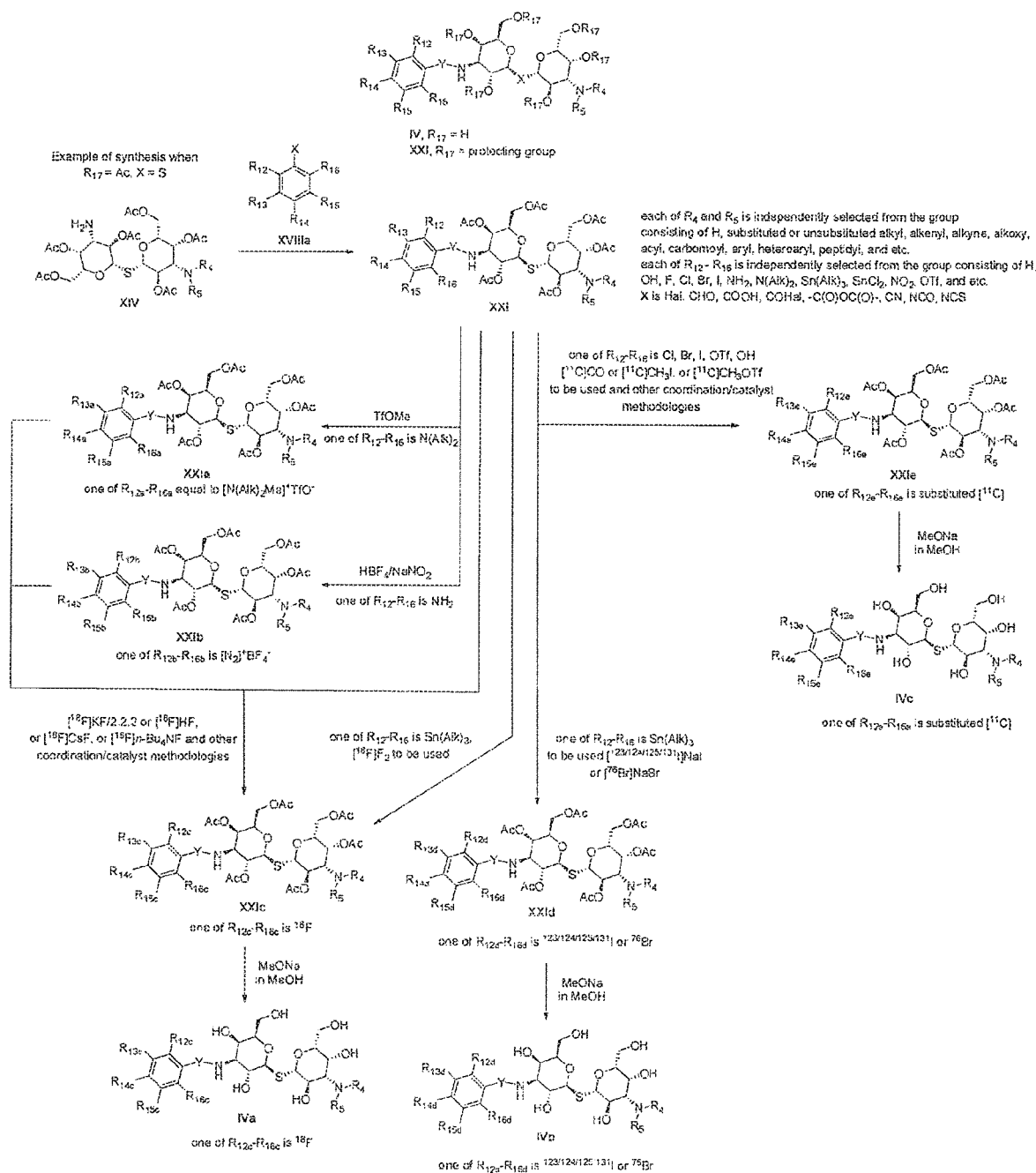
FIG. 10 Scheme 8: Synthesis of compounds of structural formula IV and XXI, specifically shown in this figure as radiolabeled aminothiodigalactosides.

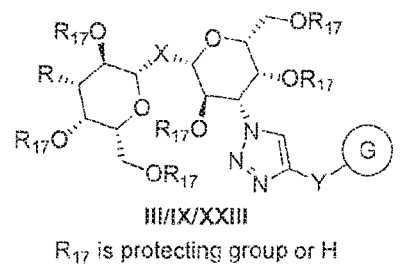

III/IX/XXIII
R$_{17}$ is protecting group or H

Example of synthesis when R$_{17}$ = Ac, X = S

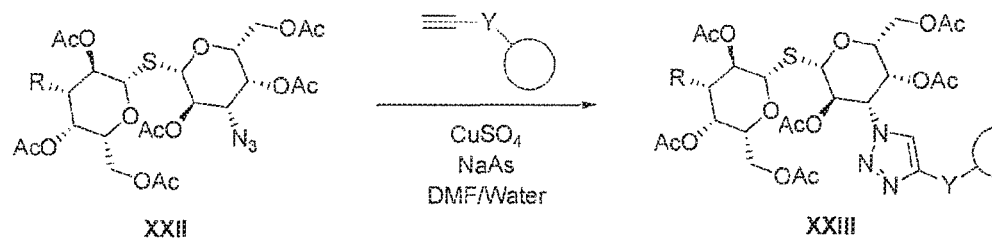

R$_3$ - R$_5$, Y is H; substituted or unsubstituted alkyl, alkenyl, alkyne, alkoxy, acyl, carbomoyl, aryl, heteroaryl, peptidyl, and etc. (Y is not equal to H)

◯ is chelator

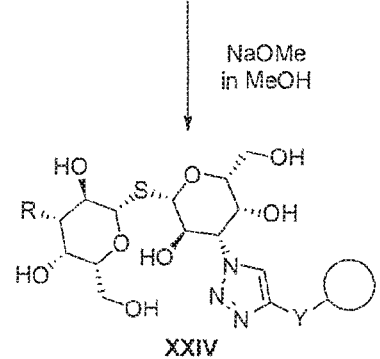

[$^m$G] = [$^{67/68}$Ga], [$^{89}$Zr], [$^{99m}$Tc], [$^{111}$In], [$^{61/62/64}$Cu], and etc.

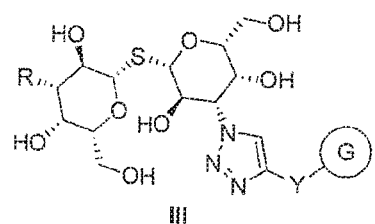

III

FIG. 11 Scheme 9: Synthesis of compounds of structural formula III, IX, XXIII, specifically shown in this figure as radiolabeled aminothiodigalactosides.

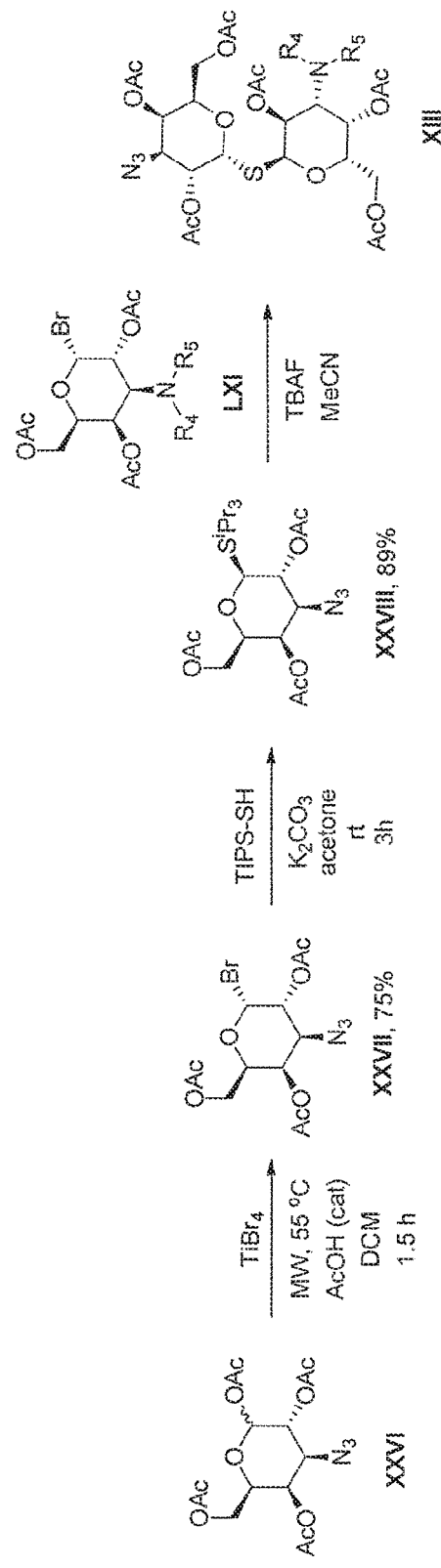
FIG. 12 Scheme 10: Synthesis of compounds of structural formula XIII, specifically shown in this figure as thiodigalactosides.

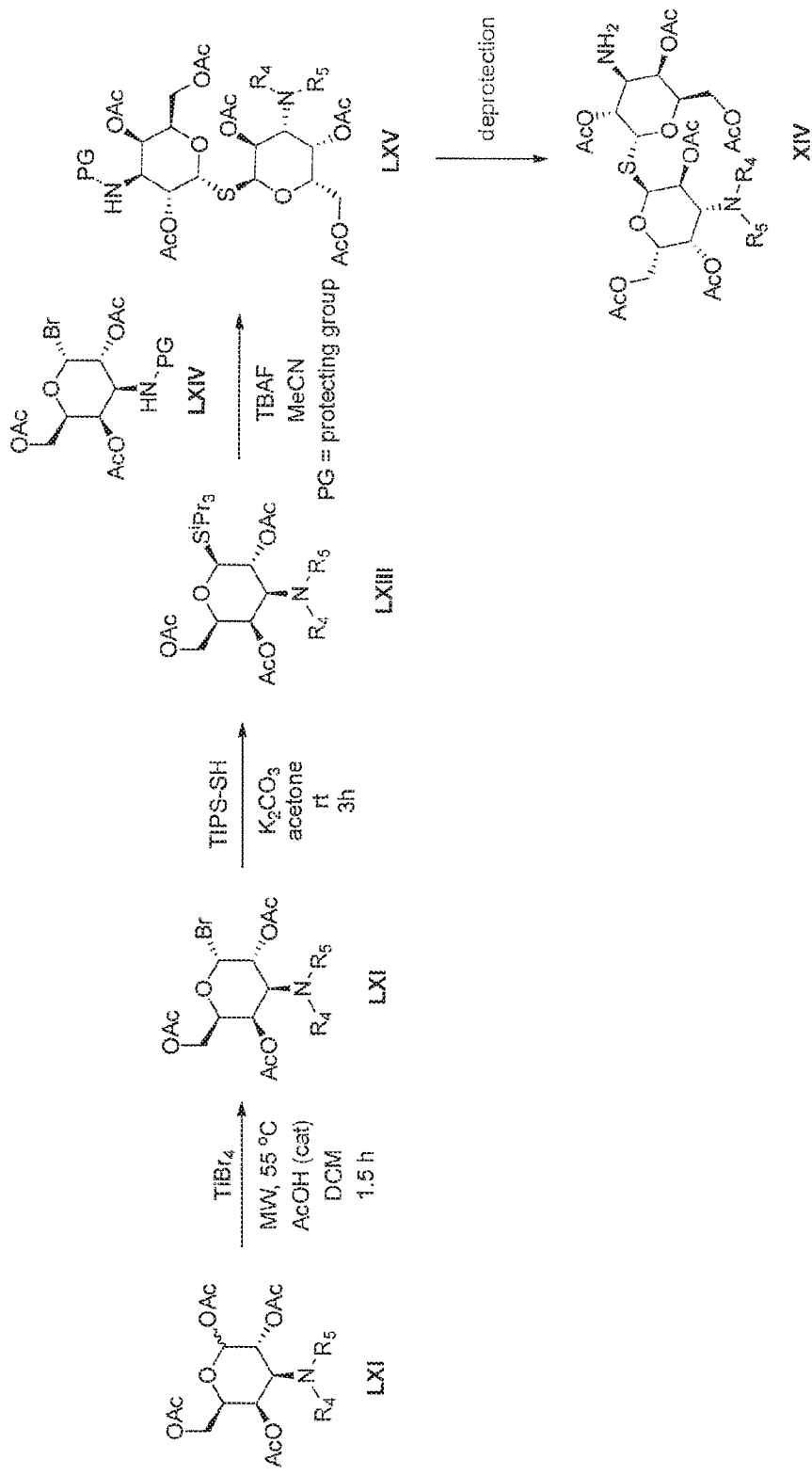
FIG. 13 Scheme 11: Synthesis of compounds of structural formula XIV, specifically shown in this figure as thiodigalactosides.

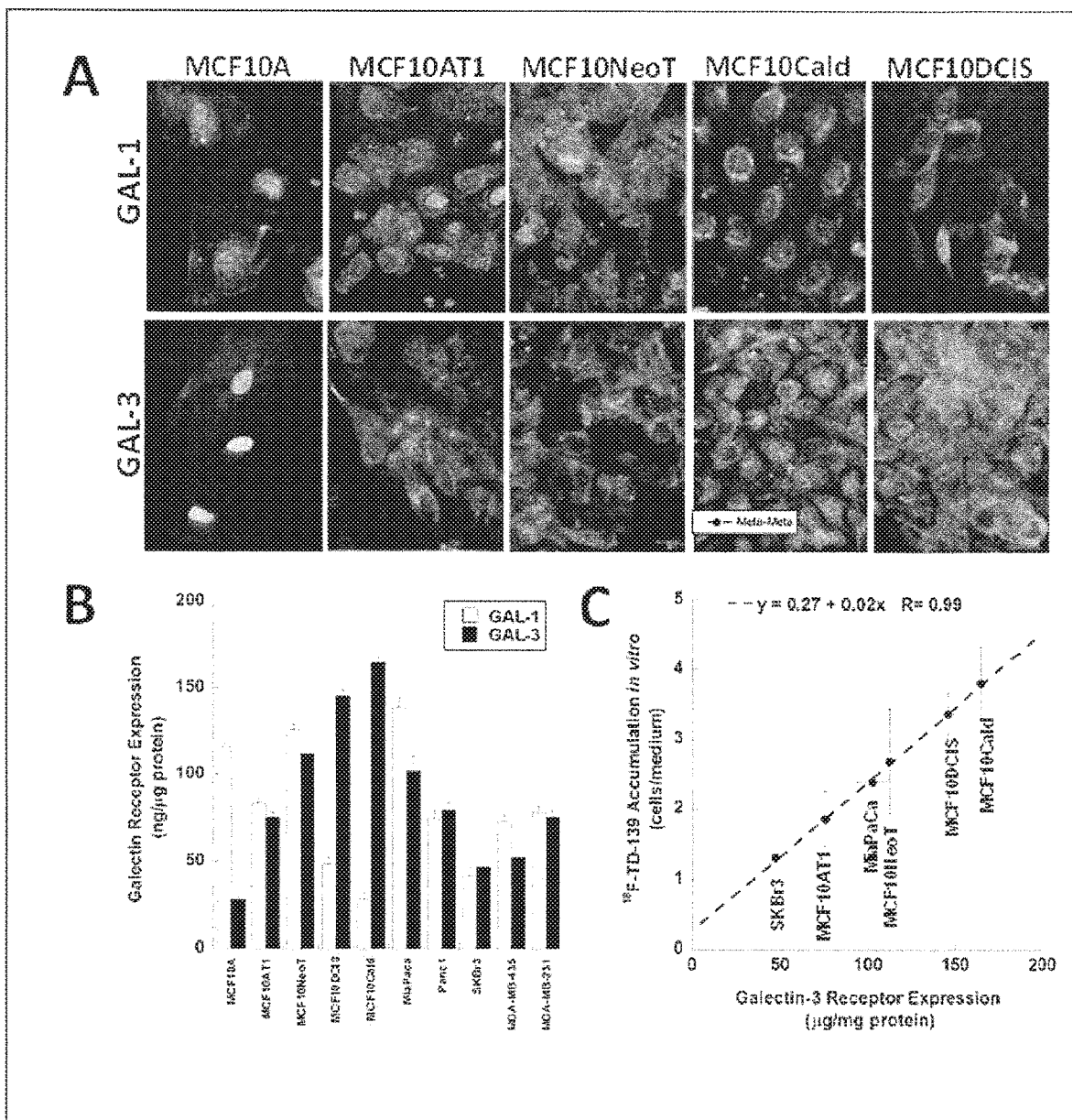
FIGS. 14A-C

PET/CT Images of 3-[¹⁸F]fluorophenyltriazolo thiodigalactoside [¹⁸F]FPTDG at 75 min after i.v. administration.

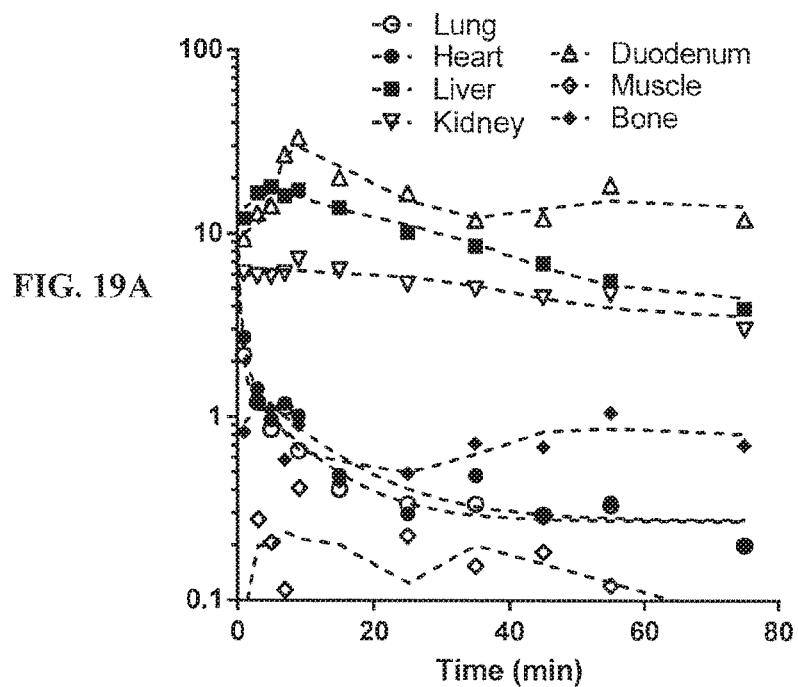
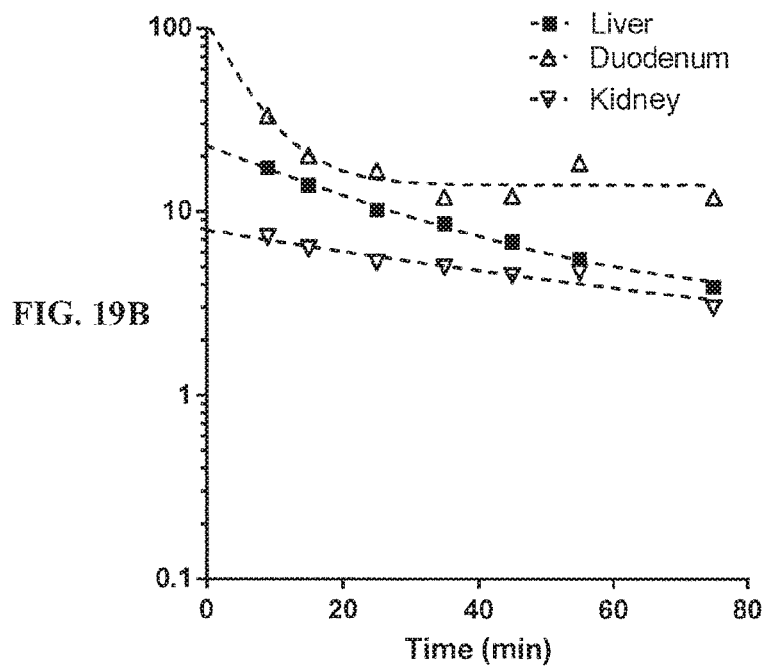

COMPOSITIONS AND METHODS RELATING TO GALECTIN DETECTION

REFERENCE TO RELATED APPLICATION

This application claims priority from U.S. Provisional Patent Application Ser. No. 62/197,338, filed Jul. 27, 2015, the entire content of which is incorporated herein by reference.

FIELD OF THE INVENTION

The present invention relates generally to compositions and methods for imaging of different galectins. In specific aspects, the present invention relates to compositions and methods for nuclear imaging and fluorescent imaging of galectins.

BACKGROUND OF THE INVENTION

Galectins are a group of proteins known for their ability to bind to β-galactoside sugars, either by N-linked or O-linked glycosylation see Cummings R D and Liu F T. Galectins. In: Varki A, Cummings R D, et al. eds. Essentials of Glycobiology. 2nd ed., NY: CSHL Press, 2009: Chapter 33; and Barondes S H et al., J. Biol. Chem., 1994, 269: 20807-10.

Galectins were first isolated from chick muscle and calf heart and lungs in 1976. Since then, galectins have been named in the order of discovery with as 15 members of the family identified so far. Each galectin has a carbohydrate recognition domain (CRD), and are classified according to the number and structure of these CRD. Galectins are therefore divided into tandem, dimeric and chimeric galectins. Dimeric galectins have two identical CRD subunits, tandem ones have two distinct CRD subunits and chimeric ones have one or even multiple subunits of the same type. Galectins-1, -2, -5, -7, -10, -11, -13, -14 and -15 are all dimeric galectins with galectins-4, -5, -8, -9 and -12 falling under the tandem category. Galectin-3 is the only chimeric galectin discovered in mammals thus far.

Galectins have been implicated in the development of cancer, the pathogenesis of heart failure and ventricular remodeling after myocardial infarction, infectious processes, such as HIV, and various other autoimmune and inflammatory processes, as well as in fibrotic tissues associated with different diseases. However, compositions and methods for detection and assessment of galectins are lacking.

SUMMARY OF THE INVENTION

Compositions are provided according to aspects of the present invention which include a labeled composition having the structural formula:

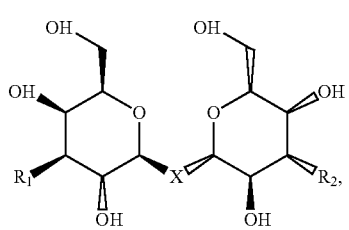

(I)

where $R_1$ is

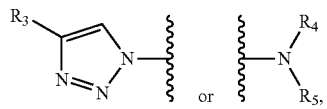

wherein $R_2$ is

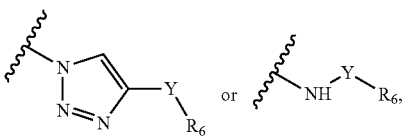

where $R_3$, $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label. According to particular aspects the aromatic ring is phenyl, naphthyl, thienyl, furyl or pyrrolyl. According to particular aspects, X is S.

Compositions are provided according to aspects of the present invention which include a labeled composition having the structural formula II, where $R_3$ is selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label. According to particular aspects the aromatic ring is phenyl, naphthyl, thienyl, furyl or pyrrolyl. According to particular aspects, X is S.

Compositions are provided according to aspects of the present invention which include a labeled composition having the structural formula III, where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label. According to particular aspects the aromatic ring is phenyl, naphthyl, thienyl, furyl or pyrrolyl. According to particular aspects, X is S.

Compositions are provided according to aspects of the present invention which include a labeled composition having the structural formula IV, where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label. According to particular aspects the aromatic ring is phenyl, naphthyl, thienyl, furyl or pyrrolyl. According to particular aspects, X is S.

Compositions are provided according to aspects of the present invention which include a labeled composition having the structural formula V:

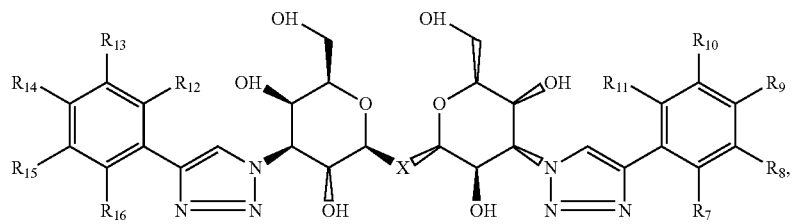

where each of $R_7$, $R_8$, $R_9$, $R_{10}$, $R_{11}$, $R_{12}$, $R_{13}$, $R_{14}$, $R_{15}$ and $R_{16}$ is independently selected from the group consisting of: H, $^{18}F$, $^{76}Br$, $^{123}I$, $^{124}I$, $^{125}I$ and $^{131}I$, wherein at least one of $R_7$, $R_8$, $R_9$, $R_{10}$, $R_{11}$, $R_{12}$, $R_{13}$, $R_{14}$, $R_{15}$ and $R_{16}$ is $^{18}F$, $^{76}Br$, $^{123}I$, $^{124}I$, $^{125}I$ or $^{131}I$. According to particular aspects, X is S.

Compositions are provided according to aspects of the present invention which include a labeled composition having the structural formula V:

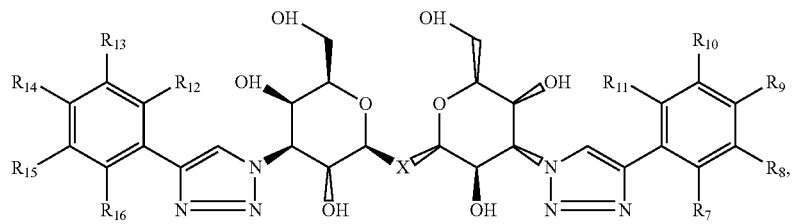

where $R_7$, $R_8$, $R_9$, $R_{10}$, $R_{11}$, $R_{12}$, $R_{13}$, $R_{14}$, $R_{15}$ are selected from the combinations 1-93 shown in Table I herein and X is C, Si, O, NH, $NCH_3$, S or Se. According to particular aspects, X is S and $R_7$, $R_8$, $R_9$, $R_{10}$, $R_{11}$, $R_{12}$, $R_{13}$, $R_{14}$, $R_{15}$ are selected from the combinations 1-93 shown in Table I herein.

Compositions are provided according to aspects of the present invention which include a labeled composition having the structural formula VI:

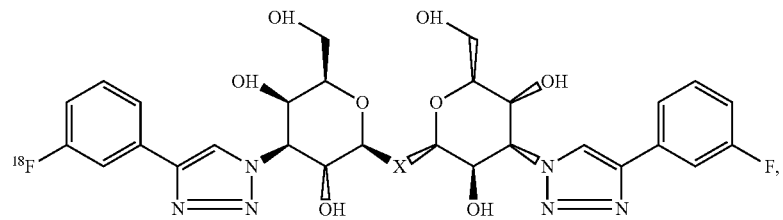

where X is C, Si, O, NH, $NCH_3$, S or Se.

According to particular aspects, compositions are provided according to aspects of the present invention which include a labeled composition having the structural formula VI, where X is S.

Compositions are provided according to aspects of the present invention which include a labeled composition having the structural formula VII:

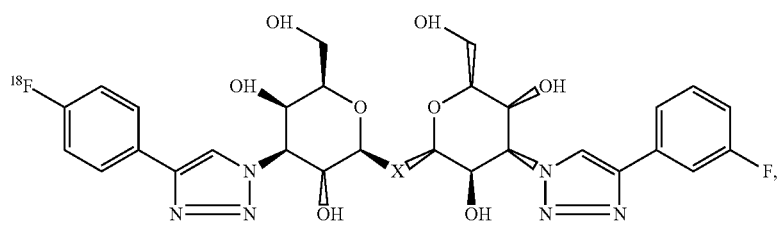

where X is C, Si, O, NH, NCH$_3$, S or Se. According to particular aspects, X is S.

Compositions are provided according to aspects of the present invention which include a labeled composition having the structural formula VIII:

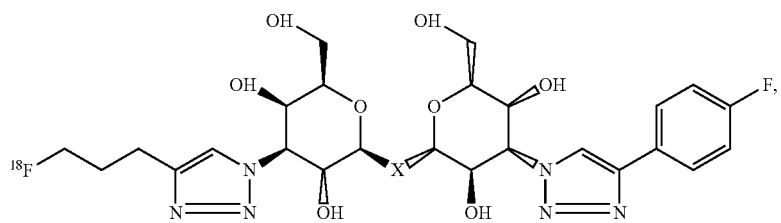

where X is C, Si, O, NH, NCH$_3$, S or Se. According to particular aspects, X is S.

Compositions are provided according to aspects of the present invention which include a labeled composition having the structural formula IX:

(IX)

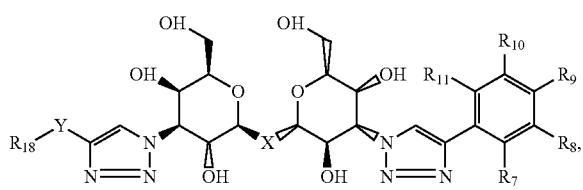

where each of R$_7$, R$_8$, R$_9$, R$_{10}$ and R$_{11}$ is independently selected from the group consisting of: H, F, Br, Cl, I, NO$_2$, NMe$_2$, NEt$_2$, Sn(Me)$_3$, NH$_2$, where X is C, Si, O, NH, NCH$_3$, S or Se, where Y is a substituted or unsubstituted aromatic ring, and where R$_{18}$ is a macrocyclic chelator complexed with a radionuclide. According to particular aspects, X is S.

Compositions are provided according to aspects of the present invention which include a labeled composition having the structural formula IX, where X is C, Si, O, NH, NCH$_3$, S or Se, where Y is a substituted or unsubstituted aromatic ring, and where R$_{18}$ is a macrocyclic chelator complexed with a radionuclide. where R$_7$, R$_8$, R$_9$, R$_{10}$ and R$_{11}$ are H, F, Br, Cl, I, NO$_2$, NMe$_2$, NEt$_2$, Sn(Me)$_3$ or NH$_2$ shown as combinations 94-357 in Table II and X is C, Si, O, NH, NCH$_3$, S or Se. According to particular aspects, X is S.

Precursor compositions are provided according to aspects of the present invention having the structural formula (X):

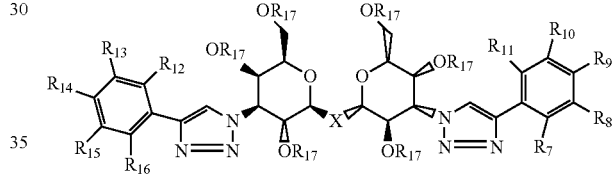

where each R$_{17}$ is a protecting group, where R$_7$, R$_8$, R$_9$, R$_{10}$, R$_{11}$, R$_{12}$, R$_{13}$, R$_{14}$, R$_{15}$ and R$_{16}$ are H, F, Br, I, NO$_2$, (NMe$_3$)$^+$TfO$^-$, (NEt$_3$)$^+$TfO$^-$, Sn(Me)$_3$ or NH$_2$ as shown in Table II as any one of combinations 94-357, where X is C, Si, O, NH, NCH$_3$, S or Se, wherein at least one of R$_7$, R$_8$, R$_9$, R$_{10}$, R$_{11}$, R$_{12}$, R$_{13}$, R$_{14}$, R$_{15}$ and R$_{16}$ is not H and with the proviso that R$_8$ and R$_{13}$ are not both fluorine.

Precursor compositions are provided according to aspects of the present invention having the structural formula (XI):

(XI)

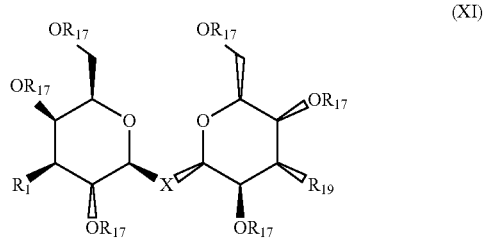

where R$_1$ is

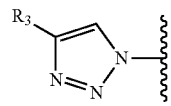

or

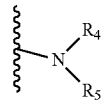

where $R_3$, $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where $R_{17}$ is a protective group and where $R_{19}$ is $N_3$ or $NH_2$. According to particular aspects the aromatic ring is phenyl, naphthyl, thienyl, furyl or pyrrolyl. According to particular aspects, X is S.

Precursor compositions are provided according to aspects of the present invention having the structural formula (XII):

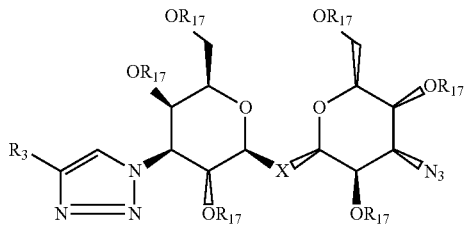

where $R_3$ is selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, and where $R_{17}$ is a protective group. According to particular aspects the aromatic ring is phenyl, naphthyl, thienyl, furyl or pyrrolyl. According to particular aspects, X is S.

Precursor compositions are provided according to aspects of the present invention having the structural formula (XIII):

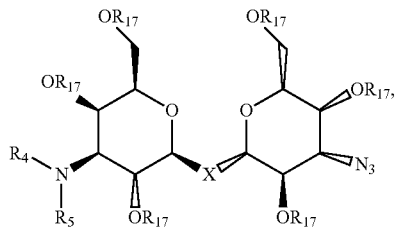

where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, and where $R_{17}$ is a protective group. According to particular aspects the aromatic ring is phenyl, naphthyl, thienyl, furyl or pyrrolyl. According to particular aspects, X is S.

Precursor compositions are provided according to aspects of the present invention having the structural formula (XIV):

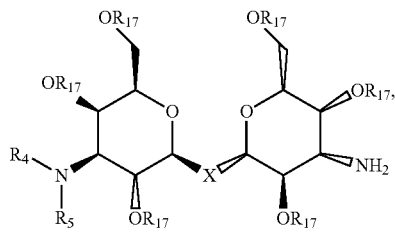

where $R_4$ and $R_5$ are each independently selected from the group consisting of a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, and where $R_{17}$ is a protective group. According to particular aspects the aromatic ring is phenyl, naphthyl, thienyl, furyl or pyrrolyl. According to particular aspects, X is S.

Precursor compositions are provided according to aspects of the present invention having the structural formula (XV):

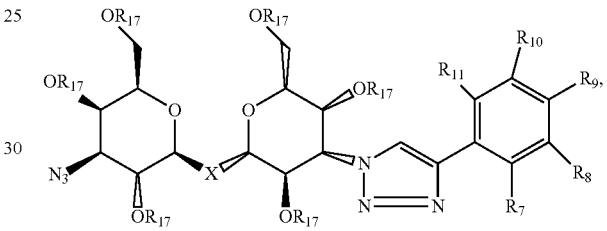

where $R_7$, $R_8$, $R_9$, $R_{10}$ and $R_{11}$ are each independently selected from the group consisting of: H, F, Br, Cl, I, $NO_2$, $NMe_2$, $NEt_2$, $Sn(Me)_3$ and $NH_2$, where X is C, Si, O, NH, $NCH_3$, S or Se, and where $R_{17}$ is a protective group. According to particular aspects, X is S.

Precursor compositions are provided according to aspects of the present invention having the structural formula XV where $R_7$, $R_8$, $R_9$, $R_{10}$ and $R_{11}$ are H, F, Br, Cl, I, $NO_2$, $NMe_2$, $NEt_2$, $Sn(Me)_3$ and $NH_2$ as shown in Table II as combinations 94-357, where X is C, Si, O, NH, $NCH_3$, S or Se, and where $R_{17}$ is a protective group.

Precursor compositions are provided according to aspects of the present invention having the structural formula XV where $R_7$, $R_8$, $R_9$, $R_{10}$ and $R_{11}$ are H, F, Br, Cl, I, $NO_2$, $NMe_2$, $NEt_2$, $Sn(Me)_3$ and $NH_2$ as shown in Table II as combinations 94-357, where X is S, and where $R_{17}$ is a protective group.

Precursor compositions are provided according to aspects of the present invention having the structural formula (XVI)

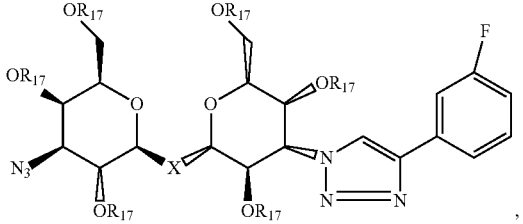

where X is C, Si, O, NH, $NCH_3$, S or Se, and where $R_{17}$ is a protective group.

Precursor compositions are provided according to aspects of the present invention having the structural formula (XVI), where X is S, and where $R_{17}$ is a protective group.

Precursor compositions are provided according to aspects of the present invention having the structural formula (XVII):

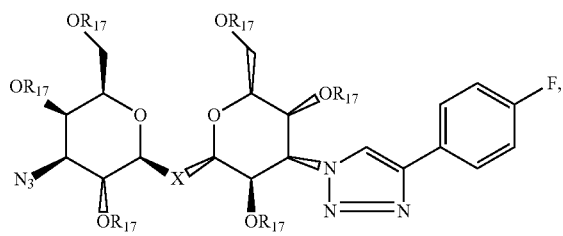

(XVII)

where X is C, Si, O, NH, NCH$_3$, S or Se, and where $R_{17}$ is a protective group.

Precursor compositions are provided according to aspects of the present invention having the structural formula (XVII), where X is S, and where $R_{17}$ is a protective group.

Precursor compositions are provided according to aspects of the present invention having the structural formula (XVIII):

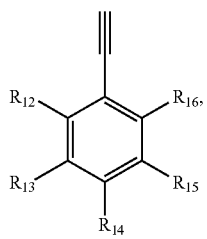

where $R_{12}$, $R_{13}$, $R_{14}$, $R_{15}$ and $R_{16}$ are selected from the group consisting of: $^{18}$F, $^{76}$Br, $^{123}$I, $^{124}$I, $^{125}$I or $^{131}$I, as shown in Table III as combinations 358-446.

Precursor compositions are provided according to aspects of the present invention having the structural formula (XX):

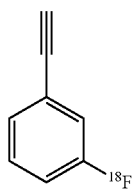

Precursor compositions are provided according to aspects of the present invention having the structural formula (XVIII):

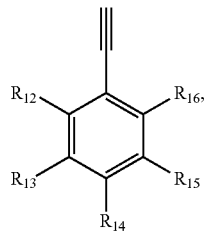

where $R_{12}$, $R_{13}$, $R_{14}$, $R_{15}$ and $R_{16}$ are selected from the group consisting of: H, F, Br, Cl, I, NO$_2$, (NMe$_3$)$^+$TfO$^-$, (NEt$_3$)$^+$TfO$^-$, Sn(Me)$_3$ and NH$_2$, as shown in Table IV as combinations 447-646.

Precursor compositions are provided according to aspects of the present invention having the structural formula (XIX):

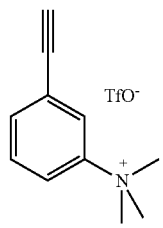

Precursor compositions are provided according to aspects of the present invention having the structural formula (XXI):

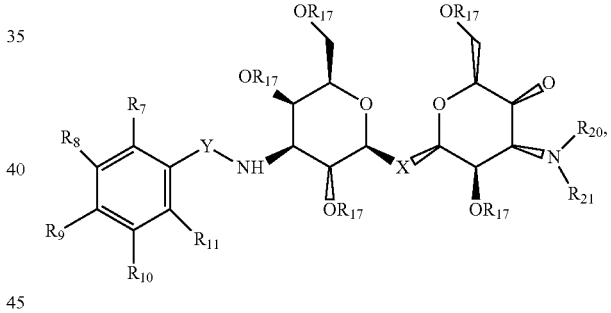

where each $R_{17}$ is a protecting group, where each $R_7$, $R_8$, $R_9$, $R_{10}$ and $R_{11}$ is independently selected from the group consisting of: H, OH, F, Br, Cl, I, N(Alk)$_2$, Sn(Alk)$_3$, SnCl$_2$, NO$_2$ and OTf, where X is C, Si, O, NH, NCH$_3$, S or Se, where Y is selected from the group consisting of: CH$_2$, —C=, carbonyl, —C(NH)—, —NH(CO), —NH(CS), where $R_{20}$ and $R_{21}$ are each independently selected from the group consisting of: a substituted or unsubstituted alkyl, alkenyl, alkyne, alkoxy, acyl, carbamoyl, aryl, heteroaryl, and peptidyl, and where at least one of $R_7$, $R_8$, $R_9$, $R_{10}$, and $R_{11}$ is not H.

Precursor compositions are provided according to aspects of the present invention having the structural formula (XXI), where each $R_{17}$ is a protecting group, where each $R_7$, $R_8$, $R_9$, $R_{10}$ and $R_{11}$ is independently selected from the group consisting of: H, OH, F, Br, Cl, I, N(Alk)$_2$, Sn(Alk)$_3$, SnCl$_2$, NO$_2$ and OTf, where X is S, where Y is selected from the group consisting of: CH$_2$, —C=, carbonyl, —C(NH)—, —NH(CO), —NH(CS), where $R_{20}$ and $R_{21}$ are each independently selected from the group consisting of: a substituted or unsubstituted alkyl, alkenyl, alkyne, alkoxy, acyl, carbamoyl, aryl, heteroaryl, and peptidyl, and where at least one of $R_7$, $R_8$, $R_9$, $R_{10}$, and $R_{11}$ is not H.

Precursor compositions are provided according to aspects of the present invention having the structural formula (XXI), where each $R_{17}$ is a protecting group, where each $R_7$, $R_8$, $R_9$, $R_{10}$ and $R_{11}$ is independently selected from the group consisting of: H, $^{18}F$, $^{76}Br$, $^{123/124/125/131}I$, and $^{11}C$, where X is C, Si, O, NH, $NCH_3$, S or Se, where Y is selected from the group consisting of: $CH_2$, —C═, carbonyl, —C(NH)—, —NH(CO), —NH(CS), where $R_1$ and $R_2$ are each independently selected from the group consisting of: a substituted or unsubstituted alkyl, alkenyl, alkyne, alkoxy, acyl, carbamoyl, aryl, heteroaryl, and peptidyl, and where at least one of $R_7$, $R_8$, $R_9$, $R_{10}$, and $R_{11}$ is not H. Precursor compositions are provided according to aspects of the present invention having the structural formula (XXI), where each $R_{17}$ is a protecting group, where each $R_7$, $R_8$, $R_9$, $R_{10}$ and $R_{11}$ is independently selected from the group consisting of: H, $^{18}F$, $^{76}Br$, $^{123/124/125/131}I$, and $^{11}C$, where X is S, where Y is selected from the group consisting of: $CH_2$, —C═, carbonyl, —C(NH)—, —NH(CO), —NH(CS), where $R_1$ and $R_2$ are each independently selected from the group consisting of: a substituted or unsubstituted alkyl, alkenyl, alkyne, alkoxy, acyl, carbamoyl, aryl, heteroaryl, and peptidyl, and where at least one of $R_7$, $R_8$, $R_9$, $R_{10}$, and $R_{11}$ is not H.

Labeled compositions, precursor compositions and pharmaceutical compositions including a labeled composition are provided according to aspects of the present invention wherein the labeled compositions or precursor composition is a derivative, salt, hydrate, amide or ester of a labeled composition or precursor composition according to any structural formula shown or described herein, including, but not limited to, any one of structural formulas I, II, III, IV, V, VI, VII, VIII, IX, X, XI, XII, XIII, XIV, XV, XVI, XVII, XVIII, XIX, XX and XXI.

Pharmaceutical compositions are provided according to aspects of the present invention which include a labeled composition or the present invention, further comprising a pharmaceutically acceptable carrier.

Methods of detecting a galectin are provided according to aspects of the present invention which include contacting a galectin with a labeled composition having the structural formula I, where $R_1$ is

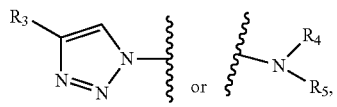

where $R_2$ is

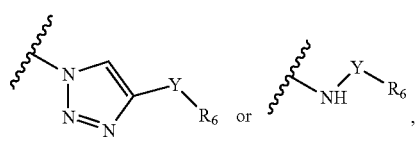

where $R_3$, $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label, under conditions to form a complex of the labeled composition and the galectin; and detecting a signal of the labeled composition in the complex of the labeled composition and the galectin. According to particular aspects the aromatic ring is phenyl, naphthyl, thienyl, furyl or pyrrolyl. According to particular aspects, X is S.

Methods of detecting a galectin are provided according to aspects of the present invention which include contacting a galectin with a labeled composition having the structural formula II, where $R_3$ is selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label, under conditions to form a complex of the labeled composition and the galectin; and detecting a signal of the labeled composition in the complex of the labeled composition and the galectin. According to particular aspects the aromatic ring is phenyl, naphthyl, thienyl, furyl or pyrrolyl. According to particular aspects, X is S.

Methods of detecting a galectin are provided according to aspects of the present invention which include contacting a galectin with a labeled composition having the structural formula I, where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label, under conditions to form a complex of the labeled composition and the galectin; and detecting a signal of the labeled composition in the complex of the labeled composition and the galectin. According to particular aspects the aromatic ring is phenyl, naphthyl, thienyl, furyl or pyrrolyl. According to particular aspects, X is S.

Methods of detecting a galectin are provided according to aspects of the present invention which include contacting a galectin with a labeled composition having the structural formula IV, where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label, under conditions to form a complex of the labeled composition and the galectin; and detecting a signal of the labeled composition in the complex of the labeled composition and the galectin. According to particular aspects the aromatic ring is phenyl, naphthyl, thienyl, furyl or pyrrolyl. According to particular aspects, X is S.

Methods of detecting a galectin are provided according to aspects of the present invention which include contacting a galectin with a labeled composition having the structural formula V, where each of $R_7$, $R_8$, $R_9$, $R_{10}$, $R_{11}$, $R_{12}$, $R_{13}$, $R_{14}$, $R_{15}$ and $R_{16}$ is independently selected from the group consisting of: H, $^{18}F$, $^{76}Br$, $^{123}I$, $^{124}I$, $^{125}I$ and $^{131}I$, wherein at least one of $R_7$, $R_8$, $R_9$, $R_{10}$, $R_{11}$, $R_{12}$, $R_{13}$, $R_{14}$, $R_{15}$ and $R_{16}$ is $^{18}F$, $^{76}Br$, $^{123}I$, $^{124}I$, $^{125}I$ or $^{131}I$, under conditions to form a complex of the labeled composition and the galectin; and detecting a signal of the labeled composition in the complex of the labeled composition and the galectin. According to particular aspects, X is S.

Methods of detecting a galectin are provided according to aspects of the present invention which include contacting a galectin with a labeled composition having the structural formula V, where $R_7, R_8, R_9, R_{10}, R_{11}, R_{12}, R_{13}, R_{14}, R_{15}$ are selected from the combinations 1-93 shown in Table I herein and X is C, Si, O, NH, NCH$_3$, S or Se. According to particular aspects, X is S and $R_7, R_8, R_9, R_{10}, R_{11}, R_{12}, R_{13}, R_{14}, R_{15}$ are selected from the combinations 1-93 shown in Table I herein, under conditions to form a complex of the labeled composition and the galectin; and detecting a signal of the labeled composition in the complex of the labeled composition and the galectin. According to particular aspects, X is S.

Methods of detecting a galectin are provided according to aspects of the present invention which include contacting a galectin with a labeled composition having the structural formula VI, where X is C, Si, O, NH, NCH$_3$, S or Se, under conditions to form a complex of the labeled composition and the galectin; and detecting a signal of the labeled composition in the complex of the labeled composition and the galectin. According to particular aspects, X is S.

Methods of detecting a galectin are provided according to aspects of the present invention which include contacting a galectin with a labeled composition having the structural formula VII, where X is C, Si, O, NH, NCH$_3$, S or Se, under conditions to form a complex of the labeled composition and the galectin; and detecting a signal of the labeled composition in the complex of the labeled composition and the galectin. According to particular aspects, X is S.

Methods of detecting a galectin are provided according to aspects of the present invention which include contacting a galectin with a labeled composition having the structural formula VIII, where X is C, Si, O, NH, NCH$_3$, S or Se, under conditions to form a complex of the labeled composition and the galectin; and detecting a signal of the labeled composition in the complex of the labeled composition and the galectin. According to particular aspects, X is S.

Methods of detecting a galectin are provided according to aspects of the present invention which include contacting a galectin with a labeled composition having the structural formula IX, where each of $R_7, R_8, R_9, R_{10}$ and $R_{11}$ is independently selected from the group consisting of: H, F, Br, Cl, I, NO$_2$, NMe$_2$, NEt$_2$, Sn(Me)$_3$, NH$_2$, where X is C, Si, O, NH, NCH$_3$, S or Se, where Y is a substituted or unsubstituted aromatic ring, and where $R_{18}$ is a macrocyclic chelator complexed with a radionuclide, under conditions to form a complex of the labeled composition and the galectin; and detecting a signal of the labeled composition in the complex of the labeled composition and the galectin. According to particular aspects the aromatic ring is phenyl, naphthyl, thienyl, furyl or pyrrolyl. According to particular aspects, X is S.

Methods of detecting a galectin are provided according to aspects of the present invention which include contacting a galectin with a labeled composition having the structural formula IX: where $R_7, R_8, R_9, R_{10}$ and $R_{11}$ are H, F, Br, Cl, I, NO$_2$, NMe$_2$, NEt$_2$, Sn(Me)$_3$ or NH$_2$ shown as combinations 94-357 in Table II, where Y is a substituted or unsubstituted aromatic ring, where $R_{18}$ is a macrocyclic chelator complexed with a radionuclide, and X is C, Si, O, NH, NCH$_3$, S or Se, under conditions to form a complex of the labeled composition and the galectin; and detecting a signal of the labeled composition in the complex of the labeled composition and the galectin. According to particular aspects, X is S.

Methods of detecting a galectin are provided according to aspects of the present invention, wherein the labeled composition includes a radionuclide and wherein detecting the signal includes obtaining a PET, SPECT or scintigraphic image.

Methods of detecting a galectin are provided according to aspects of the present invention, wherein the labeled composition comprises a fluorophore and wherein detecting the signal comprises obtaining a fluorescence image.

Methods of detecting a galectin are provided according to aspects of the present invention, wherein the galectin is in vitro.

Methods of detecting a galectin are provided according to aspects of the present invention, wherein the galectin is in a subject.

Methods of detecting a galectin are provided according to aspects of the present invention, wherein the galectin is in a subject, and wherein the subject has or is suspected of having cancer, heart failure, ventricular remodeling, an infection, an HIV infection, a pathological autoimmune condition and/or a pathological inflammatory condition.

Methods of detecting a galectin are provided according to aspects of the present invention, wherein the galectin is galectin-1 or galectin-3.

Methods of chemical synthesis of a labeled composition are provided according to aspects of the present invention, which include chemical reaction of a precursor composition as shown or described herein.

Methods of aiding in diagnosis and/or treatment of a condition characterized by upregulation of one or more galectins in a subject in need thereof are provided according to aspects of the present invention, which include contacting a galectin with a labeled composition having the structural formula I,
where $R_1$ is

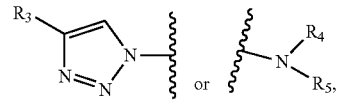

where $R_2$ is

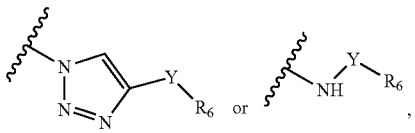

where $R_3$, $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, NCH$_3$, S or Se, where Y is a substituted or unsubstituted aromatic ring, and where $R_6$ is a radioactive or fluorescent label, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects the aromatic ring is phenyl, naphthyl, thienyl, furyl or pyrrolyl. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula II, where $R_3$ is selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects the aromatic ring is phenyl, naphthyl, thienyl, furyl or pyrrolyl. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula III, where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects the aromatic ring is phenyl, naphthyl, thienyl, furyl or pyrrolyl. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula IV, where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects the aromatic ring is phenyl, naphthyl, thienyl, furyl or pyrrolyl. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula V, where each of $R_7$, $R_8$, $R_9$, $R_{10}$, $R_{11}$, $R_{12}$, $R_{13}$, $R_{14}$, $R_{15}$ and $R_{16}$ is independently selected from the group consisting of: H, $^{18}F$, $^{76}Br$, $^{123}I$, $^{124}I$, $^{125}I$ and $^{131}I$, wherein at least one of $R_7$, $R_8$, $R_9$, $R_{10}$, $R_{11}$, $R_{12}$, $R_{13}$, $R_{14}$, $R_{15}$ and $R_{16}$ is $^{18}F$, $^{76}Br$, $^{123}I$, $^{124}I$, $^{125}I$ or $^{131}I$, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula V, where $R_7$, $R_8$, $R_9$, $R_{10}$, $R_{11}$, $R_{12}$, $R_{13}$, $R_{14}$, $R_{15}$ are selected from the combinations 1-93 shown in Table I herein and X is C, Si, O, NH, $NCH_3$, S or Se. According to particular aspects, X is S and $R_7$, $R_8$, $R_9$, $R_{10}$, $R_{11}$, $R_{12}$, $R_{13}$, $R_{14}$, $R_{15}$ are selected from the combinations 1-93 shown in Table I herein, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula VI, where X is C, Si, O, NH, $NCH_3$, S or Se, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula VII, where X is C, Si, O, NH, $NCH_3$, S or Se, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula VIII, where X is C, Si, O, NH, $NCH_3$, S or Se, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula IX, where each of $R_7$, $R_8$, $R_9$, $R_{10}$ and $R_{11}$ is independently selected from the group consisting of: H, F, Br, Cl, I, $NO_2$, $NMe_2$, $NEt_2$, $Sn(Me)_3$, $NH_2$, where X is C, Si, O, NH, $NCH_3$, S or Se, where Y is a substituted or unsubstituted aromatic ring, and where $R_{18}$ is a macrocyclic chelator complexed with a radionuclide, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects the aromatic ring is phenyl, naphthyl, thienyl, furyl or pyrrolyl. According to particular aspects, X is S.

Methods of aiding in diagnosis and/or treatment of a condition characterized by upregulation of one or more galectins in a subject in need thereof are provided according to aspects of the present invention, which include contacting a galectin with a labeled composition having the structural formula IX: where $R_7$, $R_8$, $R_9$, $R_{10}$ and $R_{11}$ are H, F, Br, Cl, I, $NO_2$, $NMe_2$, $NEt_2$, $Sn(Me)_3$ or $NH_2$ shown as combinations 94-357 in Table II and X is C, Si, O, NH, $NCH_3$, S or Se, under conditions to form a complex of the labeled composition and the galectin; detecting a signal of the labeled composition in the complex of the labeled composition and the galectin; and comparing the signal to a control, thereby determining the level of the one or more galectins in the subject. According to particular aspects, X is S.

Methods of aiding in diagnosis and/or treatment of a condition characterized by upregulation of one or more galectins in a subject in need thereof are provided according to aspects of the present invention, wherein the labeled composition includes a radionuclide and wherein detecting the signal includes obtaining a PET, SPECT or scintigraphic image.

Methods of aiding in diagnosis and/or treatment of a condition characterized by upregulation of one or more galectins in a subject in need thereof are provided according to aspects of the present invention, wherein the labeled composition comprises a fluorophore and wherein detecting the signal comprises obtaining a fluorescence image.

Methods of aiding in diagnosis and/or treatment of a condition characterized by upregulation of one or more galectins in a subject in need thereof are provided according to aspects of the present invention, wherein the one or more galectins are in a biological sample obtained from the subject.

Methods of aiding in diagnosis and/or treatment of a condition characterized by upregulation of one or more galectins in a subject in need thereof are provided according to aspects of the present invention, wherein contacting a galectin with a labeled composition includes administering the labeled composition to the subject.

Methods of aiding in diagnosis and/or treatment of a condition characterized by upregulation of one or more galectins in a subject in need thereof are provided according to aspects of the present invention, wherein the one or more galectins is in a subject, and wherein the subject has or is suspected of having cancer, heart failure, ventricular remodeling, an infection, an HIV infection, a pathological autoimmune condition and/or a pathological inflammatory condition.

Methods of aiding in diagnosis and/or treatment of a condition characterized by upregulation of one or more galectins in a subject in need thereof are provided according to aspects of the present invention, wherein the one or more galectins is galectin-1 and/or galectin-3.

Methods of aiding in diagnosis and/or treatment of a condition characterized by upregulation of one or more galectins in a subject in need thereof are provided according to aspects of the present invention, wherein the control is a level of the one or more galectins determined in the subject prior to administration of a treatment for the condition characterized by upregulation of one or more galectins.

Methods of aiding in diagnosis and/or treatment of a condition characterized by upregulation of one or more galectins in a subject in need thereof are provided according to aspects of the present invention, wherein the control is a reference level of the one or more galectins in a comparable subject or population of comparable subjects.

Commercial packages are provided according to aspects of the present invention including a labeled composition and/or precursor composition described herein; or a derivative, salt, hydrate, amide or ester thereof. One or more auxiliary components are optionally included in commercial packages of the present invention, such as a pharmaceutically acceptable carrier exemplified by a buffer, diluent or a reconstituting agent.

Commercial packages are provided according to aspects of the present invention including a labeled composition having the structural formula VI:

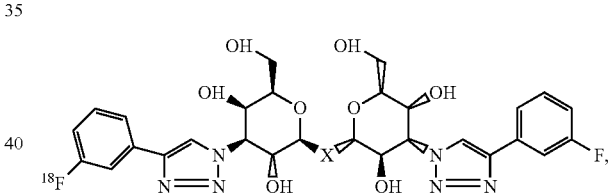

where X is C, Si, O, NH, $NCH_3$, S or Se; or a derivative, salt, hydrate, amide or ester of the labeled composition.

Commercial packages are provided according to aspects of the present invention including a labeled composition having the structural formula VI, where X is S; or a derivative, salt, hydrate, amide or ester of the labeled composition.

Commercial packages are provided according to aspects of the present invention including a labeled composition having the structural formula (VII):

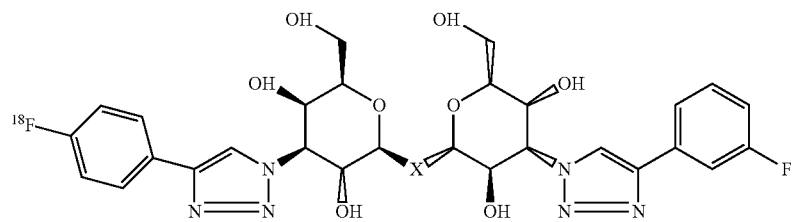

where X is C, Si, O, NH, $NCH_3$, S or Se; or a derivative, salt, hydrate, amide or ester of the labeled composition.

Commercial packages are provided according to aspects of the present invention including a labeled composition having the structural formula (VII), where X is S; or a derivative, salt, hydrate, amide or ester of the labeled composition.

Commercial packages are provided according to aspects of the present invention including a labeled composition having the structural formula (VIII):

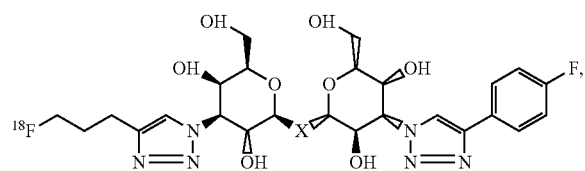

where X is C, Si, O, NH, NCH$_3$, S or Se; or a derivative, salt, hydrate, amide or ester of the labeled composition.

Commercial packages are provided according to aspects of the present invention including a labeled composition having the structural formula (VIII), where X is S; or a derivative, salt, hydrate, amide or ester of the labeled composition.

Commercial packages are provided according to aspects of the present invention including a precursor composition having the structural formula (XX):

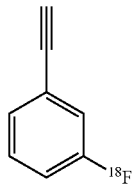

Commercial packages are provided according to aspects of the present invention including a precursor composition having the structural formula (XX) for use in "click" chemistry reactions.

Commercial packages are provided according to aspects of the present invention including a precursor composition having the structural formula having the structural formula (XIX):

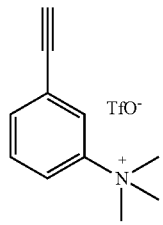

Commercial packages are provided according to aspects of the present invention including a precursor composition having the structural formula (XIX) for use in "click" chemistry reactions.

BRIEF DESCRIPTION OF THE DRAWINGS

FIG. 1 is a drawing illustrating chemical synthesis Scheme 1a;

FIG. 3 is a drawing illustrating chemical synthesis Schemes 2a and 2b;

FIG. 4 is a drawing illustrating chemical synthesis Schemes 3a, 3b and 3c;

FIG. 5 is a drawing illustrating chemical synthesis Schemes 4a and 4b;

FIG. 7 is a drawing illustrating chemical synthesis Scheme 5;

FIG. 8 is a drawing illustrating chemical synthesis Scheme 6;

FIG. 9 is a drawing illustrating chemical synthesis Scheme 7;

FIG. 10 is a drawing illustrating chemical synthesis Scheme 8;

FIG. 11 is a drawing illustrating chemical synthesis Scheme 9;

FIG. 12 is a drawing illustrating chemical synthesis Scheme 10;

FIG. 13 is a drawing illustrating chemical synthesis Scheme 11;

FIG. 14A shows images of magnitude and patterns of galectin-1 and galectin-3 levels in carcinoma cells MCF10A, MCF10AT1, MCF10NeoT, MCF10Cald, MCF10DCIS visualized using fluorescence microscopy;

FIG. 14B is a graph showing quantitative ELISA measurements of galectin-1 and galectin-3 levels on cellular membranes in carcinoma cells MCF10A, MCF10AT1, MCF10NeoT, MCF10Cald, MCF10DCIS, MiaPaCa, Panc 1, SKBr3, MDA-MB-435 and MDA-MB-231;

FIG. 14C is a graph showing results of an in vitro radiotracer binding/accumulation assay in cancer cells MCF10AT1, MCF10NeoT, MCF10Cald, MCF10DCIS, MiaPaCa, and SKBr3;

FIG. 19A is a graph showing time-activity curves of [$^{18}$F]FPTDG in different organs and tissues and its clearance from blood;

FIG. 19B is a graph showing time-activity curves of [$^{18}$F]FPTDG in organs and tissues involved in clearance from the body;

DETAILED DESCRIPTION OF THE INVENTION

Figure 1:
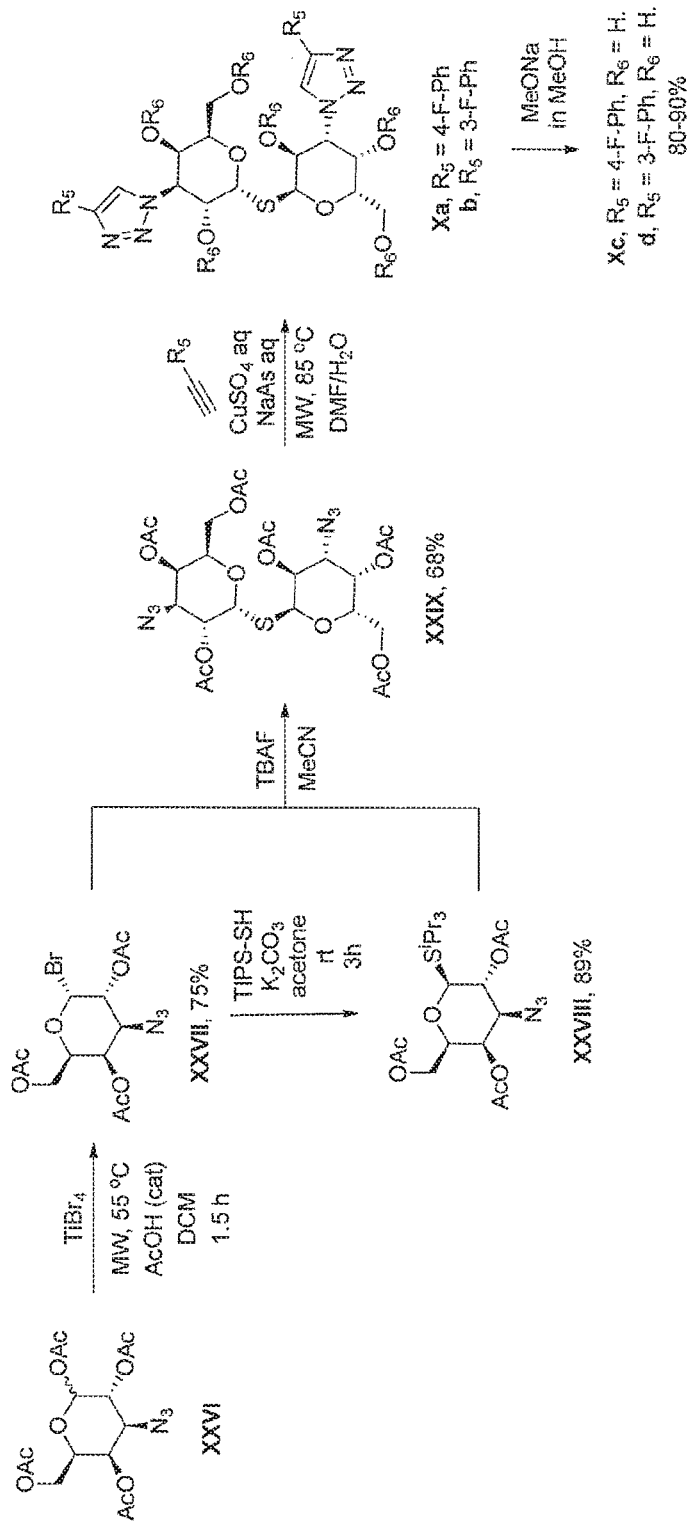
Figure 2:
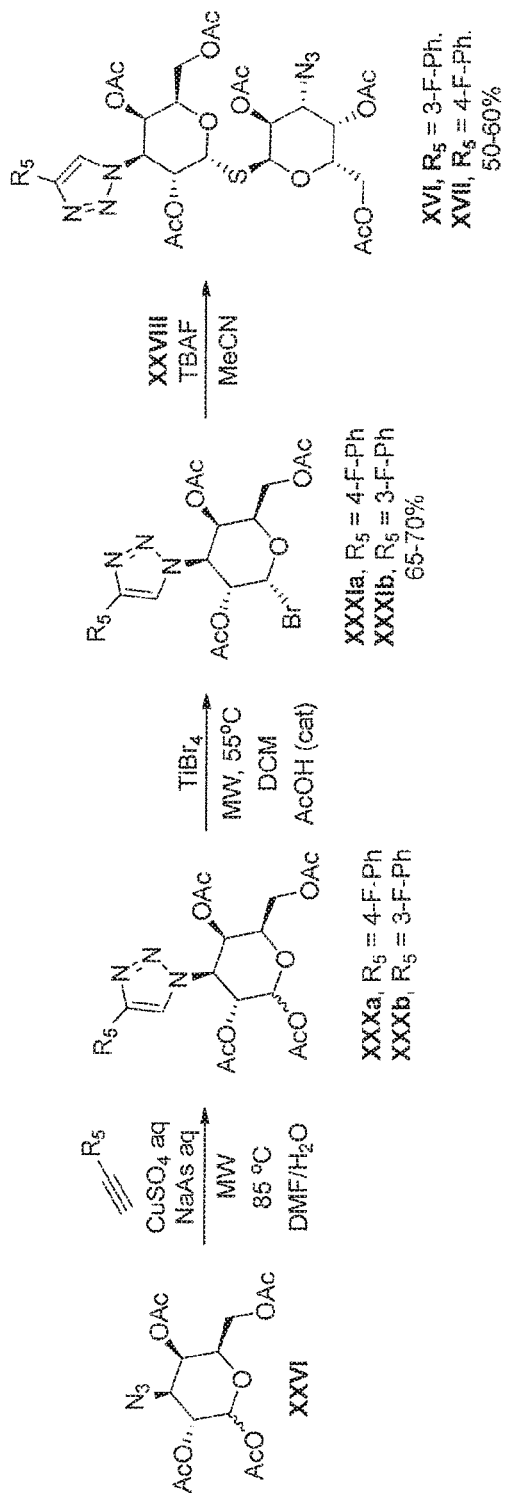
FIG. 2 is a drawing illustrating chemical synthesis Scheme 1b.
Figure 6:
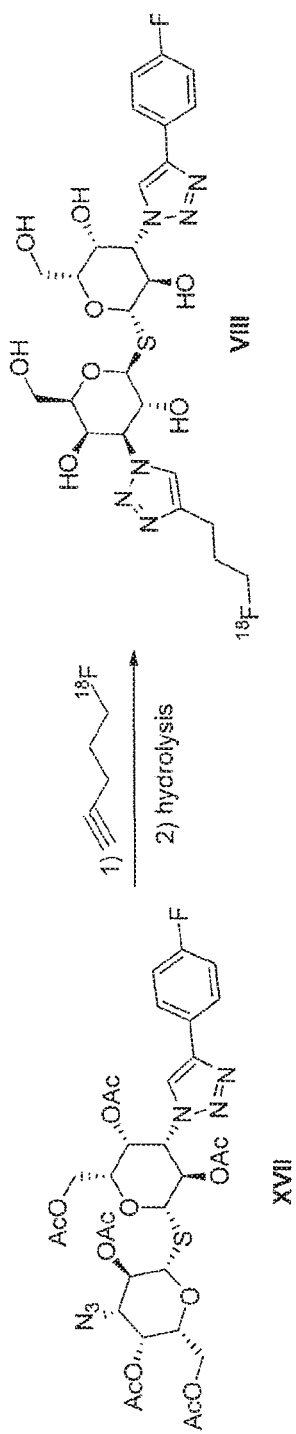
FIG. 6 is a drawing illustrating chemical synthesis Scheme 4c.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

The term "$^{123/124/125/131}$I" as used herein refers to an iodine isotope selected from the group consisting of: $^{123}$I, $^{124}$I, $^{125}$I and $^{131}$I.

The term "aromatic ring" as used herein refers to a polyatomic, cyclic, conjugated ring system which may include one or more heteroatoms. Examples of aromatic rings include phenyl, naphthyl, thenyl, furyl and pyrrolyl, among others. The term "substituted aromatic ring" refers to an aromatic ring system in which one or more hydrogen atoms bound to any carbon or heteroatom is replaced by one or more functional groups, such as, alkyl, substituted alkyl, cycloalkyl, substituted cycloalkyl, halogen, alkoxy, amino, nitro, thio, heterocycloalkyl, substituted heterocycloalkyl, and the like.

The term "alkyl" as used herein refers to a saturated, straight chain or branched, non-cyclic hydrocarbon having a chain length of 1-8 carbons.

The term "alkenyl" as used herein refers to an unsaturated, straight chain or branched, non-cyclic hydrocarbon with one or more carbon-carbon double bonds, having a chain length of 1-8 carbons.

The term "alkynyl" as used herein refers to an unsaturated, straight chain or branched, non-cyclic hydrocarbon with one or more carbon-carbon triple bonds, having a chain length of 1-8 carbons.

The term "alkoxy" as used herein refers to an oxygen having an attached alkyl group, —O-alkyl, exemplified by methoxy, ethoxy, propoxy, tert-butoxy, and the like.

The term "carbamoyl" as used herein refers to —O(C=O)NRR' where R and R' are each independently selected from H, alkyl, alkenyl, alkynyl and aromatic, such as N-ethylcarbamoyl, N,N-dimethylcarbamoyl and the like.

The term "chelator" as used herein refers to an agent that forms a chelation complex with a radionuclide. Chelators, such as macrocyclic chelators, are well known in the art and include 1,4,7,10-tetrazacyclododecane-N,N',N'',N'''-tetraacetic acid (DOTA), 1,4,7-triazacyclononane-N-glutaric acid-N',N''-diacetic acid (NODAGA), 1,4,7-triazacyclononane-N,N',N''-triacetic acid and the like.

The term "NMe$_3$" as used herein refers to trimethylamine.

The term "NEt$_3$" as used herein refers to triethylamine.

The term "Sn(Me)$_3$" as used herein refers to a trimethylstannyl group.

The term "(NMe$_3$)$^+$TfO$^-$" as used herein refers to trimethylammonium triflate.

The term "(NEt$_3$)$^+$TfO$^+$" as used herein refers to triethylammonium triflate.

The term "protective group" as used herein refers to a group attached to a functional group in order to prevent reaction of the functional group during a chemical reaction and which can be removed after the chemical reaction, restoring the functional group. Examples of protective groups which protect hydroxyl groups include acetate (Ac), benzoate (Bz), benzyl ether (Bn), methoxymethyl ether (MOM), p-Methoxybenzyl ether (PMB), pivalate (Piv) and the like. Protective groups for hydroxyl groups are well known in the art and one of skill in the art is able to select and use an appropriate protective group. In addition to those protective groups specifically mentioned, additional protective groups are known as described in Greene T. W. and Wuts P. G. M., Protective Groups in Organic Synthesis, 3rd Ed., published by John Wiley & Sons, 1999.

Labeled compositions, precursor compositions, methods of their use and methods of their synthesis are provided according to aspects of the present invention.

Labeled compositions according to aspects of the present invention have the structural formula (I)

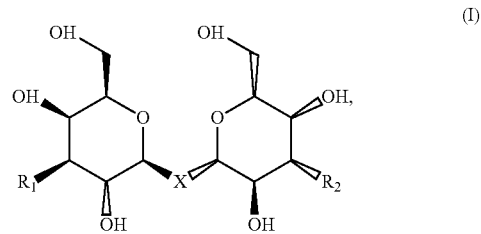

where $R_1$ is

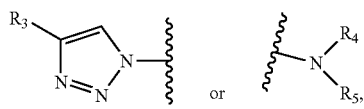

where $R_2$ is

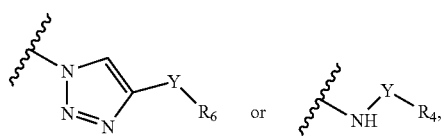

where $R_3$, $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring such as phenyl, naphthyl, thienyl, furyl or pyrrolyl, where X is C, Si, O, NH, $NCH_3$, S or Se, where Y is a substituted or unsubstituted aromatic ring such as phenyl, naphthyl, thienyl, furyl or pyrrolyl, and where $R_6$ is a radioactive or fluorescent label.

Labeled compositions according to aspects of the present invention have the structural formula (II)

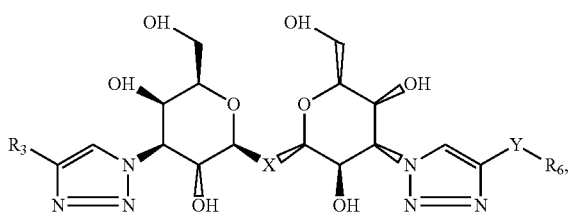

(II)

where $R_3$ is selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring such as phenyl, naphthyl, thienyl, furyl or pyrrolyl, where X is C, Si, O, NH, $NCH_3$, S or Se, where Y is a substituted or unsubstituted aromatic ring such as phenyl, naphthyl, thienyl, furyl or pyrrolyl, and where $R_6$ is a radioactive or fluorescent label.

Labeled compositions according to aspects of the present invention have the structural formula (III)

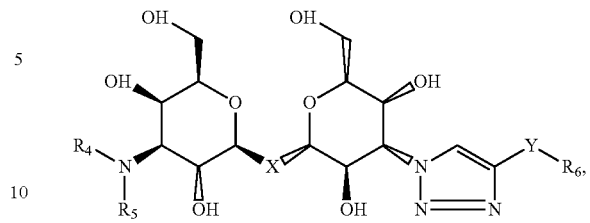

(III)

where $R_4$ and $R_5$ are independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring such as phenyl, naphthyl, thienyl, furyl or pyrrolyl, where X is C, Si, O, NH, $NCH_3$, S or Se, where Y is a substituted or unsubstituted aromatic ring such as phenyl, naphthyl, thienyl, furyl or pyrrolyl, and where $R_6$ is a radioactive or fluorescent label.

Labeled compositions according to aspects of the present invention have the structural formula (IV)

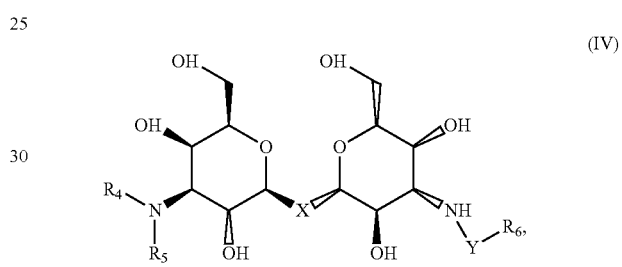

(IV)

where $R_4$ and $R_5$ are independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring such as phenyl, naphthyl, thienyl, furyl or pyrrolyl, where X is C, Si, O, NH, $NCH_3$, S or Se, where Y is a substituted or unsubstituted aromatic ring such as phenyl, naphthyl, thienyl, furyl or pyrrolyl, and where $R_6$ is a radioactive or fluorescent label.

Labeled compositions according to aspects of the present invention have the structural formula (V)

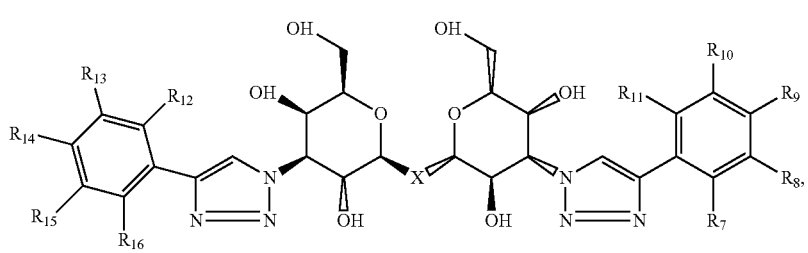

(V)

where each of $R_7$, $R_8$, $R_9$, $R_{10}$, $R_{11}$, $R_{12}$, $R_{13}$, R14, $R_{15}$ and $R_{16}$ is independently selected from the group consisting of: H, $^{18}F$, $^{76}Br$, $^{123}I$, $^{124}I$, $^{125}I$ and $^{131}I$, where at least one of $R_7$, $R_8$, $R_9$, $R_{10}$, $R_{11}$, $R_{12}$, $R_{13}$, $R_{14}$, $R_{15}$ and $R_{16}$ is $^{18}F$, $^{76}Br$, $^{123}I$, $^{124}I$, $^{125}I$ or $^{131}I$ and, where X is C, Si, O, NH, $NCH_3$, S or Se.

Labeled compositions according to aspects of the present invention have the structural formula (V), where X is C, Si, O, NH, NCH$_3$, S or Se, where each of R$_7$, R$_8$, R$_9$, R$_{10}$, R$_{11}$, R$_{12}$, R$_{13}$, R$_{14}$, R$_{15}$ and R$_{16}$ is independently selected from the group consisting of: H, $^{18}$F, $^{76}$Br, $^{123}$I, $^{124}$I, $^{125}$I and $^{131}$I, where at least one of R$_7$, R$_8$, R$_9$, R$_{10}$, R$_{11}$, R$_{12}$, R$_{13}$, R$_{14}$, R$_{15}$ and R$_{16}$ is $^{18}$F, $^{76}$Br, $^{123}$I, $^{124}$I, $^{125}$I or $^{131}$I are shown in Table I as any one of combinations 1-93.

TABLE I

| | R$_7$/R$_{12}$ or R$_{12}$/R$_7$ | R$_8$/R$_{13}$ or R$_{13}$/R$_8$ | R$_9$/R$_{14}$ or R$_{14}$/R$_9$ | R$_{10}$/R$_{15}$ or R$_{15}$/R$_{10}$ | R$_{11}$/R$_{16}$ or R$_{16}$/R$_{11}$ |
|---|---|---|---|---|---|
| 1 | $^{18}$F/F | H/H | H/H | H/H | H/H |
| 2 | $^{76}$Br/F | H/H | H/H | H/H | H/H |
| 3 | $^{123/124/125/131}$I/F | H/H | H/H | H/H | H/H |
| 4 | H/H | $^{18}$F/F | H/H | H/H | H/H |
| 5 | H/H | $^{76}$Br/F | H/H | H/H | H/H |
| 6 | H/H | $^{123/124/125/131}$I/F | H/H | H/H | H/H |
| 7 | H/H | H/H | $^{18}$F/F | H/H | H/H |
| 8 | H/H | H/H | $^{76}$Br/F | H/H | H/H |
| 9 | H/H | H/H | $^{123/124/125/131}$I/F | H/H | H/H |
| 10 | $^{18}$F/F | F/F | H/H | H/H | H/H |
| 11 | F/F | $^{18}$F/F | H/H | H/H | H/H |
| 12 | $^{76}$Br/F | F/F | H/H | H/H | H/H |
| 13 | $^{123/124/125/131}$I/F | F/F | H/H | H/H | H/H |
| 14 | F/F | $^{76}$Br/F | H/H | H/H | H/H |
| 15 | F/F | $^{123/124/125/131}$I/F | H/H | H/H | H/H |
| 16 | H/H | $^{18}$F/F | F/F | H/H | H/H |
| 17 | H/H | $^{76}$Br/F | F/F | H/H | H/H |
| 18 | H/H | $^{123/124/125/131}$I/F | F/F | H/H | H/H |
| 19 | H/H | F/F | $^{18}$F/F | H/H | H/H |
| 20 | H/H | F/F | $^{76}$Br/F | H/H | H/H |
| 21 | H/H | F/F | $^{123/124/125/131}$I/F | H/H | H/H |
| 22 | $^{18}$F/F | F/F | F/F | H/H | H/H |
| 23 | $^{76}$Br/F | F/F | F/F | H/H | H/H |
| 24 | $^{123/124/125/131}$I/F | F/F | F/F | H/H | H/H |
| 25 | F/F | $^{18}$F/F | F/F | H/H | H/H |
| 26 | F/F | $^{76}$Br/F | F/F | H/H | H/H |
| 27 | F/F | $^{123/124/125/131}$I/F | F/F | H/H | H/H |
| 28 | F/F | F/F | $^{18}$F/F | H/H | H/H |
| 29 | F/F | F/F | $^{76}$Br/F | H/H | H/H |
| 30 | F/F | F/F | $^{123/124/125/131}$I/F | H/H | H/H |
| 31 | H/H | $^{18}$F/F | F/F | F/F | H/H |
| 32 | H/H | $^{76}$Br/F | F/F | F/F | H/H |
| 33 | H/H | $^{123/124/125/131}$I/F | F/F | F/F | H/H |
| 34 | H/H | F/F | $^{18}$F/F | F/F | H/H |
| 35 | H/H | F/F | $^{76}$Br/F | F/F | H/H |
| 36 | H/H | F/F | $^{123/124/125/131}$I/F | F/F | H/H |
| 37 | H/H | $^{18}$F/F | H/H | F/F | H/H |
| 38 | H/H | $^{76}$Br/F | H/H | F/F | H/H |
| 39 | H/H | $^{123/124/125/131}$I/F | H/H | F/F | H/H |
| 40 | $^{18}$F/F | H/H | H/H | F/F | H/H |
| 41 | $^{76}$Br/F | H/H | H/H | F/F | H/H |
| 42 | $^{123/124/125/131}$I/F | H/H | H/H | F/F | H/H |
| 43 | F/F | H/H | H/H | $^{18}$F/F | H/H |
| 44 | F/F | H/H | H/H | $^{76}$Br/F | H/H |
| 45 | F/F | H/H | H/H | $^{123/124/125/131}$I/F | H/H |
| 46 | $^{18}$F/F | H/H | H/H | H/H | F/F |
| 47 | $^{76}$Br/F | H/H | H/H | H/H | F/F |
| 48 | $^{123/124/125/131}$I/F | H/H | H/H | H/H | F/F |
| 49 | $^{18}$F/F | F/F | H/H | H/H | F/F |
| 50 | $^{76}$Br/F | F/F | H/H | H/H | F/F |
| 51 | $^{123/124/125/131}$I/F | F/F | H/H | H/H | F/F |
| 52 | F/F | $^{18}$F/F | H/H | H/H | F/F |
| 53 | F/F | $^{76}$Br/F | H/H | H/H | F/F |
| 54 | F/F | $^{123/124/125/131}$I/F | H/H | H/H | F/F |
| 55 | F/F | F/F | H/H | H/H | $^{18}$F/F |
| 56 | F/F | F/F | H/H | H/H | $^{76}$Br/F |
| 57 | F/F | F/F | H/H | H/H | $^{123/124/125/131}$I/F |
| 58 | $^{18}$F/F | F/F | H/H | F/F | H/H |
| 59 | $^{76}$Br/F | F/F | H/H | F/F | H/H |
| 60 | $^{123/124/125/131}$I/F | F/F | H/H | F/F | H/H |
| 61 | F/F | $^{18}$F/F | H/H | F/F | H/H |
| 62 | F/F | $^{76}$Br/F | H/H | F/F | H/H |
| 63 | F/F | $^{123/124/125/131}$I/F | H/H | F/F | H/H |
| 64 | F/F | F/F | H/H | $^{18}$F/F | H/H |
| 65 | F/F | F/F | H/H | $^{76}$Br/F | H/H |
| 66 | F/F | F/F | H/H | $^{123/124/125/131}$I/F | H/H |
| 67 | $^{18}$F/F | H/H | F/F | H/H | F/F |
| 68 | $^{76}$Br/F | H/H | F/F | H/H | F/F |
| 69 | $^{123/124/125/131}$I/F | H/H | F/F | H/H | F/F |
| 70 | F/F | H/H | $^{18}$F/F | H/H | F/F |
| 71 | F/F | H/H | $^{76}$Br/F | H/H | F/F |

TABLE I-continued

| | $R_7/R_{12}$ or $R_{12}/R_7$ | $R_8/R_{13}$ or $R_{13}/R_8$ | $R_9/R_{14}$ or $R_{14}/R_9$ | $R_{10}/R_{15}$ or $R_{15}/R_{10}$ | $R_{11}/R_{16}$ or $R_{16}/R_{11}$ |
|---|---|---|---|---|---|
| 72 | F/F | H/H | $^{123/124/125/131}$I/F | H/H | F/F |
| 73 | H/H | $^{18}$F/F | F/F | H/H | F/F |
| 74 | H/H | $^{76}$Br/F | F/F | H/H | F/F |
| 75 | H/H | $^{123/124/125/131}$I/F | F/F | H/H | F/F |
| 76 | H/H | F/F | $^{18}$F/F | H/H | F/F |
| 77 | H/H | F/F | $^{76}$Br/F | H/H | F/F |
| 78 | H/H | F/F | $^{123/124/125/131}$I/F | H/H | F/F |
| 79 | H/H | F/F | F/F | H/H | $^{18}$F/F |
| 80 | H/H | F/F | F/F | H/H | $^{76}$Br/F |
| 81 | H/H | F/F | F/F | H/H | $^{123/124/125/131}$I/F |
| 82 | F/F | F/F | H/H | F/F | $^{18}$F/F |
| 83 | F/F | F/F | H/H | F/F | $^{76}$Br/F |
| 84 | F/F | F/F | H/H | F/F | $^{123/124/125/131}$I/F |
| 85 | F/F | F/F | H/H | $^{18}$F/F | F/F |
| 86 | F/F | F/F | H/H | $^{76}$Br/F | F/F |
| 87 | F/F | F/F | H/H | $^{123/124/125/131}$I/F | F/F |
| 88 | F/F | F/F | F/F | F/F | $^{18}$F/F |
| 89 | F/F | F/F | F/F | F/F | $^{76}$Br/F |
| 90 | F/F | F/F | F/F | F/F | $^{123/124/125/131}$I/F |
| 91 | F/F | F/F | $^{18}$F/F | F/F | F/F |
| 92 | F/F | F/F | $^{76}$Br/F | F/F | F/F |
| 93 | F/F | F/F | $^{123/124/125/131}$I/F | F/F | F/F |

Labeled compositions according to aspects of the present invention are any one of compositions defined in Table I selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92 or 93; or a mixture of any two or more thereof.

A labeled composition according to aspects of the present invention has the structural formula (VI)

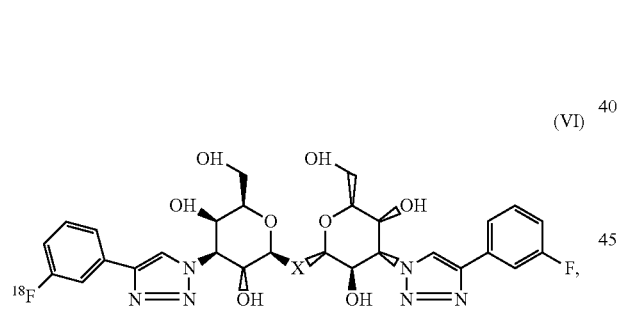

(VI)

where X is C, Si, O, NH, NCH$_3$, S or Se.

A labeled composition according to aspects of the present invention has the structural formula (VII)

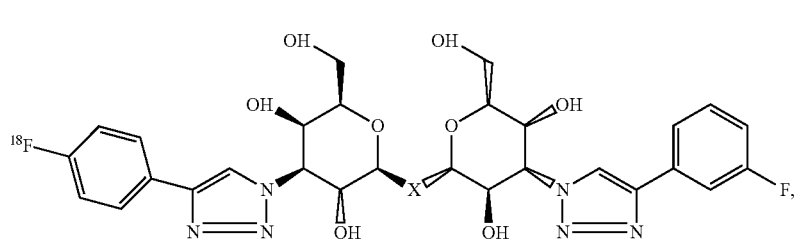

(VII)

where X is C, Si, O, NH, NCH$_3$, S or Se.

A labeled composition according to aspects of the present invention has the structural formula (VIII)

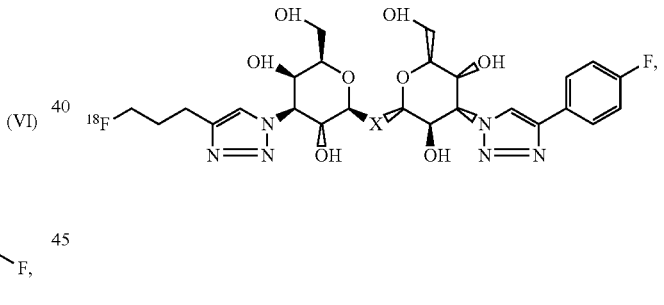

(VIII)

where X is C, Si, O, NH, NCH$_3$, S or Se.

Labeled compositions according to aspects of the present invention have the structural formula (IX)

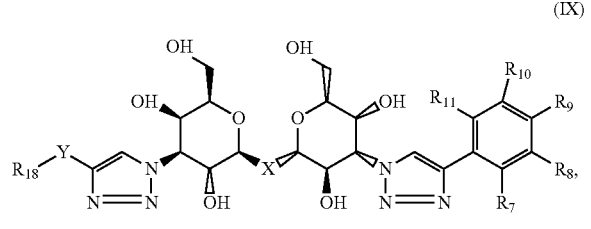

(IX)

where each of $R_7$, $R_8$, $R_9$, $R_{10}$ and $R_{11}$ is independently selected from the group consisting of: H, F, Br, Cl, I, $NO_2$, $NMe_2$, $MEt_2$, $Sn(Me)_3$, $NH_2$, where X is C, Si, O, NH, $NCH_3$, S or Se, where Y is H, a substituted or unsubstituted alkyl, alkenyl, alkyne, alkoxy, acyl, carbamoyl, aryl, heteroaryl, peptidyl, or a substituted or unsubstituted aromatic ring such as phenyl, naphthyl, thienyl, furyl or pyrrolyl, and where $R_{18}$ is a macrocyclic chelator such DOTA, NOTA and NODAGA or $R_{18}$ is a macrocyclic chelator complexed with a radionuclide, such as $^{67/68}Ga$, $^{89}Zr$, $^{99}mTc$, $^{111}In$ or $^{61/32/64}Cu$.

Labeled compositions according to aspects of the present invention have the structural formula (IX), where $R_7$, $R_8$, $R_9$, $R_{10}$ and $R_{11}$ are H, F, Br, Cl, I, $NO_2$, $NMe_2$, $MEt_2$, $Sn(Me)_3$ or $NH_2$ as shown in Table II as any one of combinations 94-357, where X is C, Si, O, NH, $NCH_3$, S or Se, where Y is H, a substituted or unsubstituted alkyl, alkenyl, alkyne, alkoxy, acyl, carbamoyl, aryl, heteroaryl, peptidyl, or a substituted or unsubstituted aromatic ring such as phenyl, naphthyl, thienyl, furyl or pyrrolyl, and where $R_{18}$ is a macrocyclic chelator such as DOTA, NOTA and NODAGA or $R_{18}$ is a macrocyclic chelator complexed with a radionuclide such as $^{67/68}Ga$, $^{89}Zr$, $^{99}mTc$, $^{111}In$ or $^{61/32/64}Cu$.

TABLE II

|  | R7 | R8 | R9 | R10 | R11 |
|---|---|---|---|---|---|
| 94 | F | H | H | H | H |
| 95 | Cl | H | H | H | H |
| 96 | Br | H | H | H | H |
| 97 | I | H | H | H | H |
| 98 | $NO_2$ | H | H | H | H |
| 99 | $NMe_2$ | H | H | H | H |
| 100 | $NEt_2$ | H | H | H | H |
| 101 | $Sn(Me)_3$ | H | H | H | H |
| 102 | $NH_2$ | H | H | H | H |
| 103 | H | F | H | H | H |
| 104 | H | Cl | H | H | H |
| 105 | H | Br | H | H | H |
| 106 | H | I | H | H | H |
| 107 | H | $NO_2$ | H | H | H |
| 108 | H | $NMe_2$ | H | H | H |
| 109 | H | $NEt_2$ | H | H | H |
| 110 | H | $Sn(Me)_3$ | H | H | H |
| 111 | H | $NH_2$ | H | H | H |
| 112 | H | H | F | H | H |
| 113 | H | H | Cl | H | H |
| 114 | H | H | Br | H | H |
| 115 | H | H | I | H | H |
| 116 | H | H | $NO_2$ | H | H |
| 117 | H | H | $NMe_2$ | H | H |
| 118 | H | H | $NEt_2$ | H | H |
| 119 | H | H | $Sn(Me)_3$ | H | H |
| 120 | H | H | $NH_2$ | H | H |
| 121 | F | F | H | H | H |
| 122 | Cl | F | H | H | H |
| 123 | Br | F | H | H | H |
| 124 | I | F | H | H | H |
| 125 | $NO_2$ | F | H | H | H |
| 126 | $NMe_2$ | F | H | H | H |
| 127 | $NEt_2$ | F | H | H | H |
| 128 | $Sn(Me)_3$ | F | H | H | H |
| 129 | $NH_2$ | F | H | H | H |
| 130 | F | Cl | H | H | H |
| 131 | F | Br | H | H | H |
| 132 | F | I | H | H | H |
| 133 | F | $NO_2$ | H | H | H |
| 134 | F | $NMe_2$ | H | H | H |
| 135 | F | $NEt_2$ | H | H | H |
| 136 | F | $Sn(Me)_3$ | H | H | H |
| 137 | F | $NH_2$ | H | H | H |
| 138 | H | F | F | H | H |
| 139 | H | Cl | F | H | H |
| 140 | H | Br | F | H | H |
| 141 | H | I | F | H | H |
| 142 | H | $NO_2$ | F | H | H |
| 143 | H | $NMe_2$ | F | H | H |
| 144 | H | $NEt_2$ | F | H | H |
| 145 | H | $Sn(Me)_3$ | F | H | H |
| 146 | H | $NH_2$ | F | H | H |
| 147 | H | F | Cl | H | H |
| 148 | H | F | Br | H | H |
| 149 | H | F | I | H | H |
| 150 | H | F | $NO_2$ | H | H |
| 151 | H | F | $NMe_2$ | H | H |
| 152 | H | F | $NEt_2$ | H | H |
| 153 | H | F | $Sn(Me)_3$ | H | H |
| 154 | H | F | $NH_2$ | H | H |
| 155 | F | F | F | H | H |
| 156 | Cl | F | F | H | H |
| 157 | Br | F | F | H | H |
| 158 | I | F | F | H | H |
| 159 | $NO_2$ | F | F | H | H |
| 160 | $NMe_2$ | F | F | H | H |
| 161 | $NEt_2$ | F | F | H | H |
| 162 | $Sn(Me)_3$ | F | F | H | H |
| 163 | $NH_2$ | F | F | H | H |
| 164 | F | Cl | F | H | H |
| 165 | F | Br | F | H | H |
| 166 | F | I | F | H | H |
| 167 | F | $NO_2$ | F | H | H |
| 168 | F | $NMe_2$ | F | H | H |
| 169 | F | $NEt_2$ | F | H | H |
| 170 | F | $Sn(Me)_3$ | F | H | H |
| 171 | F | $NH_2$ | F | H | H |
| 172 | F | F | Cl | H | H |
| 173 | F | F | Br | H | H |
| 174 | F | F | I | H | H |
| 175 | F | F | $NO_2$ | H | H |
| 176 | F | F | $NMe_2$ | H | H |
| 177 | F | F | $NEt_2$ | H | H |
| 178 | F | F | $Sn(Me)_3$ | H | H |
| 179 | F | F | $NH_2$ | H | H |
| 180 | H | F | F | F | H |
| 181 | H | Cl | F | F | H |
| 182 | H | Br | F | F | H |
| 183 | H | I | F | F | H |
| 184 | H | $NO_2$ | F | F | H |
| 185 | H | $NMe_2$ | F | F | H |
| 186 | H | $NEt_2$ | F | F | H |
| 187 | H | $Sn(Me)_3$ | F | F | H |
| 188 | H | $NH_2$ | F | F | H |
| 189 | H | F | Cl | F | H |
| 190 | H | F | Br | F | H |
| 191 | H | F | I | F | H |
| 192 | H | F | $NO_2$ | F | H |
| 193 | H | F | $NMe_2$ | F | H |
| 194 | H | F | $NEt_2$ | F | H |
| 195 | H | F | $Sn(Me)_3$ | F | H |
| 196 | H | F | $NH_2$ | F | H |
| 197 | H | F | H | F | H |
| 198 | H | Cl | H | F | H |
| 199 | H | Br | H | F | H |
| 200 | H | I | H | F | H |
| 201 | H | $NO_2$ | H | F | H |
| 202 | H | $NMe_2$ | H | F | H |
| 203 | H | $NEt_2$ | H | F | H |
| 204 | H | $Sn(Me)_3$ | H | F | H |
| 205 | H | $NH_2$ | H | F | H |

TABLE II-continued

|  | R7 | R8 | R9 | R10 | R11 |
|---|---|---|---|---|---|
| 206 | F | H | H | F | H |
| 207 | Cl | H | H | F | H |
| 208 | Br | H | H | F | H |
| 209 | I | H | H | F | H |
| 210 | $NO_2$ | H | H | F | H |
| 211 | $NMe_2$ | H | H | F | H |
| 212 | $NEt_2$ | H | H | F | H |
| 213 | $Sn(Me)_3$ | H | H | F | H |
| 214 | $NH_2$ | H | H | F | H |
| 215 | F | H | H | Cl | H |
| 216 | F | H | H | Br | H |
| 217 | F | H | H | I | H |
| 218 | F | H | H | $NO_2$ | H |
| 219 | F | H | H | $NMe_2$ | H |
| 220 | F | H | H | $NEt_2$ | H |
| 221 | F | H | H | $Sn(Me)_3$ | H |
| 222 | F | H | H | $NH_2$ | H |
| 223 | F | H | H | H | F |
| 224 | Cl | H | H | H | F |
| 225 | Br | H | H | H | F |
| 226 | I | H | H | H | F |
| 227 | $NO_2$ | H | H | H | F |
| 228 | $NMe_2$ | H | H | H | F |
| 229 | $NEt_2$ | H | H | H | F |
| 230 | $Sn(Me)_3$ | H | H | H | F |
| 231 | $NH_2$ | H | H | H | F |
| 232 | F | F | H | H | F |
| 233 | Cl | F | H | H | F |
| 234 | Br | F | H | H | F |
| 235 | I | F | H | H | F |
| 236 | $NO_2$ | F | H | H | F |
| 237 | $NMe_2$ | F | H | H | F |
| 238 | $NEt_2$ | F | H | H | F |
| 239 | $Sn(Me)_3$ | F | H | H | F |
| 240 | $NH_2$ | F | H | H | F |
| 241 | F | Cl | H | H | F |
| 242 | F | Br | H | H | F |
| 243 | F | I | H | H | F |
| 244 | F | $NO_2$ | H | H | F |
| 245 | F | $NMe_2$ | H | H | F |
| 246 | F | $NEt_2$ | H | H | F |
| 247 | F | $Sn(Me)_3$ | H | H | F |
| 248 | F | $NH_2$ | H | H | F |
| 249 | F | F | H | H | Cl |
| 250 | F | F | H | H | Br |
| 251 | F | F | H | H | I |
| 252 | F | F | H | H | $NO_2$ |
| 253 | F | F | H | H | $NMe_2$ |
| 254 | F | F | H | H | $NEt_2$ |
| 255 | F | F | H | H | $Sn(Me)_3$ |
| 256 | F | F | H | H | $NH_2$ |
| 257 | F | F | H | F | H |
| 258 | Cl | F | H | F | H |
| 259 | Br | F | H | F | H |
| 260 | I | F | H | F | H |
| 261 | $NO_2$ | F | H | F | H |
| 262 | $NMe_2$ | F | H | F | H |
| 263 | $NEt_2$ | F | H | F | H |
| 264 | $Sn(Me)_3$ | F | H | F | H |
| 265 | $NH_2$ | F | H | F | H |
| 266 | F | Cl | H | F | H |
| 267 | F | Br | H | F | H |
| 268 | F | I | H | F | H |
| 269 | F | $NO_2$ | H | F | H |
| 270 | F | $NMe_2$ | H | F | H |
| 271 | F | $NEt_2$ | H | F | H |
| 272 | F | $Sn(Me)_3$ | H | F | H |
| 273 | F | $NH_2$ | H | F | H |
| 274 | F | F | H | Cl | H |
| 275 | F | F | H | Br | H |
| 276 | F | F | H | I | H |
| 277 | F | F | H | $NO_2$ | H |
| 278 | F | F | H | $NMe_2$ | H |
| 279 | F | F | H | $NEt_2$ | H |
| 280 | F | F | H | $Sn(Me)_3$ | H |
| 281 | F | F | H | $NH_2$ | H |
| 282 | F | H | F | H | F |
| 283 | Cl | H | F | H | F |
| 284 | Br | H | F | H | F |
| 285 | I | H | F | H | F |
| 286 | $NO_2$ | H | F | H | F |
| 287 | $NMe_2$ | H | F | H | F |
| 288 | $NEt_2$ | H | F | H | F |
| 289 | $Sn(Me)_3$ | H | F | H | F |
| 290 | $NH_2$ | H | F | H | F |
| 291 | F | H | Cl | H | F |
| 292 | F | H | Br | H | F |
| 293 | F | H | I | H | F |
| 294 | F | H | $NH_2$ | H | F |
| 295 | F | H | $NMe_2$ | H | F |
| 296 | F | H | $NEt_2$ | H | F |
| 297 | F | H | $Sn(Me)_3$ | H | F |
| 298 | F | H | $NH_2$ | H | F |
| 299 | H | F | F | H | F |
| 300 | H | Cl | F | H | F |
| 301 | H | Br | F | H | F |
| 302 | H | I | F | H | F |
| 303 | H | $NO_2$ | F | H | F |
| 304 | H | $NMe_2$ | F | H | F |
| 305 | H | $NEt_2$ | F | H | F |
| 306 | H | $Sn(Me)_3$ | F | H | F |
| 307 | H | $NH_2$ | F | H | F |
| 308 | H | F | Cl | H | F |
| 309 | H | F | Br | H | F |
| 310 | H | F | I | H | F |
| 311 | H | F | $NO_2$ | H | F |
| 312 | H | F | $NMe_2$ | H | F |
| 313 | H | F | $NEt_2$ | H | F |
| 314 | H | F | $Sn(Me)_3$ | H | F |
| 315 | H | F | $NH_2$ | H | F |
| 316 | H | F | F | H | Cl |
| 317 | H | F | F | H | Br |
| 318 | H | F | F | H | I |
| 319 | H | F | F | H | $NO_2$ |
| 320 | H | F | F | H | $NMe_2$ |
| 321 | H | F | F | H | $NEt_2$ |
| 322 | H | F | F | H | $Sn(Me)_3$ |
| 323 | H | F | F | H | $NH_2$ |
| 324 | F | F | H | F | F |
| 325 | F | F | H | F | Cl |
| 326 | F | F | H | F | Br |
| 327 | F | F | H | F | I |
| 328 | F | F | H | F | $NO_2$ |
| 329 | F | F | H | F | $NMe_2$ |
| 330 | F | F | H | F | $NEt_2$ |
| 331 | F | F | H | F | $Sn(Me)_3$ |
| 332 | F | F | H | F | $NH_2$ |
| 333 | F | F | H | Cl | F |
| 334 | F | F | H | Br | F |
| 335 | F | F | H | I | F |
| 336 | F | F | H | $NO_2$ | F |
| 337 | F | F | H | $NMe_2$ | F |
| 338 | F | F | H | $NEt_2$ | F |
| 339 | F | F | H | $Sn(Me)_3$ | F |
| 340 | F | F | H | $NH_2$ | F |
| 341 | F | F | F | F | F |
| 342 | F | F | F | F | Cl |
| 343 | F | F | F | F | Br |
| 344 | F | F | F | F | I |
| 345 | F | F | F | F | $NO_2$ |
| 346 | F | F | F | F | $NMe_2$ |
| 347 | F | F | F | F | $NEt_2$ |
| 348 | F | F | F | F | $Sn(Me)_3$ |
| 349 | F | F | F | F | $NH_2$ |
| 350 | F | F | Cl | F | F |
| 351 | F | F | Br | F | F |
| 352 | F | F | I | F | F |
| 353 | F | F | $NO_2$ | F | F |
| 354 | F | F | $NMe_2$ | F | F |
| 355 | F | F | $NEt_2$ | F | F |
| 356 | F | F | $Sn(Me)_3$ | F | F |
| 357 | F | F | $NH_2$ | F | F |

Labeled compositions according to aspects of the present invention are any one of compositions defined in Table II selected from 94, 95, 96, 97, 98, 99, 100, 101 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356 or 357; or a mixture of any two or more thereof.

Precursor compositions according to aspects of the present invention have the structural formula (X)

where $R_1$ is

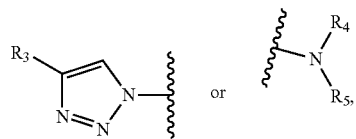

where $R_3$, $R_4$ and R5 are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring such as phenyl, naphthyl, thienyl, furyl or pyrrolyl, where X is C, Si, O, NH, NCH$_3$, S or Se, where $R_{17}$ is a protective group and where $R_{19}$ is $N_3$ or $NH_2$.

Precursor compositions according to aspects of the present invention have the structural formula (XII):

(X)

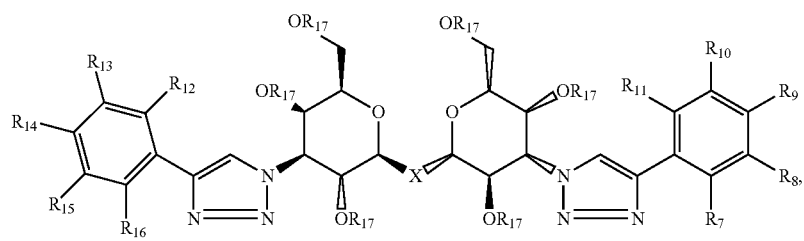

where each $R_{17}$ is a protecting group, where $R_7$, $R_8$, $R_9$, $R_{10}$, $R_{11}$, $R_{12}$, $R_{13}$, $R_{14}$, $R_{15}$ and $R_{16}$ are H, F, Br, I, NO$_2$, (NMe$_3$)$^+$TfO$^-$, (NEt$_3$)$^+$TfO$^-$, Sn(Me)$_3$ or NH$_2$ as shown in Table II as any one of combinations 94-357, where X is C, Si, O, NH, NCH$_3$, S or Se, wherein at least one of $R_7$, $R_8$, $R_9$, $R_{10}$, $R_{11}$, $R_{12}$, $R_{13}$, $R_{14}$, $R_{15}$ and $R_{16}$ is not H and with the proviso that $R_8$ and $R_{13}$ are not both fluorine.

Precursor compositions according to aspects of the present invention have the structural formula (XI)

(XI)

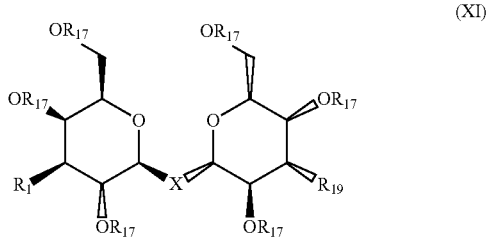

(XII)

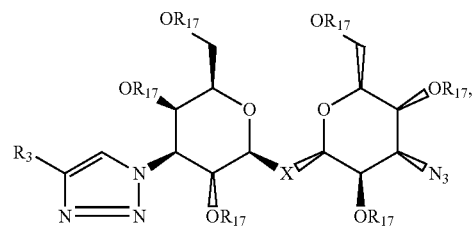

where $R_3$ is selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring such as phenyl, naphthyl, thienyl, furyl or pyrrolyl, where X is C, Si, O, NH, NCH$_3$, S or Se, and where $R_{17}$ is a protective group.

Compositions according to aspects of the present invention have the structural formula (XIII) and (XIV)

(XIII)

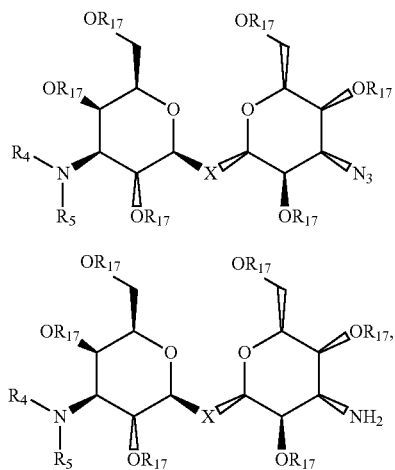

(XIV)

where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring such as phenyl, naphthyl, thienyl, furyl or pyrrolyl, where X is C, Si, O, NH, $NCH_3$, S or Se, and where $R_{17}$ is a protective group.

Precursor compositions according to aspects of the present invention have the structural formula (XV)

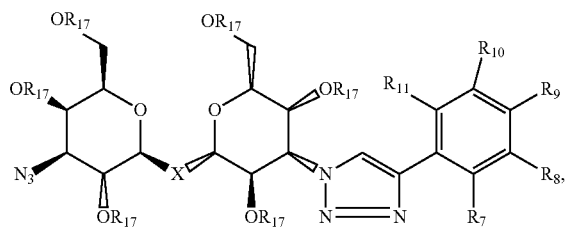

(XV)

where $R_7$, $R_8$, $R_9$, $R_{10}$ and $R_{11}$ are each independently selected from the group consisting of: H, F, Br, Cl, I, $NO_2$, $NMe_2$, $NEt_2$, $Sn(Me)_3$ and $NH_2$, where X is C, Si, O, NH, $NCH_3$, S or Se, and where $R_{17}$ is a protective group.

Precursor compositions according to aspects of the present invention have the structural formula (XV), where each $R_{17}$ is a protecting group, where $R_7$, $R_8$, $R_9$, $R_{10}$ and $R_{11}$ are H, F, Br, Cl, I, $NO_2$, $NMe_2$, $NEt_2$, $Sn(Me)_3$ and $NH_2$ as shown in Table II as combinations 94-357, and where X is C, Si, O, NH, $NCH_3$, S or Se.

Precursor compositions according to aspects of the present invention have the structural formula (XVI)

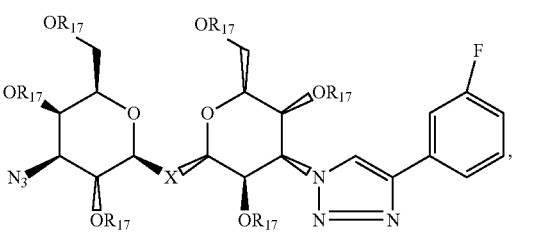

(XVI)

where each $R_{17}$ is a protecting group and where X is C, Si, O, NH, $NCH_3$, S or Se.

Precursor compositions according to aspects of the present invention have the structural formula (XVII)

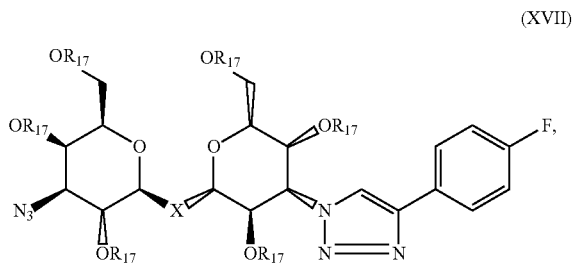

(XVII)

where X is C, Si, O, NH, $NCH_3$, S or Se, and where $R_{17}$ is a protective group.

Precursor compositions according to aspects of the present invention have the structural formula (XVIII)

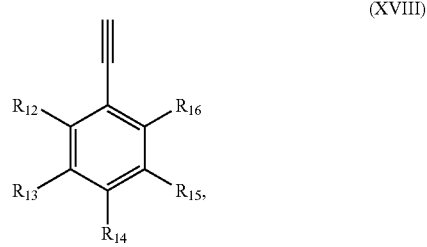

(XVIII)

$R_{12}$, $R_{13}$, $R_{14}$, $R_{15}$ and $R_{16}$ are selected from the group consisting of: $^{18}F$, $^{76}Br$, $^{123}I$, $^{124}I$, $^{125}I$ or $^{131}I$, as shown in Table III as combinations 358-446.

TABLE III

| | $R_{12}$ | $R_{13}$ | $R_{14}$ | $R_{15}$ | $R_{16}$ |
|---|---|---|---|---|---|
| 358 | $^{76}Br$ | H | H | H | H |
| 359 | $^{123/124/125/131}I$ | H | H | H | H |
| 360 | H | $^{18}F$ | H | H | H |
| 361 | H | $^{76}Br$ | H | H | H |
| 362 | H | $^{123/124/125/131}I$ | H | H | H |
| 363 | $^{18}F$ | F | H | H | H |
| 364 | F | $^{18}F$ | H | H | H |
| 365 | $^{76}Br$ | F | H | H | H |
| 366 | $^{123/124/125/131}I$ | F | H | H | H |
| 367 | F | $^{76}Br$ | H | H | H |
| 368 | F | $^{123/124/125/131}I$ | H | H | H |

TABLE III-continued

| | $R_{12}$ | $R_{13}$ | $R_{14}$ | $R_{15}$ | $R_{16}$ |
|---|---|---|---|---|---|
| 369 | H | $^{18}$F | F | H | H |
| 370 | H | $^{76}$Br | F | H | H |
| 371 | H | $^{123/124/125/131}$I | F | H | H |
| 372 | H | F | $^{18}$F | H | H |
| 373 | H | F | $^{76}$Br | H | H |
| 374 | H | F | $^{123/124/125/131}$I | H | H |
| 375 | $^{18}$F | F | F | H | H |
| 376 | $^{76}$Br | F | F | H | H |
| 377 | $^{123/124/125/131}$I | F | F | H | H |
| 378 | F | $^{18}$F | F | H | H |
| 379 | F | $^{76}$Br | F | H | H |
| 380 | F | $^{123/124/125/131}$I | F | H | H |
| 381 | F | F | $^{18}$F | H | H |
| 382 | F | F | $^{76}$Br | H | H |
| 383 | F | F | $^{123/124/125/131}$I | H | H |
| 384 | H | $^{18}$F | F | F | H |
| 385 | H | $^{76}$Br | F | F | H |
| 386 | H | $^{123/124/125/131}$I | F | F | H |
| 387 | H | F | $^{18}$F | F | H |
| 388 | H | F | $^{76}$Br | F | H |
| 389 | H | F | $^{123/124/125/131}$I | F | H |
| 390 | H | $^{18}$F | H | F | H |
| 391 | H | $^{76}$Br | H | F | H |
| 392 | H | $^{123/124/125/131}$I | H | F | H |
| 393 | $^{18}$F | H | H | F | H |
| 394 | $^{76}$Br | H | H | F | H |
| 395 | $^{123/124/125/131}$I | H | H | F | H |
| 396 | F | H | H | $^{18}$F | H |
| 397 | F | H | H | $^{76}$Br | H |
| 398 | F | H | H | $^{123/124/125/131}$I | H |
| 399 | $^{18}$F | H | H | H | F |
| 400 | $^{76}$Br | H | H | H | F |
| 401 | $^{123/124/125/131}$I | H | H | H | F |
| 402 | $^{18}$F | F | H | H | F |
| 403 | $^{76}$Br | F | H | H | F |
| 404 | $^{123/124/125/131}$I | F | H | H | F |
| 405 | F | $^{18}$F | H | H | F |
| 406 | F | $^{76}$Br | H | H | F |
| 407 | F | $^{123/124/125/131}$I | H | H | F |
| 408 | F | F | H | H | $^{18}$F |
| 409 | F | F | H | H | $^{76}$Br |
| 410 | F | F | H | H | $^{123/124/125/131}$I |
| 411 | $^{18}$F | F | H | F | H |
| 412 | $^{76}$Br | F | H | F | H |
| 413 | $^{123/124/125/131}$I | F | H | F | H |
| 414 | F | $^{18}$F | H | F | H |
| 415 | F | $^{76}$Br | H | F | H |
| 416 | F | $^{123/124/125/131}$I | H | F | H |
| 417 | F | F | H | $^{18}$F | H |
| 418 | F | F | H | $^{76}$Br | H |
| 419 | F | F | H | $^{123/124/125/131}$I | H |
| 420 | $^{18}$F | H | F | H | F |
| 421 | $^{76}$Br | H | F | H | F |
| 422 | $^{123/124/125/131}$I | H | F | H | F |
| 423 | F | H | $^{18}$F | H | F |
| 424 | F | H | $^{76}$Br | H | F |
| 425 | F | H | $^{123/124/125/131}$I | H | F |
| 426 | H | $^{18}$F | F | H | F |
| 427 | H | $^{76}$Br | F | H | F |
| 428 | H | $^{123/124/125/131}$I | F | H | F |
| 429 | H | F | $^{18}$F | H | F |
| 430 | H | F | $^{76}$Br | H | F |
| 431 | H | F | $^{123/124/125/131}$I | H | F |
| 432 | H | F | F | H | $^{18}$F |
| 433 | H | F | F | H | $^{76}$Br |
| 434 | H | F | F | H | $^{123/124/125/131}$I |
| 435 | F | F | H | F | $^{18}$F |
| 436 | F | F | H | F | $^{76}$Br |
| 437 | F | F | H | F | $^{123/124/125/131}$I |
| 438 | F | F | H | $^{18}$F | F |
| 439 | F | F | H | $^{76}$Br | F |
| 440 | F | F | H | $^{123/124/125/131}$I | F |
| 441 | F | F | F | F | $^{18}$F |
| 442 | F | F | F | F | $^{76}$Br |
| 443 | F | F | F | F | $^{123/124/125/131}$I |
| 444 | F | F | $^{18}$F | F | F |

TABLE III-continued

| | R$_{12}$ | R$_{13}$ | R$_{14}$ | R$_{15}$ | R$_{16}$ |
|---|---|---|---|---|---|
| 445 | F | F | $^{76}$Br | F | F |
| 446 | F | F | $^{123/124/125/131}$I | F | F |

Precursor compositions according to aspects of the present invention are any one of compositions defined in Table III selected from 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445 or 446; or a mixture of any two or more thereof.

Precursor compositions according to aspects of the present invention have the structural formula (XVIII)

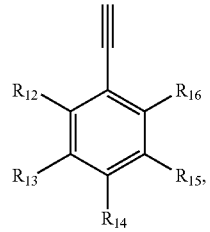

(XVIII)

R$_{12}$, R$_{13}$, R$_{14}$, R$_{15}$ and R$_{16}$ are selected from the group consisting of: H, F, Br, Cl, I, NO$_2$, (NMe$_3$)$^+$TfO$^-$, (NEt$_3$)$^+$TfO$^-$, Sn(Me)$_3$ and NH$_2$, as shown in Table IV as combinations 447-646.

TABLE IV

| | R$_1$ | R$_2$ | R$_3$ | R$_4$ | R$_5$ |
|---|---|---|---|---|---|
| 447 | (NMe$_3$)$^+$TfO$^-$ | H | H | H | H |
| 448 | (NEt$_2$Me)$^+$TfO$^-$ | H | H | H | H |
| 449 | Sn(Me)$_3$ | H | H | H | H |
| 450 | H | (NMe$_3$)$^+$TfO$^-$ | H | H | H |
| 451 | H | (NEt$_2$Me)$^+$TfO$^-$ | H | H | H |
| 452 | H | H | (NMe$_3$)$^+$TfO$^-$ | H | H |
| 453 | H | H | (NEt$_2$Me)$^+$TfO$^-$ | H | H |
| 454 | Cl | F | H | H | H |
| 455 | Br | F | H | H | H |
| 456 | I | F | H | H | H |
| 457 | NO$_2$ | F | H | H | H |
| 458 | (NMe$_3$)$^+$TfO$^-$ | F | H | H | H |
| 459 | (NEt$_2$Me)$^+$TfO$^-$ | F | H | H | H |
| 460 | Sn(Me)$_3$ | F | H | H | H |
| 461 | NH$_2$ | F | H | H | H |
| 462 | F | Br | H | H | H |
| 463 | F | I | H | H | H |
| 464 | F | NO$_2$ | H | H | H |
| 465 | F | (NMe$_3$)$^+$TfO$^-$ | H | H | H |
| 466 | F | (NEt$_2$Me)$^+$TfO$^-$ | H | H | H |
| 467 | F | Sn(Me)$_3$ | H | H | H |
| 468 | H | I | F | H | H |
| 469 | H | (NMe$_3$)$^+$TfO$^-$ | F | H | H |
| 470 | H | (NEt$_2$Me)$^+$TfO$^-$ | F | H | H |
| 471 | H | Sn(Me)$_3$ | F | H | H |
| 472 | H | F | I | H | H |
| 473 | H | F | NO$_2$ | H | H |
| 474 | H | F | (NMe$_3$)$^+$TfO$^-$ | H | H |
| 475 | H | F | (NEt$_2$Me)$^+$TfO$^-$ | H | H |
| 476 | H | F | Sn(Me)$_3$ | H | H |
| 477 | Cl | F | F | H | H |
| 478 | Br | F | F | H | H |
| 479 | I | F | F | H | H |
| 480 | NO$_2$ | F | F | H | H |
| 481 | (NMe$_3$)$^+$TfO$^-$ | F | F | H | H |
| 482 | (NEt$_2$Me)$^+$TfO$^-$ | F | F | H | H |
| 483 | Sn(Me)$_3$ | F | F | H | H |
| 484 | NH$_2$ | F | F | H | H |
| 485 | F | Cl | F | H | H |
| 486 | F | Br | F | H | H |
| 487 | F | I | F | H | H |
| 488 | F | NO$_2$ | F | H | H |
| 489 | F | (NMe$_3$)$^+$TfO$^-$ | F | H | H |
| 490 | F | (NEt$_2$Me)$^+$TfO$^-$ | F | H | H |
| 491 | F | Sn(Me)$_3$ | F | H | H |
| 492 | F | NH$_2$ | F | H | H |
| 493 | F | F | Cl | H | H |
| 494 | F | F | Br | H | H |

TABLE IV-continued

|  | R₁ | R₂ | R₃ | R₄ | R₅ |
|---|---|---|---|---|---|
| 495 | F | F | I | H | H |
| 496 | F | F | NO₂ | H | H |
| 497 | F | F | (NMe₃)⁺TfO⁻ | H | H |
| 498 | F | F | (NEt₂Me)⁺TfO⁻ | H | H |
| 499 | F | F | Sn(Me)₃ | H | H |
| 500 | F | F | NH₂ | H | H |
| 501 | H | Cl | F | F | H |
| 502 | H | Br | F | F | H |
| 503 | H | I | F | F | H |
| 504 | H | NO₂ | F | F | H |
| 505 | H | (NMe₃)⁺TfO⁻ | F | F | H |
| 506 | H | (NEt₂Me)⁺TfO⁻ | F | F | H |
| 507 | H | Sn(Me)₃ | F | F | H |
| 508 | H | NH₂ | F | F | H |
| 509 | H | F | Br | F | H |
| 510 | H | F | I | F | H |
| 511 | H | F | NO₂ | F | H |
| 512 | H | F | (NMe₃)⁺TfO⁻ | F | H |
| 513 | H | F | (NEt₂Me)⁺TfO⁻ | F | H |
| 514 | H | F | Sn(Me)₃ | F | H |
| 515 | H | Br | H | F | H |
| 516 | H | I | H | F | H |
| 517 | H | NO₂ | H | F | H |
| 518 | H | (NMe₃)⁺TfO⁻ | H | F | H |
| 519 | H | (NEt₂Me)⁺TfO⁻ | H | F | H |
| 520 | H | Sn(Me)₃ | H | F | H |
| 521 | Br | H | H | F | H |
| 522 | I | H | H | F | H |
| 523 | (NMe₃)⁺TfO⁻ | H | H | F | H |
| 524 | (NEt₂Me)⁺TfO⁻ | H | H | F | H |
| 525 | Sn(Me)₃ | H | H | F | H |
| 526 | F | H | H | I | H |
| 527 | F | H | H | (NMe₃)⁺TfO⁻ | H |
| 528 | F | H | H | (NEt₂Me)⁺TfO⁻ | H |
| 529 | F | H | H | Sn(Me)₃ | H |
| 530 | I | H | H | H | F |
| 531 | NO₂ | H | H | H | F |
| 532 | (NMe₃)⁺TfO⁻ | H | H | H | F |
| 533 | (NEt₂Me)⁺TfO⁻ | H | H | H | F |
| 534 | Sn(Me)₃ | H | H | H | F |
| 535 | NH₂ | H | H | H | F |
| 536 | Cl | F | H | H | F |
| 537 | Br | F | H | H | F |
| 538 | I | F | H | H | F |
| 539 | NO₂ | F | H | H | F |
| 540 | (NMe₃)⁺TfO⁻ | F | H | H | F |
| 541 | (NEt₂Me)⁺TfO⁻ | F | H | H | F |
| 542 | Sn(Me)₃ | F | H | H | F |
| 543 | NH₂ | F | H | H | F |
| 544 | F | Cl | H | H | F |
| 545 | F | Br | H | H | F |
| 546 | F | I | H | H | F |
| 547 | F | NO₂ | H | H | F |
| 548 | F | (NMe₃)⁺TfO⁻ | H | H | F |
| 549 | F | (NEt₂Me)⁺TfO⁻ | H | H | F |
| 550 | F | Sn(Me)₃ | H | H | F |
| 551 | F | NH₂ | H | H | F |
| 552 | F | F | H | H | Cl |
| 553 | F | F | H | H | Br |
| 554 | F | F | H | H | I |
| 555 | F | F | H | H | NO₂ |
| 556 | F | F | H | H | (NMe₃)⁺TfO⁻ |
| 557 | F | F | H | H | (NEt₂Me)⁺TfO⁻ |
| 558 | F | F | H | H | Sn(Me)₃ |
| 559 | F | F | H | H | NH₂ |
| 560 | Br | F | H | F | H |
| 561 | I | F | H | F | H |
| 562 | NO₂ | F | H | F | H |
| 563 | (NMe₃)⁺TfO⁻ | F | H | F | H |
| 564 | (NEt₂Me)⁺TfO⁻ | F | H | F | H |
| 565 | Sn(Me)₃ | F | H | F | H |
| 566 | F | Cl | H | F | H |
| 567 | F | Br | H | F | H |
| 568 | F | I | H | F | H |
| 569 | F | NO₂ | H | F | H |
| 570 | F | (NMe₃)⁺TfO⁻ | H | F | H |
| 571 | F | (NEt₂Me)⁺TfO⁻ | H | F | H |
| 572 | F | Sn(Me)₃ | H | F | H |

TABLE IV-continued

| | R₁ | R₂ | R₃ | R₄ | R₅ |
|---|---|---|---|---|---|
| 573 | F | NH₂ | H | F | H |
| 574 | F | F | H | Cl | H |
| 575 | F | F | H | Br | H |
| 576 | F | F | H | I | H |
| 577 | F | F | H | NO₂ | H |
| 578 | F | F | H | (NMe₃)⁺TfO⁻ | H |
| 579 | F | F | H | (NEt₂Me)⁺TfO⁻ | H |
| 580 | F | F | H | Sn(Me)₃ | H |
| 581 | F | F | H | NH₂ | H |
| 582 | Cl | H | F | H | F |
| 583 | Br | H | F | H | F |
| 584 | I | H | F | H | F |
| 585 | NO₂ | H | F | H | F |
| 586 | (NMe₃)⁺TfO⁻ | H | F | H | F |
| 587 | (NEt₂Me)⁺TfO⁻ | H | F | H | F |
| 588 | Sn(Me)₃ | H | F | H | F |
| 589 | NH₂ | H | F | H | F |
| 590 | F | H | Cl | H | F |
| 591 | F | H | Br | H | F |
| 592 | F | H | I | H | F |
| 593 | F | H | (NMe₃)⁺TfO⁻ | H | F |
| 594 | F | H | (NEt₂Me)⁺TfO⁻ | H | F |
| 595 | F | H | Sn(Me)₃ | H | F |
| 596 | H | Cl | F | H | F |
| 597 | H | Br | F | H | F |
| 598 | H | I | F | H | F |
| 599 | H | NO₂ | F | H | F |
| 600 | H | (NMe₃)⁺TfO⁻ | F | H | F |
| 601 | H | (NEt₂Me)⁺TfO⁻ | F | H | F |
| 602 | H | Sn(Me)₃ | F | H | F |
| 603 | H | NH₂ | F | H | F |
| 604 | H | F | Cl | H | F |
| 605 | H | F | Br | H | F |
| 606 | H | F | I | H | F |
| 607 | H | F | NO₂ | H | F |
| 608 | H | F | (NMe₃)⁺TfO⁻ | H | F |
| 609 | H | F | (NEt₂Me)⁺TfO⁻ | H | F |
| 610 | H | F | Sn(Me)₃ | H | F |
| 611 | H | F | F | H | Cl |
| 612 | H | F | F | H | Br |
| 613 | H | F | F | H | I |
| 614 | H | F | F | H | NO₂ |
| 615 | H | F | F | H | (NMe₃)⁺TfO⁻ |
| 616 | H | F | F | H | (NEt₂Me)⁺TfO⁻ |
| 617 | H | F | F | H | Sn(Me)₃ |
| 618 | F | F | H | F | Cl |
| 619 | F | F | H | F | Br |
| 620 | F | F | H | F | I |
| 621 | F | F | H | F | NO₂ |
| 622 | F | F | H | F | (NMe₃)⁺TfO⁻ |
| 623 | F | F | H | F | (NEt₂Me)⁺TfO⁻ |
| 624 | F | F | H | F | Sn(Me)₃ |
| 625 | F | F | H | F | NH₂ |
| 626 | F | F | H | Cl | F |
| 627 | F | F | H | Br | F |
| 628 | F | F | H | I | F |
| 629 | F | F | H | NO₂ | F |
| 630 | F | F | H | (NMe₃)⁺TfO⁻ | F |
| 631 | F | F | H | (NEt₂Me)⁺TfO⁻ | F |
| 632 | F | F | H | Sn(Me)₃ | F |
| 633 | F | F | H | NH₂ | F |
| 634 | F | F | F | F | Cl |
| 635 | F | F | F | F | Br |
| 636 | F | F | F | F | NO₂ |
| 637 | F | F | F | F | (NMe₃)⁺TfO⁻ |
| 638 | F | F | F | F | (NEt₂Me)⁺TfO⁻ |
| 639 | F | F | F | F | Sn(Me)₃ |
| 640 | F | F | Cl | F | F |
| 641 | F | F | Br | F | F |
| 642 | F | F | I | F | F |
| 643 | F | F | NO₂ | F | F |
| 644 | F | F | (NMe₃)⁺TfO⁻ | F | F |
| 645 | F | F | (NEt₂Me)⁺TfO⁻ | F | F |
| 646 | F | F | Sn(Me)₃ | F | F |

Precursor compositions according to aspects of the present invention are any one of compositions defined in Table IV selected from 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631.632, 633, 634, 635, 636, 637, 638, 639, 640, 641, 642, 643, 644, 645 or 646; or a mixture of any two or more thereof.

Precursor compositions according to aspects of the present invention have the structural formula (XIX).

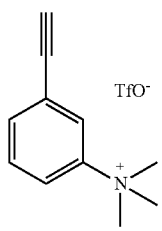

(XIX)

Precursor compositions according to aspects of the present invention have the structural formula (XX).

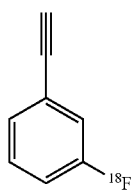

(XX)

Precursor compositions according to aspects of the present invention have the structural formula (XXI):

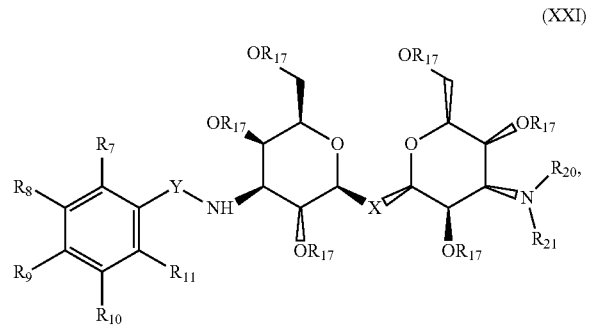

(XXI)

where each $R_{17}$ is a protecting group, where each $R_7$, $R_8$, $R_9$, $R_{10}$ and $R_{11}$ is independently selected from the group consisting of: H, OH, F, Br, Cl, I, $N(Alk)_2$, $Sn(Alk)_3$, $SnCl_2$, $NO_2$ and OTf, where X is C, Si, O, NH, $NCH_3$, S or Se, where Y is selected from the group consisting of: $CH_2$, —C=, carbonyl, —C(NH)—, —NH(CO), —NH(CS), where $R_{20}$ and $R_{21}$ are each independently selected from the group consisting of: a substituted or unsubstituted alkyl, alkenyl, alkyne, alkoxy, acyl, carbamoyl, aryl, heteroaryl, and peptidyl, and where at least one of $R_7$, $R_8$, $R_9$, $R_{10}$, and $R_{11}$ is not H.

Compositions according to aspects of the present invention have the structural formula (XXI), where each $R_7$, $R_8$, $R_9$, $R_{10}$ and $R_{11}$ is independently selected from the group consisting of: H, $^{18}F$, $^{76}Br$, $^{123/124/125/131}I$, and $^{11}C$, where X is C, Si, O, NH, $NCH_3$, S or Se, where Y is selected from the group consisting of: $CH_2$, —C=, carbonyl, —C(NH)—, —NH(CO), —NH(CS), where $R_1$ and $R_2$ are each independently selected from the group consisting of: a substituted or unsubstituted alkyl, alkenyl, alkyne, alkoxy, acyl, carbamoyl, aryl, heteroaryl, and peptidyl, and where at least one of $R_7$, $R_8$, $R_9$, $R_{10}$, and $R_{11}$ is not H.

Synthesis

Synthesis of compositions described and shown herein are provided according to aspects of the present invention.

Compositions having the structural formula I are synthesized according to Schemes 5, 6, 7, 8 and 9.

Compositions having the structural formula II are synthesized according to Schemes 5 and 6.

Compositions having the structural formula III are synthesized according to Schemes 7, 8 and 9.

Compositions having the structural formula IV are synthesized according to Scheme 8.

Compositions having the structural formula V are synthesized according to Scheme 5, 6, and 9.

Compositions having the structural formula VI are synthesized according to Scheme 4a.

Compositions having the structural formula VII are synthesized according to Scheme 4b.

Compositions having the structural formula VIII are synthesized according to Scheme 4c.

Compositions having the structural formula IX are synthesized according to Scheme 9.

Compositions having the structural formula X are synthesized according to Schemes 5, 6, and 9.

Compositions having the structural formula XI are synthesized according to Scheme 1b.

Compositions having the structural formula XII are synthesized according to Scheme 1b.

Compositions having the structural formula XIII are synthesized according to Scheme 10.

Compositions having the structural formula XIV are synthesized according to Scheme 11.

Compositions having the structural formula XV are synthesized according to Scheme 1b.

Compositions having the structural formula XVI are synthesized according to Scheme 1b.

Compositions having the structural formula XVII are synthesized according to Scheme 1b.

Compositions having the structural formula XVIII are synthesized according to Schemes 2a, 2b, 3a, 3b, 3c and 6.

Compositions having the structural formula XIX are synthesized according to Schemes 2a, 2b and 6.

Compositions having the structural formula XX are synthesized according to Schemes 3b and 6.

Compositions having the structural formula XXI are synthesized according to Scheme 8.

Precursor compositions according to aspects of the present invention are useful as precursors in chemical synthesis reactions of labeled compositions as well as synthesis of other compositions.

Labeled compositions according to aspects of the present invention are capable of specific binding to one or more galectins and useful for binding, targeting, inhibiting and imaging galectins in vitro and in vivo. Implication of galectins in the development of cancer, the pathogenesis of heart failure and ventricular remodeling, various fibrotic diseases, various other autoimmune and inflammatory processes, and infectious processes, such as HIV, supports utility of labeled compositions described herein for binding, targeting, inhibiting and imaging galectins.

The term "label" refers to a material capable of producing a signal indicative of the presence of a labeled composition incorporating the label by any appropriate method illustratively including spectroscopic, optical, photochemical, biochemical, enzymatic, electrical and/or immunochemical label detection methods. Examples of detectable labels illustratively include a fluorescent moiety, a chemiluminescent moiety, a bioluminescent moiety, a magnetic particle, an enzyme, a substrate, a radionuclide and a chromophore. The choice of label will depend on the detection method to be used.

In a particular aspect, the label is a radionuclide.

Radiolabels incorporated in labeled compositions according to aspects of the present invention include any radionuclide useful in imaging or useful in therapeutic applications, including $^{18}$F, $^{76}$Br, $^{123}$I, $^{124}$I, $^{125}$I, $^{131}$I, $^{67/68}$Ga, $^{89}$Zr, $^{99}$mTc, $^{111}$In, $^{61/62/64}$Cu, $^{67}$Cu, $^{89}$Sr, $^{90}$Y, $^{177}$Lu, $^{186}$Re, $^{165}$Dy, $^{166}$Ho, $^{211}$At and $^{213}$Bi.

In a particular aspect, the label is a fluorescent moiety.

Fluorescent moieties used as labels to generate a fluorescently labeled composition of the present invention can be any of numerous fluorophores including, but not limited to, those described in Haughland, R. P., The Handbook, A Guide to Fluorescent Probes and Labeling Technologies, 10th Ed., 2005; Lakowicz, J. R., Principles of Fluorescence Spectroscopy, Springer, 3rd ed., 2006; 4-acetamido-4'-isothiocyanatostilbene-2,2'disulfonic acid; acridine and derivatives such as acridine and acridine isothiocyanate; 4-amino-N-[3-vinylsulfonyl)phenyl]naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarin and derivatives such as coumarin, 7-amino-4-methylcoumarin (AMC, Coumarin 120), 7-amino-4-trifluoromethylcouluarin (Coumaran 151); cyanosine; DAPOXYL sulfonyl chloride; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylaminolnaphthalene-1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-anminoethyl) amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), hexachlorofluorescenin, S-(4, 6-dichlorotriazin-2-yl)aminofluorescein (DTAF), 2',7'-dimethoxy-4',5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino] ethyl}amino)naphthalene-1-sulfonic acid), Malachite Green isothiocyanate; 4-methylumbelliferone; orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron™, Brilliant Red 3B-A); rhodamine and derivatives such as 6-carboxy-X-rhodamine (ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N',N-tetramethyl-carboxyrhodamine (TAMRA); tetramethyl rhodamine; tetramethyl rhodamine isothiocyanate (TRITC); riboflavin; rosolic acid and terbium chelate derivatives.

Labeled compositions and precursor compositions according to aspects of the present invention are optionally derivatives, salts, hydrates, amides or esters of labeled compositions and precursor compositions shown or described herein. The term "derivative" as used herein refers to a labeled composition or precursor composition that is modified compared to a reference labeled composition or precursor composition and which has similar or improved bioactivity compared to the reference labeled composition or precursor composition.

Methods of Aiding in Diagnosis and/or Treatment

Methods of aiding in diagnosis and/or treatment of one or more conditions characterized by upregulation of one or more galectins are provided according to aspects of the present invention.

The term "upregulation" as used herein refers to an increased level of one or more galectins. According aspects of the present invention, the term "upregulation" refers to an increased level of galectin-1 and/or galectin-3.

Conditions characterized by upregulation of one or more galectins are exemplified by cancer, heart failure (i.e., myocardial infarction), infectious processes, such as HIV, and various other autoimmune and inflammatory processes, as well as in fibrotic tissues associated with different diseases (i.e., idiopathic pulmonary fibrosis, liver cirrhosis).

Methods of aiding in diagnosis and/or treatment of one or more conditions characterized by upregulation of one or more galectins include assaying one or more galectins with a labeled composition described or shown herein under conditions to form a complex of the labeled composition and the one or more galectins. A signal emanating from the labeled composition in the complex is detected by a suitable imaging modality such as positron emission tomography, fluorescence imaging, and the like which is indicative of the complex of the labeled composition and the one or more galectins. The signal is compared to an appropriate control to determine the level of the one or more galectins detected.

According to aspects of methods of aiding in diagnosis and/or treatment of one or more conditions characterized by upregulation of one or more galectins according to the present invention, the labeled composition includes a radionuclide and detecting a signal emanating from the labeled composition in the complex is achieved by PET, SPECT or scintigraphic imaging.

Optionally, the labeled composition comprises a fluorophore and detecting the signal including fluorescence imaging or photoacoustic imaging.

Methods of aiding in diagnosis and/or treatment of one or more conditions characterized by upregulation of one or more galectins are performed by assaying one or more galectins in a biological sample obtained from a subject having or suspected of having a condition characterized by upregulation of one or more galectins according to aspects of the present invention such as by a radioligand binding assay, fluorescent ligand binding assay, and the like.

Methods of aiding in diagnosis and/or treatment of one or more conditions characterized by upregulation of one or more galectins are optionally performed by assaying one or more galectins in a subject having or suspected of having a condition characterized by upregulation of one or more galectins according to aspects of the present invention.

For example, the subject has or is suspected of having cancer, heart failure, an infection, an HIV infection, a pathological autoimmune condition, a disease manifesting by fibrosis, and/or a pathological inflammatory condition.

Optionally, the galectin assayed is galectin-1 and/or galectin-3.

Controls are well-known in the art and one of skill in the art would readily recognize an appropriate control and be able to determine an appropriate control for a method of the present invention with no more than routine experimentation.

In one aspect, a control is a reference level of one or more galectins in a sample of the same type. The reference level may be, for example, a known level typical for a subject of similar age, gender or condition. In another aspect, the reference level is a level determined according to a method of the present invention at a first time point. The first time point may be prior to a medical treatment such that assaying one or more galectins according to the present invention provides information about efficacy of the treatment. Thus, for example, a decrease in the one or more galectins after a medical treatment to treat a condition characterized by upregulation of one or more galectins compared to the level of the one or more galectins prior to the medical treatment is indicative of efficacy of the medical treatment.

The control level of the one or more galectins may be previously determined and stored in a print or electronic medium for recall and comparison to an assayed level of the one or more galectins according to aspects of methods aiding in diagnosis and/or treatment of one or more conditions characterized by upregulation of one or more galectins of the present invention.

Galectin-1 and/or galectin-3 are upregulated in conditions, including fibrosis of lungs (e.g. idiopathic pulmonary fibrosis, IPF; chronic obstructive pulmonary disease, COPD), liver (e.g. cirrhosis), kidney (renal fibrosis); 2) myocardial infarction; 3) various cancers (e.g. breast, prostate, brain, and others); autoimmune diseases (e.g., rheumatoid arthritis, lupus, and the like). Thus, labeled compositions according to the present invention are useful as diagnostic imaging agents that enable quantitative visualization of galectin-1 and/or galectin-3 expression levels in affected organs and tissues and inhibitors of galectin-1 and/or galectin-3 function for therapy of these and other such diseases.

According to aspects of the present invention, labeled compositions are used to assay galectin 1 and/or galectin-3 for diagnostic imaging of organ and tissue fibrosis.

According to aspects of the present invention, labeled compositions are used to assay galectin 1 and/or galectin-3 for selection of patients for inclusion into the clinical trials assessing inhibitors of galectin 1 and/or galectin-3, based on the expression levels of galectin 1 and/or galectin-3 at sites of pathological/disease processes.

According to aspects of the present invention, labeled compositions are used to assay galectin 1 and/or galectin-3 to predict responsiveness of patients to therapy with inhibitors of galectin 1 and/or galectin-3.

According to aspects of the present invention, labeled compositions are used to assay galectin 1 and/or galectin-3 in micro-dosing clinical studies to assess the pharmacokinetics, metabolism, biodistribution, and targeting of pathological/disease processes (e.g. fibrotic tissue, infarction, cancer, inflammation, and others). According to particular aspects of the present invention, PET/CT imaging with a labeled composition of the present invention provides information about the pharmacokinetics and delivery of a corresponding non-labeled drug to an affected tissue in a subject and allows determination of how much of the non-labeled drug reaches its target, how much and where does the non-labeled drug accumulate, how long does the non-labeled drug remain at the target and what is the biodistribution of the labeled composition, indicative of the biodistribution of the non-labeled drug.

Pharmaceutical Compositions

Pharmaceutical compositions according to aspects of the present invention include a labeled composition described or shown herein and a pharmaceutically acceptable carrier.

Pharmaceutically acceptable carriers and formulation of pharmaceutical compositions are known in the art, illustratively including, but not limited to, as described in Remington: The Science and Practice of Pharmacy, $21^{st}$ Ed., Lippincott, Williams & Wilkins, Philadelphia, Pa., 2006; and Allen, L. V. et al., Ansel's Pharmaceutical Dosage Forms and Drug Delivery Systems, $8^{th}$ Ed., Lippincott, Williams & Wilkins, Philadelphia, Pa., 2005.

Pharmaceutical compositions suitable for delivery to a subject may be prepared in various forms illustratively including physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

Solid dosage forms for oral administration include capsules, tablets, pills, powders, and granules. In such solid dosage forms, one or more compositions described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Compositions for delivery by nasal and/or pulmonary routes e.g. by inhalation or insufflation include solutions and suspensions in a pharmaceutically acceptable carrier, such as liquids, aerosols or powders.

Advantageously, a pharmaceutical composition according to aspects of the present invention is formulated to achieve lipid-solubility and/or aqueous-solubility.

In particular aspects, a pharmaceutically acceptable carrier is a particulate carrier such as lipid particles including liposomes, micelles, unilamellar or multilamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

Compositions are optionally formulated for inhalation, such as aerosole formulations. Aerosol formulations include pressurized or non-pressurized inhalant carriers.

A particulate carrier is typically formulated such that particles have an average particle size in the range of about 1 nm-10 microns. In particular aspects, a particulate carrier is formulated such that particles have an average particle size in the range of about 1 nm-100 nm.

A pharmaceutical composition according to the present invention is suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

Administration

Subjects are identified as having, or at risk of having, a disease or condition associated with upregulation of galectins using various medical and diagnostic methods, including measurements of galectins in blood, serum, plasma, saliva, sputum, urine, biopsy material and other biological samples containing or suspected of containing one or more galectins.

According to aspects of the present invention, subjects are identified as having, or at risk of having, a disease or condition associated with upregulation of galectin-1 and/or galectin-3 using various medical and diagnostic methods, including measurements of galectin-1 and/or galectin-3 in blood, serum, plasma, saliva, sputum, urine, biopsy material and other biological samples containing or suspected of containing galectin-1 and/or galectin-3.

The term "subject" refers to an individual in which galectin imaging is desirable using compositions of the present invention and generally includes mammals and birds, such as, but not limited to, humans, other primates, cats, dogs, cows, horses, rodents, pigs, sheep, goats and poultry.

An inventive composition may be administered to a subject as a single dose for a single study or repetitively, such as for monitoring galectin levels and disease status, i.e., for monitoring therapeutic efficacy.

An effective amount of a pharmaceutical composition according to the present invention will vary depending on the particular pharmaceutical composition used, the imaging modality to be used, the species of the subject, the age and sex of the subject and the general physical characteristics of the subject to be treated. One of skill in the art could determine an effective amount in view of these and other considerations typical in the practice of medical and diagnostic imaging. In general it is contemplated that an effective amount would be in the range of about 0.0001 mg/kg-100 mg/kg body weight, optionally in the range of about 0.01-10 mg/kg, and further optionally in the range of about 0.1-5 mg/kg. The amount of the composition administered will generally include an amount of a labeled composition sufficient for imaging by a selected imaging methodology. For nuclear medical imaging an amount in the range of 0.001-1 millicuries (mCi)/kg body weight, 0.01-0.75 mCi/kg body weight, 0.05-0.5 mCi/kg body weight or 0.11-0.25 mCi/kg body weight is generally administered in one or more doses, although more or less can be administered if necessary.

Detection

Detection of the detectable signal is accomplished using an appropriate imaging method. Any detection method or system operable to detect a labeled composition can be used in methods according to embodiments of the present invention and such appropriate detection methods and systems are well-known in the art. For example, where the labeled composition is labeled with a radiolabel, a radiation detection method is used, such as Positron Emission Tomography (PET), single-photon emission computed tomography (SPECT) or scintigraphic imaging (where the composition includes a chelator and associated radiolabel). For PET, SPECT or scintigraphic detection, the radiolabel is any of various positron emitting metal ions used in PET and SPECT or scintigraphic imaging methods such as $^{18}$F, $^{76}$Br, $^{123}$I, $^{124}$I, $^{125}$I, $^{131}$I, $^{67/68}$Ga, $^{89}$Zr, $^{99}$mTc, $^{111}$In and $^{61/62/64}$Cu. Combinations of imaging techniques are optionally combined. PET imaging is optionally combined with computed tomography (CT) imaging or magnetic resonance imaging (MRI).

Where the labeled composition is labeled with a fluorescent label, a fluorescence detection method is used. A signal from a fluorescently labeled composition is detected, for example, using a light source capable of emitting light of an appropriate wavelength. The fluorescent label then emits light detectable optically, such as by eye or using a fluorescence detector.

Galectins are detected in vitro, such as in solution or in a cell, according to aspects of the present invention by contacting the solution or cell with a labeled composition under conditions which permit binding of the labeled composition and the galectin, and then detecting a detectable signal of the labeled composition in a complex of the labeled composition and the galectin. Such cells can be cell lines, primary cells isolated from an organism or cells present in an explanted tissue or tumor sample, such as a biopsy tumor sample.

Galectins are detected in vivo according to aspects of the present invention by administration of a labeled composition to a subject under conditions which permit binding of the labeled composition and the galectin, and then detecting a detectable signal of the labeled composition in a complex of the labeled composition and the galectin in the subject.

Conditions which permit binding of the labeled composition and the galectin in vitro and in vivo are physiological conditions according to aspects of the present invention, including, physiological temperature and pH. In vitro conditions can include contacting the labeled composition and the galectin in a buffer.

Commercial Packages

Commercial packages are provided according to aspects of the present invention including a labeled composition and/or precursor composition described herein; or a derivative, salt, hydrate, amide or ester thereof. One or more auxiliary components are optionally included in commercial packages of the present invention, such as a pharmaceutically acceptable carrier exemplified by a buffer, diluent or a reconstituting agent.

Embodiments of inventive compositions and methods are illustrated in the following examples. These examples are provided for illustrative purposes and are not considered limitations on the scope of inventive compositions and methods.

EXAMPLES

Example 1

Scheme 1a shows a method for preparation of bis-(3-azido-2,4,6-tri-O-acetyl-β-D-galactopyranosyl)sulfane (XXIX), which is the starting material for the symmetrical "cold" standards (X) used for radiosynthesis and cell uptake studies. Synthesis of 2,4,6-tri-O-acetyl-3-azido-α-D-galactopyranosyl bromide (XXVII). The solution of tetra-O-acetyl-3-azido-D-galactopyranose (XXVI) (1 g, 2.68 mmol) in dry DCM (5 mL) was added dropwise under vigorous stirring to the titanium tetrabromide (0.59 g, 1.61 mmol) solution in dry DCM (10 mL) with catalytic amount of glacial acetic acid. The reaction mixture was left for 1.5 h under microwave irradiation at 55° C., then was diluted with DCM, washed with saturated NaHCO$_3$ solution two times, water and dried under Na$_2$SO$_4$ for 3 h. Organic layer was evaporated under reduced pressure, and purified with column chromatography (SiO$_2$, Hexane:EtOAc, 4:1). Yield is 75%. R$_f$=0.65 (Hexane:EtOAc, 1:1, v/v).

NMR and HRMS data correspond to those described in van Scherpenzeel, M., et al., *Chem Bio Chem*. 2009, 10, 1724-1733.

Synthesis of triisopropylsilyl 2,4,6-tri-O-acetyl-3-azido-1-thio-β-D-galactopyranoside (XXVIII). TIPSSH (0.33 mL, 1.52 mmol) was added dropwise at 0° C. to the solution of bromide (XXVII) (500 mg, 1.27 mmol) in dry and degassed acetonitrile (10 mL) with anhydrous K$_2$CO$_3$ (526 mg, 3.81 mmol). The reaction mixture was stirred for 30 min at 0° C., then 3 h at room temperature. The solvent was evaporated; the residue was purified with column chromatography (SiO$_2$, Hexane:EtOAc, 4:1) gave tri-isopropylsilyl galactopyranoside XXVIII (570 mg, 89%). R$_f$=0.6 (Hexane:EtOAc, 2:1, v/v).

NMR and HRMS data correspond to those described in S. Mandal and U. J. Nilsson, *Org. Biomol. Chem.*, 2014, 12, 4816-4819.

Synthesis of bis-(3-azido-2,4,6-tri-O-acetyl-β-D-galactopyranosyl)sulfane (XXIX). TBAF (0.46 mL, 0.46 mmol) was added dropwise to the solution of tri-isopropylsilyl galactopyranoside (XXVIII) (230 mg, 0.46 mmol) and bromide (XXVII) (150 mg, 0.38 mmol) in dry and degassed acetonitrile (10 mL) at −10° C. The reaction mixture was stirred 15 min at −10° C., then 30 min at room temperature. The solvent was evaporated and the residue was purified with column chromatography (SiO$_2$, Hexane:EtOAc, 4:1) gave bis-(3-D-galactopyranosyl) sulfane (XXIX) (183 mg, 68%). R$_f$=0.4 (Hexane:EtOAc, 1:1, v/v).

NMR and HRMS data correspond to those described in S. Mandal and U. J. Nilsson, *Org. Biomol. Chem.*, 2014, 12, 4816-4819.

Synthesis of bis-{2,4,6-tri-O-acetyl-3-[4-(4-fluorophenyl)-1H-1,2,3-triazol-1-yl]-β-D-galactopyranosyl)sulfane (Xa). Compound (XXIX) (528 mg, 0.80 mmol), sodium ascorbate (40 mg, 0.24 mmol), CuSO$_4$ (20 mg, 0.15 mmol) and 4-fluorophenylacetylene (250 mg, 2.09 mmol) were dissolved in a mixture of DMF:water 5:1 (7 mL). The reaction mixture was heated under microwave irradiation to 85° C. for 1.5 h. The mixture was concentrated under reduced pressure, dissolved in DCM, and then filtered through small amount of silica. Silica gel was washed with Hexane:EtOAc (1:1). The mixture of solvents was evaporated to dryness and the residue was purified with column chromatography (SiO$_2$, Hexane:EtOAc, 1:1). Yield is 70-85%. R$_f$=0.1 (Hexane:EtOAc, 1:1, v/v)

$^1$H NMR (500 MHz, CDCl$_3$) δ 7.88 (s, 2H), 7.81 (dd, J=8.7, 5.3 Hz, 4H), 7.12 (t, J=8.7 Hz, 4H), 5.84 (dd, J=10.7, 10.0 Hz, 2H), 5.64 (d, J=2.8 Hz, 2H), 5.19 (dd, J=11.1, 3.2 Hz, 2H), 4.96 (d, J=9.7 Hz, 2H), 4.40 (dd, J=11.5, 6.7 Hz, 2H), 4.18 (t, J=6.2 Hz, 2H), 4.10 (dd, J=11.5, 5.7 Hz, 2H), 2.12 (s, 6H), 2.11 (s, 6H), 1.93 (s, 6H). $^{13}$C NMR (125 MHz, CDCl$_3$) δ 170.9, 169.6, 169.0, 163.0 (d, J=248.0 Hz), 147.4, 127.6 (d, J=8.2 Hz), 126.4, 118.4, 116.1 (d, J=21.8 Hz), 82.6, 76.3, 69.1, 66.8, 63.3, 61.8, 21.0, 20.7, 20.6. HRMS (+ESI-TOF) m/z for $C_{40}H_{42}F_2N_6O_{14}S$ [M+H]$^+$ calcd 901.2526, found 901.2502.

Synthesis and purification of bis-{2,4,6-tri-O-acetyl-3-[4-(3-fluorophenyl)-1H-1,2,3-triazol-1-yl]-β-D-galactopyranosyl)sulfane (Xb) was done according to procedure described above for (Xa).

NMR and HRMS data correspond to the earlier described in US 2014/0121179.

Synthesis of bis-{3-deoxy-3-[4-(4-fluorophenyl)-1H-1,2,3-triazol-1-yl]-β-D-galactopyranosyl)sulfane (Xc). The solution of sodium methoxide (1 equiv) in methanol was added to the solution of peracetylated galactopyranosylsulfane (Xa) in methanol at room temperature. The progress of deprotection was monitored with silica and C18 TLC, and then the reaction mixture was neutralized with DOWEX resin. The resin was filtered out, washed with methanol. Solvent was evaporated to dryness under reduced pressure to give (Xc) in almost quantitative yield. $R_f$=0.25-0.30 (MeCN: Water, 3:7, v/v, C18).

$^1$H NMR (600 MHz, DMSO-dd/D$_2$O) δ 8.51 (s, 2H), 7.86 (t, J=5.9 Hz, 4H), 7.24 (t, J=8.2 Hz, 4H), 4.89 (d, J=9.4 Hz, 2H), 4.83 (d, J=10.5 Hz, 2H), 4.27 (t, J=9.9 Hz, 2H), 3.95 (d, J=2.6 Hz, 2H), 3.73 (t, J=6.2 Hz, 2H), 3.53 (m, 4H). $^{13}$C NMR (151 MHz, DMSO-d$_6$/D$_2$O) δ 163.1, 161.4, 145.4, 127.8 (d, J=1.8 Hz), 127.7 (d, J=8.1 Hz), 121.5, 116.4 (d, J=21.6 Hz), 84.4, 79.8, 68.1, 67.3, 67.1, 60.8. $^{19}$F NMR (376 MHz, DMSO-d$_6$/D$_2$O) δ −113.98−−114.13 (m). HRMS (+ESI-TOF) m/z for $C_{28}H_{30}F_2N_6O_8S$ [M+H]$^+$ calcd 649.1814, found 649.1825.

Synthesis of bis-{3-deoxy-3-[4-(3-fluorophenyl)-1H-1,2,3-triazol-1-yl]-β-D-galactopyranosyl)sulfane (Xd, TD139) was done according to procedure described above for (Xc).

NMR and HRMS data correspond to those described in US 2014/0121179.

Example 2

Scheme 1b shows a method of synthesis of precursors (XVI, XVII) used in synthesis of both symmetrical and asymmetrical radiolabeled compounds.

Synthesis of 1,2,4,6-tetra-O-acetyl-3-[4-(4-fluorophenyl)-1H-1,2,3-triazol-1-yl]-D-galactopyranoside (XXXa) is shown in Scheme 1b. Compound (XXVI) (300 mg, 0.80 mmol), sodium ascorbate (40 mg, 0.24 mmol), CuSO$_4$ (20 mg, 0.15 mmol) and 3-fluorophenylacetylene (115 mg, 0.96 mmol) were dissolved in a mixture of DMF:water 5:1 (7 mL). The reaction mixture was heated under microwave irradiation to 85° C. for 1.5 h. The mixture was concentrated under reduced pressure, dissolved in DCM, and then filtered through small amount of silica. Silica gel was washed with Hexane:EtOAc (1:1). The mixture of solvents was evaporated to dryness. The resulting residue was introduced to the next step without further purification. $R_f$=0.50 (Hexane: EtOAc, 1:1, v/v).

Synthesis of 1,2,4,6-tetra-O-acetyl-3-[4-(3-fluorophenyl)-1H-1,2,3-triazol-1-yl]-D-galactopyranoside (XXXb) was done according to procedure described above for (XXXa).

Synthesis of 2,4,6-tri-O-acetyl-3-[4-(4-fluorophenyl)-1H-1,2,3-triazol-1-yl]-D-galactopyranosyl bromide (XXXIa). The solution of the clicked monomer (XXXa) (0.5 g, 1.01 mmol) in dry DCM (5 mL) was added dropwise under vigorous stirring to the titanium tetrabromide (0.24 g, 0.65 mmol) solution in dry DCM (10 mL) with catalytic amount of glacial acetic acid. The reaction mixture was left for 1.5 h under microwave irradiation at 55° C., then was diluted with DCM, washed with saturated NaHCO$_3$ solution two times, water and dried under Na$_2$SO$_4$ for 3 h. Organic layer was evaporated under reduced pressure, and the residue was purified with column chromatography (SiO$_2$, Hexane:EtOAc, 4:1). Yield is 50-60%. $R_f$=0.8 (Hexane:EtOAc, 1:1, v/v)

$^1$H NMR (600 MHz, CDCl$_3$) δ 7.77 (m, 3H), 7.11 (t, J=8.6 Hz, 2H), 6.88 (d, J=3.7 Hz, 1H), 5.80 (dd, J=11.3, 3.8 Hz, 1H), 5.64 (d, J=1.5 Hz, 1H), 5.34 (dd, J=11.4, 2.9 Hz, 1H), 4.64 (t, J=6.4 Hz, 1H), 4.23 (dd, J=11.6, 6.3 Hz, 1H), 4.13 (dd, J=11.6, 6.7 Hz, 1H), 2.06 (s, 6H), 1.95 (s, 3H). $^{13}$C NMR (150 MHz, CDCl$_3$) δ 170.4, 169.7, 169.2, 163.0 (d, J=247.9 Hz), 147.2, 127.6 (d, J=8.2 Hz), 126.3 (d, J=3.1 Hz), 119.4, 116.1 (d, J=21.8 Hz), 88.7, 71.5, 67.9, 67.0, 61.0, 58.9, 20.7, 20.6, 20.5. HRMS (+ESI-TOF) m/z for $C_{20}H_{21}BrFN_3O_7$ [M+H]$^+$ calcd 514.0625, found 514.1011.

Synthesis of 2,4,6-tri-O-acetyl-3-[4-(3-fluorophenyl)-1H-1,2,3-triazol-1-yl]-D-galactopyranosyl bromide (XXXIb) was done according to procedure described above for (XXXIa).

$^1$H NMR (400 MHz, CDCl$_3$) δ 7.81 (s, 1H), 7.59-7.50 (m, 2H), 7.39 (td, J=8.0, 6.0 Hz, 1H), 7.04 (td, J=8.4, 1.8 Hz, 1H), 6.88 (d, J=3.8 Hz, 1H), 5.81 (dd, J=11.4, 3.8 Hz, 1H), 5.64 (d, J=1.8 Hz, 1H), 5.34 (dd, J=11.4, 3.0 Hz, 1H), 4.64 (t, J=6.5 Hz, 1H), 4.24 (dd, J=11.6, 6.3 Hz, 1H), 4.13 (dd, J=11.6, 6.7 Hz, 1H), 2.07 (s, 3H), 2.06 (s, 3H), 1.95 (s, 3H). $^{13}$C NMR (150 MHz, CDCl$_3$) δ 170.4, 169.7, 169.2, 163.3 (d, J=246.1 Hz), 147.0, 132.2 (d, J=8.3 Hz), 130.7 (d, J=8.4 Hz), 121.5, 120.1, 115.5 (d, J=21.3 Hz), 112.9 (d, J=23.1 Hz), 88.67, 71.47, 67.88, 66.99, 61.00, 58.95, 20.75, 20.62, 20.50. $^{19}$F NMR (376 MHz, CDCl$_3$) δ −112.36−−112.45 (m). HRMS (+ESI-TOF) m/z for $C_{20}H_{21}BrFN_3O_7$[M+H]$^+$ calcd 514.0625, found 514.0627.

Synthesis of (XVIa) was done according to procedure described above for (X). Yield is 50-60%.

$^1$H NMR (600 MHz, CDCl$_3$) δ 7.77 (s, 1H), 7.75 (dd, J=8.7, 5.3 Hz, 2H), 7.11 (t, J=8.6 Hz, 2H), 5.73 (t, J=10.4 Hz, 1H), 5.62 (d, J=2.9 Hz, 1H), 5.50 (d, J=3.0 Hz, 1H), 5.26-5.14 (m, 2H), 4.97 (d, J=9.7 Hz, 1H), 4.84 (d, J=10.0 Hz, 1H), 4.25-4.05 (m, 5H), 3.90 (t, J=6.4 Hz, 1H), 3.68 (dd, J=10.1, 3.3 Hz, 1H), 2.19 (s, 3H), 2.16 (s, 3H), 2.09 (s, 3H), 2.07 (s, 3H), 2.06 (s, 3H), 1.91 (s, 3H). $^{13}$C NMR, $^{19}$F, HRMS (+ESI-TOF) m/z for $C_{32}H_{37}FN_6O_{14}S$ [M+H]$^+$ calcd 781.2151, found 781.2146.

Synthesis of (XVIIb) was done according to procedure described above for (X). Yield is 50-60%.

$^1$H NMR (600 MHz, CDCl$_3$) δ 7.83 (s, 1H), 7.53 (t, J=10.2 Hz, 2H), 7.38 (dd, J=13.8, 7.9 Hz, 1H), 7.03 (td, J=8.4, 1.8 Hz, 1H), 5.73 (t, J=10.4 Hz, 1H), 5.62 (d, J=2.8 Hz, 1H), 5.50 (d, J=2.8 Hz, 1H), 5.24-5.17 (m, 2H), 4.98 (d, J=9.7 Hz, 1H), 4.84 (d, J=10.0 Hz, 1H), 4.22-4.08 (m, 5H), 3.91 (t, J=6.4 Hz, 1H), 3.68 (dd, J=10.1, 3.3 Hz, 1H), 2.18 (s, 3H), 2.16 (s, 3H), 2.09 (s, 3H), 2.07 (s, 3H), 2.06 (s, 3H), 1.91 (s, 3H). $^{13}$C NMR (151 MHz, CDCl$_3$) δ 170.6, 170.4, 170.0, 169.7, 169.5, 168.9, 163.3 (d, J=245.9 Hz), 147.1, 132.3 (d, J=8.2 Hz), 130.7 (d, J=8.4 Hz), 121.4, 118.9, 115.5 (d, J=21.2 Hz), 112.9 (d, J=23.1 Hz), 82.3, 81.7, 75.8, 68.8, 68.6, 67.8, 66.5, 63.2, 63.0, 61.7, 61.5, 20.9, 20.9, 20.8, 20.7, 20.6. $^{19}$F NMR (376 MHz, CDCl$_3$) δ −112.33−−112.43 (m). HRMS (+ESI-TOF) m/z for $C_{32}H_{37}FN_6O_{14}S$ [M+H]$^+$ calcd 781.2151, found 781.2162.

Example 3

Certain precursors were prepared as shown in Schemes 2a and 2b following a similar previously published method described in Hausner, et al., J. of Med. Chem., 2008, Vol. 51, No. 19, p 5901-5904; and Marik, et al., Tetrahedron Letters 47 (2006) 6681-6684.

Scheme 2a shows synthesis of a para-precursor used in methods of synthesis of radiolabeled compositions according to aspects of the present invention. Scheme 2b shows synthesis of a meta-precursor used in methods of synthesis of radiolabeled compositions according to aspects of the present invention.

Scheme 3a shows synthesis of a 4-$^{18}$F-phenylacetylene precursor used in methods of synthesis of radiolabeled compositions according to aspects of the present invention. Scheme 3b shows synthesis of a 3-$^{18}$F-phenylacetylene precursor used in methods of synthesis of radiolabeled compositions according to aspects of the present invention. Scheme 3c shows synthesis of a 5-$^{18}$F-pentyne used in methods of synthesis of radiolabeled compositions according to aspects of the present invention.

The radiolabeled precursors shown in Schemes 3a, 3b and 3c were coupled with several 3-substituted-3'-azide-thiodigalactosides using click chemistry as shown in Schemes 4a, 4b and 4c. Semi-prep HPLC purification was performed, then the fraction that corresponds to the product was collected and the identity of the product was confirmed by co-elution with the cold standard. The acetyl groups were removed under basic conditions and the produced fluoropentyl, 3- and 4-fluorophenyl thiogalactosides were then formulated for cell uptake studies or animal injection.

Radiosynthesis of Thiodigalactosides

General

The K$^{18}$F/cryptofix solution in acetonitrile was purchased from the Children's Hospital of Michigan. The solution was transferred to a v-vial and the acetonitrile was removed under a stream of argon.

Example 4

Radiosynthesis of 4-$^{18}$F-fluorophenylacetylene (XXXVIII). To the dried and sealed vial contains the K$^{18}$F/cryptofix2.2.2 was added 1-10 mg (0.4 mL of DMF) of the 4-acetylene-N,N,N-trimethyl benzyl ammonium trifluoromethyl sulfonate (XXXVII). The mixture was heated at 120'C for 5 min then passed through a silica cartridge to remove the unreacted fluoride. Also, this compound could be distilled into another vial cooled between −10 to −40° C. The identity of the crude product was confirmed by co-elution with the cold standard using analytical HPLC. HPLC conditions: solvent, 65% acetonitrile/water, flow rate 1.0 mL/min. Retention time was 6.2 min.

Example 5

Radiosynthesis of 3-$^{18}$F-fluorophenylacetylene (XX). The synthesis was performed in a similar manner to the radiosynthesis of 4-$^{18}$F-fluorophenylacetylene (XXXVIII) using 3-acetylene-N,N,N-trimethyl benzyl ammonium trifluoromethyl sulfonate as precursor.

Example 6

Radiosynthesis of 5-$^{18}$F-fluoropentyne (LX). To the dried sealed vial contains the K$^{18}$F/cryptofix was added 1-10 mg (0.4 mL of DMF) of the 5-tosyl-pentyne. The mixture was heated at 120° C. for two min followed by distillation to another vial cooled to −10° C.

Typical procedures for the radiosynthesis of a [$^{18}$F]-3,3'-bis-triazolyl-thiodigalactoside derivatives using "click" chemistry:

To the crude $^{18}$F-acetylene derivative in DMF was added the 2,2',4,4',6,6'-hexa-O-acetyl-3-azido-3-deoxy-3'-substituted-3'-deoxy-1-thio-β-D-digalactopyranoside in 100 μL DMF, followed by 50 μL of 1.0 M CuSO$_4$ then, sodium ascorbate 8.0 mg in 100 μL of water was added and the mixture stirred for 10 min at 100° C. and purified by semi-prep HPLC. The pure product was hydrolyzed under basic conditions and formulated for cell uptake studies and in vivo PET animal imaging.

Example 7

Radiosynthesis of 3-(4-$^{18}$F-fluorophenyl triazolyl)-3-deoxy-3'-3-fluorophenyl triazolyl-3'-deoxy-1-thio-β-D-digalactopyranoside (VII).

This compound was prepared according to the general procedure. Semi-prep conditions: Solvent: 58% acetonitrile/water, flow rate 4.0 mL/min, R$_t$: 26.2 min.

Example 8

Radiosynthesis of 3-(3-$^{18}$F-fluorophenyl triazolyl)-3-deoxy-3'-(3-fluorophenyl triazolyl-3'-deoxy-1-thio-β-D-digalactopyranoside (VI).

This compound was prepared according to the general procedure. Semi-prep conditions: Solvent: acetonitrile/water 58/42, flow rate 4.0 mL/min, R$_t$: 26.5 min.

Example 9

Radiosynthesis of 3-(3-$^{18}$F-fluoropropyl triazolyl-3-deoxy-3'-(3-fluorophenyl triazolyl-3'-deoxy-1-thio-β-D-digalactopyranoside (VII).

This compound was prepared according to the general procedure. Semi-prep conditions: Solvent: acetonitrile/water 58/42, flow rate 4.0 mL/min, R$_t$: min 29.0 min.

Example 10

Biological characterization of selected F-18 labeled thiogalactosides for binding to different cancer cells in vitro.

The [$^{18}$F]-fluoropentyl thiodigalactoside, 3-[$^{18}$F]fluorophenyl thiodigalactoside, and 4-[$^{18}$F]fluorophenyl thiodigalactoside were synthesized as described above.

Various cancer cell lines were tested in vitro, including: a) breast carcinomas (MCF10A-derived: MCF10AT1, MCF10NeoT, MCF10DCIS; MCF10Cald1, MDA-MB-231, MDA-MB-435, SKBR3) and b) pancreatic carcinomas (MiaPaCa, Panc 1); as well as c) leukemia cell lines (HL60, Molt4). The cancer cells were grown under normal cell culture cultivation conditions (MEM with 10% FCS, glucose, in humidified atmosphere, at 37° C.).

FIGS. 14 A-C: Characterization of galectin 1 and galectin 3 expression in different cancer cell lines. Fluorescence microscopic images of galectin 1 and galectin 3 expression in MCF10-derived cancer cell lines (A). Galectin 1 and galectin 3 expression on membranes of different cancer cell lines (B). Correlation between the levels of galectin-3 expression and 3-[$^{18}$F]fluorophenyl thiodigalactoside (VI, where X is S) accumulation in corresponding cancer cell lines in vitro.

The magnitude and patterns of galectin-1 and galectin-3 levels in these cancer cells were visualized using fluorescence microscopy (FIG. 14A). Quantitative measurements of galectin-1 and galectin-3 levels on cellular membranes on these tumor cells were performed using ELISA (Abcam, CA) (FIG. 14B).

For in vitro radiotracer binding/accumulation assay, the cells were plated in 10 cm plastic Petri dishes and grown until 60-80% confluent monolayers were observed with light microscopy. The cell monolayers in Petri dishes were incubated with 14 ml of cell culture medium containing individual F-18 labeled radiotracer (0.1 uC/ml) for 30 min to achieve receptor binding equilibrium, then harvested by gentle scraping, transferred into the 15 ml conical polypropylene tubes, which were then centrifuged at 3000 rpm to obtain cell pellet; the supernatant was removed by vacuum-assisted aspiration, the top surface of the pellet was blotted by a cotton swab, the pellet frozen inside the tube by placing it on a dry ice, the frozen pellet was tapped out of the tube, placed into the pre-weighed scintillation vial and weighed to calculate the cell pellet weight; then the radioactivity concentration in cell pellet and radioactive medium sample (20 ul) was measured using gamma counter (Cobra II, Packard/Perkin-Elmer, CA). The radioactivity concentration in cell pellet was normalized by its weight (cpm/g) and divided by the radioactivity concentration in culture medium (cmp/ml), which is a measure of fold-accumulation of radiotracer on cellular membranes as a function of target receptor expression (distribution volume) (FIG. 14C). A significant linear correlation was observed between the levels of galectin- and galectin-3 expression on cellular membranes of individual cancer cell lines with levels of accumulation of radiotracers in corresponding cell lines.

These data clearly demonstrate that the level of binding (accumulation) of 3-[$^{18}$F]fluorophenyl thiodigalactoside in different cancer cells reflects the level of galectin-3 expression on the cell membranes and can be used for radioligand assay to measure the levels of galectin-3 expression in cells in vitro.

Also, these data indicate that 3-[$^{18}$F]fluorophenyl thiodigalactoside and other F-18 labeled thiodigalactoside radiotracers with similar binding characteristics to galectin-3 (with Kd in nM range) can be used for detection and quantification of galectin-3 expression in tissues in vivo using non-invasive imaging methodology such as PET.

These results show that the levels of galectin-3 levels in breast epithelial cells-derived cancer cell lines increases with progression of malignancy from benign (MCF10A) to ductal carcinoma in situ (DCIS) and invasive breast carcinoma (MDCF10Cald), whereas a reversed pattern is observed for galectin-1.

These results further show that methods and compositions for imaging of labeled galectin binding compositions, such as PET imaging with F-18 labeled thiodigalactoside radiotracers, e.g. 3-[$^{18}$F]fluorophenyl thiodigalactoside, according to aspects of the present invention are useful for differentiation of more benign vs more malignant breast lesions, as well as for image-guidance of biopsies for improvement of detection of true-positive malignant breast lesions.

Example 11

PET/CT imaging of 3-(3-[$^{18}$F]fluorophenyl triazolyl)-3-deoxy-3'-(3-fluorophenyl triazolyl)-3'-deoxy-1-thio-β-D-digalactopyranoside ([$^{18}$F]FPTDG) biodistribution kinetics in a normal rat.

Radiosynthesis

The 3-(3-[$^{18}$F]fluorophenyl triazolyl)-3-deoxy-3'-(3-fluorophenyl triazolyl-3'-deoxy-1-thio-β-D-digalactopyranoside ([$^{18}$F]FPTDG) was synthesized as described in Scheme 1a. Specifically, 1-10 mg (0.4 mL of DMF) of the 3-acetylene-N,N,N-trimethyl benzyl ammonium trifluoromethanesulfonate (precursor) was added to the dried and sealed vial containing K$^{18}$F/kryptofix2.2.2. The mixture was heated at 120° C. for 10 min then passed through a silica cartridge to remove the unreacted $^{18}$F-fluoride. The identity of the crude product, the 3-$^{18}$F-fluorophenylacetylene, was confirmed by co-elution with the cold standard using analytical HPLC. HPLC conditions: solvent, 65% acetonitrile/water, flow rate 1.0 mL/min. Retention time was 6.2 min. To the crude 3-$^{18}$F-fluorophenylacetylene in DMF, the 2,2',4,4',6,6'-hexa-O-acetyl-3-azido-3-deoxy-3'-substituted-3'-deoxy-1-thio-β-D-digalactopyranoside in 100 μL DMF was added first, followed by 50 μL of 1.0 M CuSO$_4$, then sodium ascorbate 8.0 mg in 100 μL of water and the mixture was stirred for 20 min, followed by purification by semi-preparative HPLC (solvent: 58% acetonitrile/water, flow rate 4.0 mL/min, R$_t$: 26.2 min). The purified product was de-protected by hydrolysis under basic conditions to yield 3-(3-[$^{18}$F]fluorophenyl triazolyl)-3-deoxy-3'-(3-fluorophenyl triazolyl)-3'-deoxy-1-thio-β-D-digalactopyranoside ([$^{18}$F]FPTDG) and formulated in saline for in vivo PET imaging studies.

PET/CT Imaging

Sprague-Dawley rats (males, ~250 g) were anesthetized using inhalation of 2% isoflurane in oxygen, and their body temperature maintained at 37° C. by a heating pad with a feedback temperature control. The rats were positioned inside the microPET R4 (Siemens) with the field of view covering thoraco-abdominal section and injected intravenously with 400-500 uCi of [$^{18}$F]FPTDG. Dynamic PET images were acquired in the list-mode and reconstructed using OSEM algorithm at multiple time frames post radiotracer administration (0-2, 2-4, 4-6, 6-8, 8-10, 10-20, 20-30, 30-40, 40-50, 50-60 min), followed by a whole body image that has been acquired using 3 consecutive bed positions, 5 min/bed position. Thereafter, while still fixed to the positioning bed, the rats were moved with the bed into the gantry of the INVEON SPECT/CT (Siemens) and CT images were acquired over the whole body area for attenuation correction of PET images and for production of PET/CT images. PET/CT fusion images were generated and analyzed using the AMIDE software version 1.0.4. Regions of interest were drawn over different organs and tissues and the [$^{18}$F]FPTDG-derived radioactivity concentrations quantified in Standard Uptake Values (SUV) were plotted over time. The data was analyzed using GraphPad Prism version 6 (GraphPad Prism, Inc.) and pharmacokinetic parameters of clearance were calculated by fitting the resultant time-activity curves with exponential or bi-exponential functions.

Pharmacokinetics and biodistribution of [$^{18}$F]FPTDG in rats (FIGS. 15-19).

The [$^{18}$F]FPTDG exhibited a rapid bi-exponential clearance from the blood (fast clearance half-time=0.5 min, slow clearance half-time=7.36 min; FIG. 19), which occurred predominantly via the hepatobiliary route of excretion, as evidenced by very high levels of radioactivity in the liver (FIGS. 15-18), increasing levels in duodenum and upper intestinal tract (with gradual progression of [$^{18}$F]FPTDG-derived radioactivity towards the large intestine by way of peristalsis). Liver and kidney clearance followed mono-exponential kinetics with half-times of 53 and 68 min, respectively.

Figure 15:
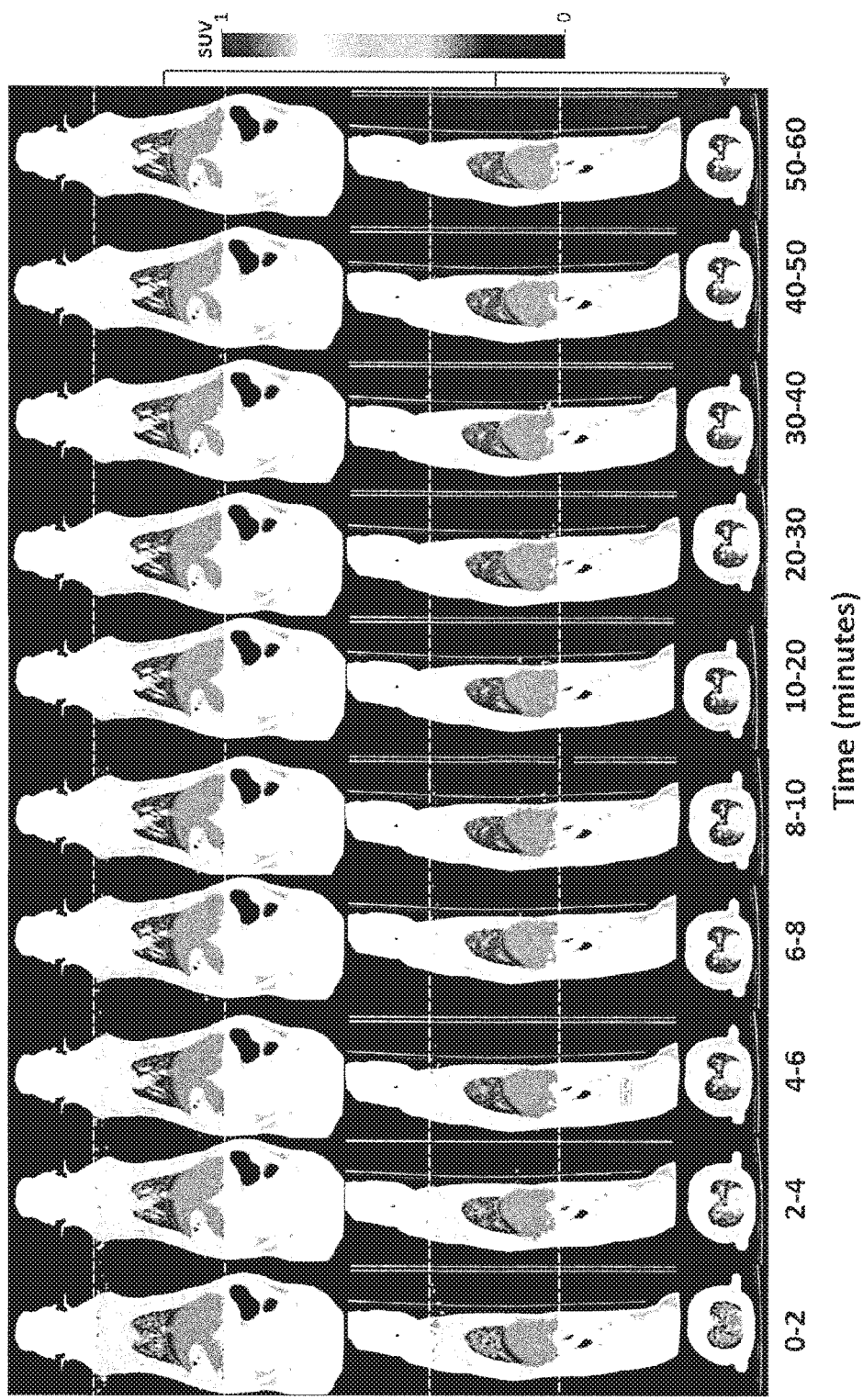
FIG. 15 is a series of dynamic PET/CT images of [18F] FPTDG localization obtained at different time intervals after intravenous administration.
Figure 16:
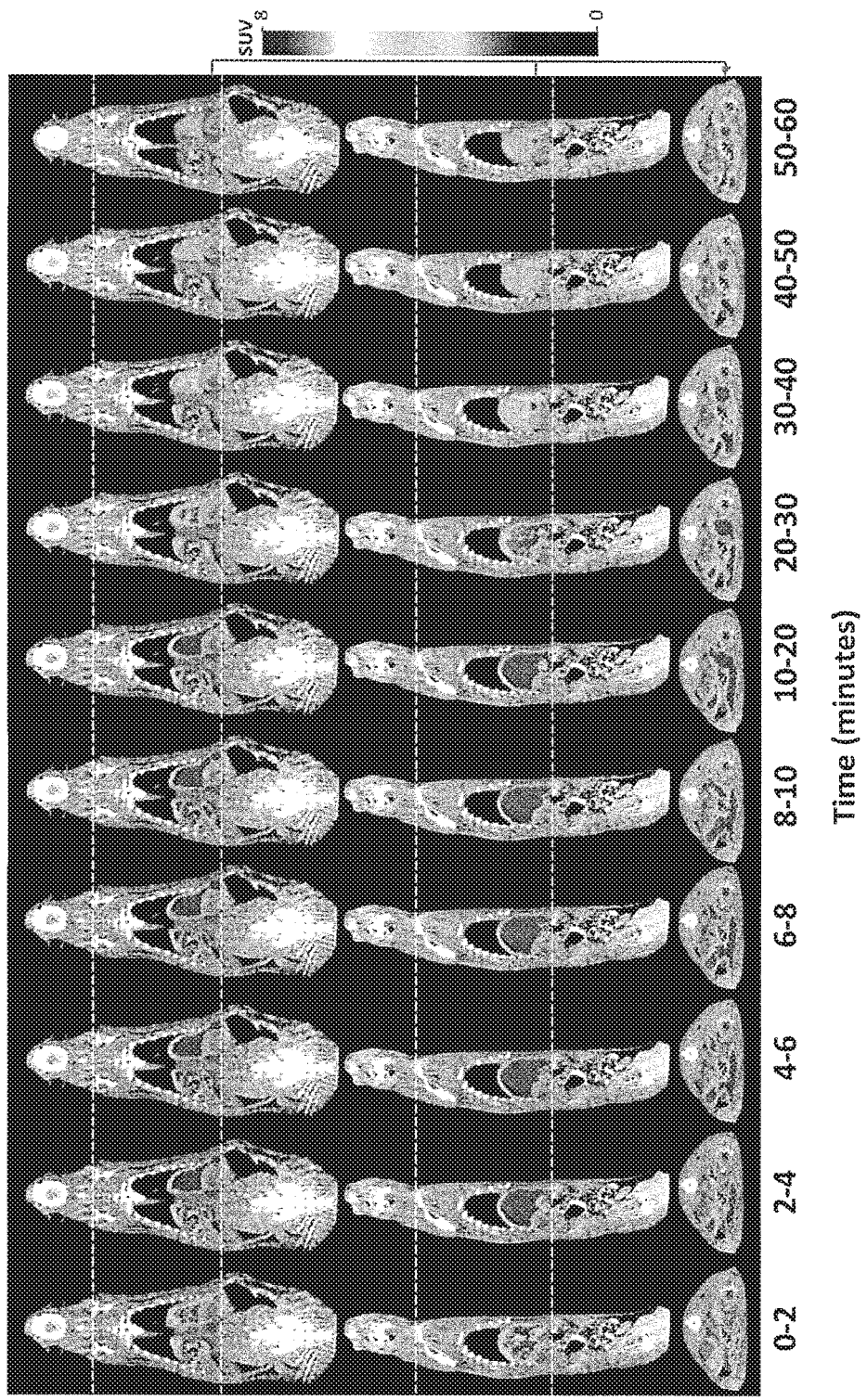
FIG. 16 is a series of dynamic PET/CT images of [18F] FPTDG localization obtained at different time intervals after intravenous administration.
Figure 17:
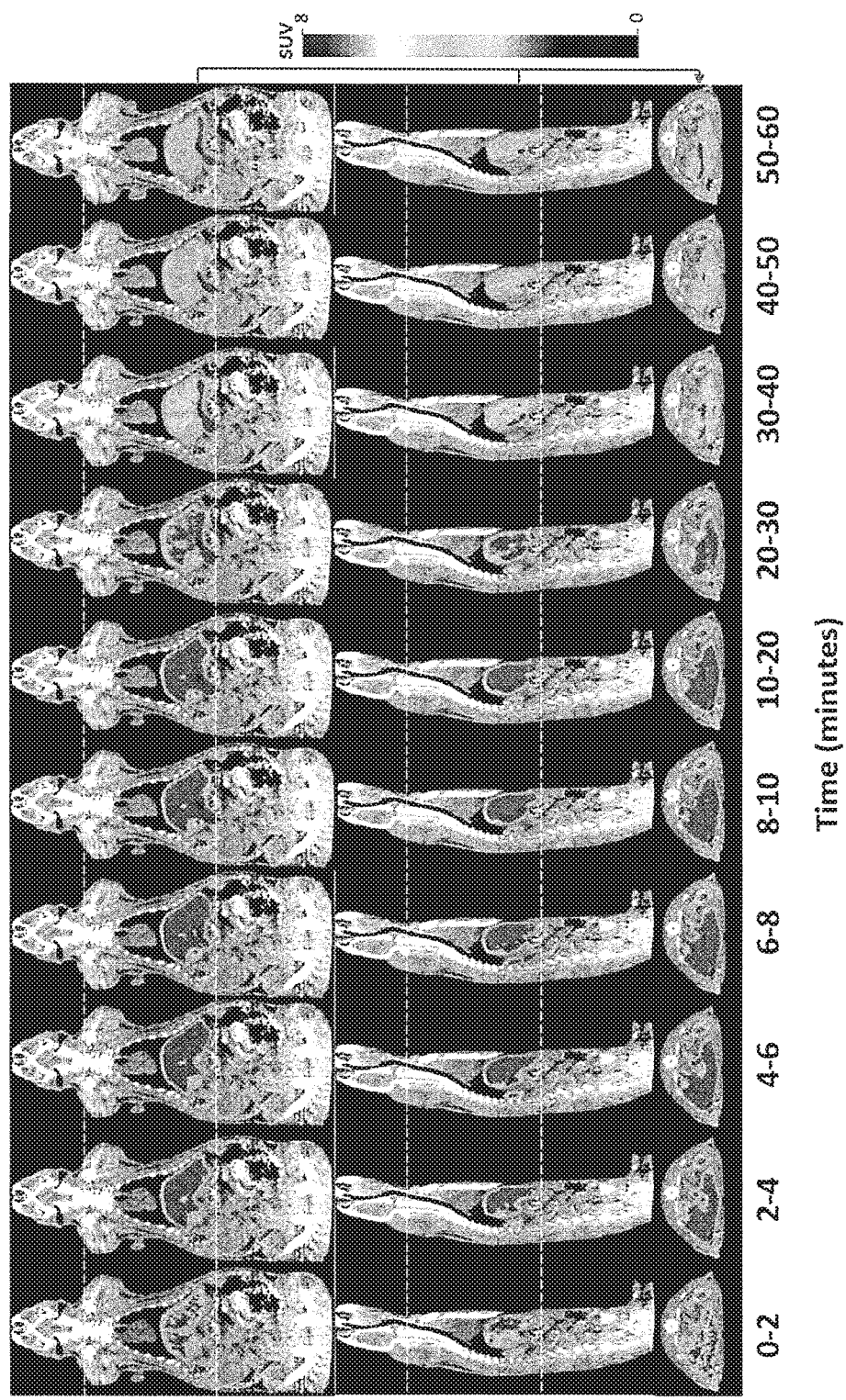
FIG. 17 is a series of dynamic PET/CT images of [18F] FPTDG localization obtained at different time intervals after intravenous administration.
Figures 18A, 18B:
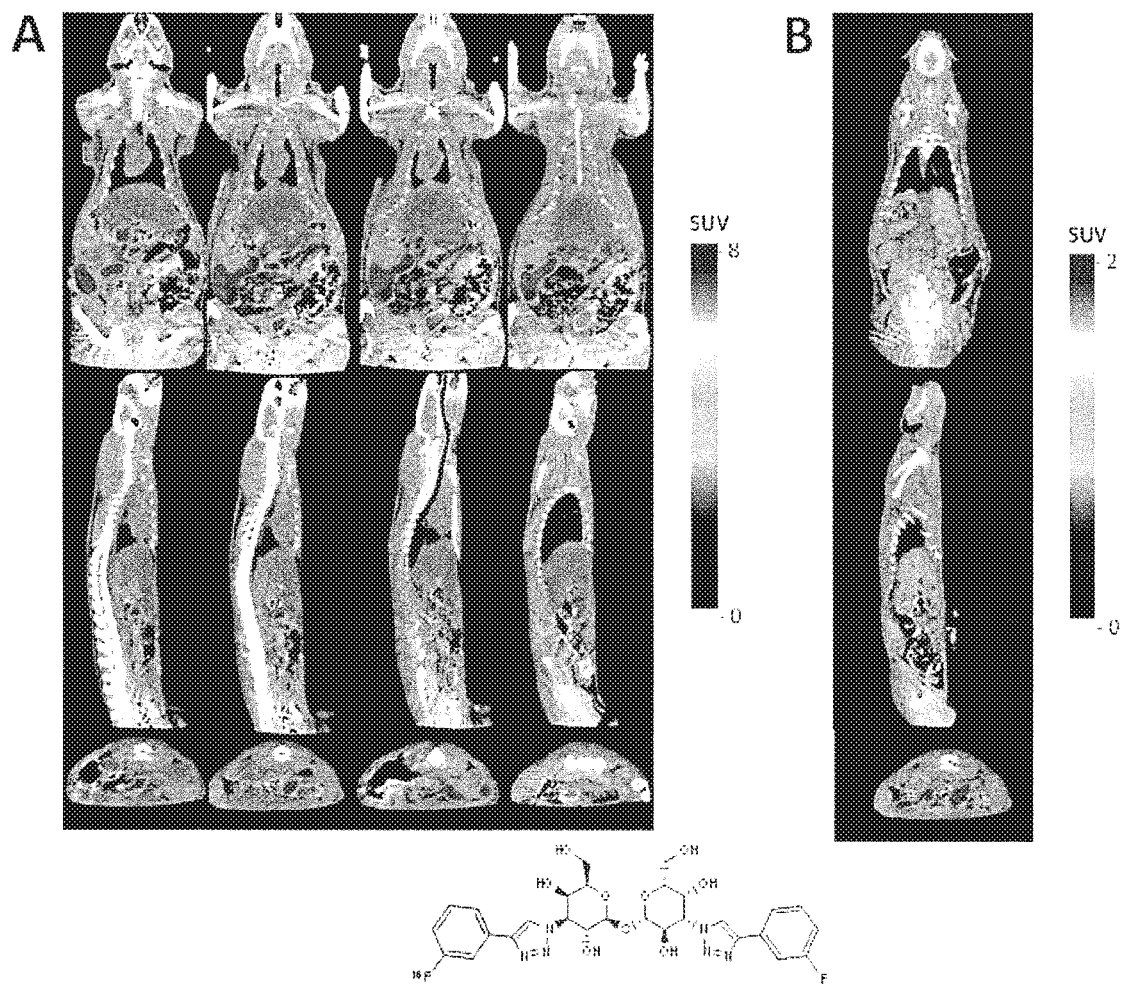
FIG. 18A is a series of PET/CT images of [18F]FPTDG localization in a rat at 75 min. after intravenous administration.
FIG. 18B is a dynamic PET/CT image of [18F]FPTDG localization after intravenous administration.

In contrast, renal clearance was insignificant, as evidenced by very low amounts of radioactivity in the bladder (FIGS. 15-18). Noteworthy, the radioactivity in the kidney was localized predominantly in the cortical region with almost no radioactivity registered in the kidney pelvis and ureters (FIG. 18). The magnitude of catabolism of [$^{18}$F] FPTDG was negligible, as evidenced by very low levels of [$^{18}$F]F2 accumulation in the bone at 60-75 min post injection (FIG. 15). The level of accumulation or retention of [$^{18}$F] FPTDG-derived radioactivity in the lungs, muscles, and other organs and tissues was extremely low. Also, there was no measurable levels of [$^{18}$F]FPTDG-derived radioactivity in the brain, which means that [$^{18}$F]FPTDG does not cross the blood-brain barrier (BBB).

Radiation Dose-Limiting Organs and Tissues

Based on these dynamic PET/CT imaging results, the primary radiation dose-limiting organs are liver and gall bladder, and, to a much lesser extent, upper intestine. Organs and tissues immediately adjacent to the liver will be exposed to higher doses or radioactivity as well, but not critical.

Pharmacologic Toxicity

No pharmacologic toxicity can be anticipated or actually observed using radiotracer doses of [$^{18}$F]FPTDG.

Potential diagnostic utility of [$^{18}$F]FPTDG

Radioactivity levels derived from [$^{18}$F]FPTDG in all major organs and tissues, including the liver and gall bladder after 75 min post intravenous administration are very low. Therefore, imaging abnormalities associated with upregulation of Galectin-1 and/or Galectin-3 levels as part of pathophysiologic or pathomorphologic phenomena (i.e., fibrosis, cancers, inflammatory and autoimmune diseases), should be possible in different organs and tissues, including: the head and neck (i.e., oropharyngeal structures, salivary glands, thyroid, parathyroid, etc.), lungs (including larynx, bronchial tree and lung parenchyma), heart and major vessels, esophagus, stomach, liver, pancreas, kidney, spleen, lower intestines, prostate (or uterus), gonads (i.e., testes, ovaries), muscles, bones, cartilage, skin, vasculature and lymph nodes.

Radiation dosimetry estimates for human patients are summarized in Table V.

TABLE V

Estimated Organ doses for adult male
(mSv per 370 MBq dose or 10 mCi)

| Target Organ | Alpha | Beta | Photon | Total | EDE Cont. | ED Cont. |
|---|---|---|---|---|---|---|
| Adrenals | 0 | 1.70 | 3.33 | 5.03 | 0.00 | 0.03 |
| Brain | 0 | 1.70 | 2.22 | 3.92 | 0.00 | 0.02 |
| Breasts | 0 | 1.70 | 1.87 | 3.57 | 0.54 | 0.18 |
| Gallbladder Wall | 0 | 1.70 | 3.7 | 5.40 | 0.00 | 0.00 |
| LLI Wall | 0 | 9.25 | 5.06 | 14.30 | 0.86 | 1.72 |
| Small Intestine | 0 | 4.15 | 4.21 | 8.36 | 0.50 | 0.04 |
| Stomach Wall | 0 | 9.17 | 5.78 | 14.90 | 0.90 | 1.79 |
| ULI Wall | 0 | 1.70 | 4.02 | 5.71 | 0.00 | 0.03 |
| Heart Wall | 0 | 1.72 | 2.76 | 4.48 | 0.00 | 0.00 |
| Kidneys | 0 | 1.70 | 3.24 | 4.94 | 0.00 | 0.02 |
| Liver | 0 | 1.30 | 2.79 | 4.08 | 0.00 | 0.20 |
| Lungs | 0 | 0.03 | 2.26 | 2.29 | 0.28 | 0.28 |
| Muscle | 0 | 1.70 | 2.68 | 4.38 | 0.00 | 0.02 |
| Ovaries | 0 | 1.70 | 4.32 | 6.02 | 1.50 | 1.20 |
| Pancreas | 0 | 1.70 | 4.2 | 5.90 | 0.35 | 0.03 |
| Red Marrow | 0 | 1.21 | 3.03 | 4.24 | 0.51 | 0.51 |
| Osteogenic Cells | 0 | 3.64 | 3.17 | 6.82 | 0.21 | 0.07 |
| Skin | 0 | 1.70 | 1.76 | 3.46 | 0.00 | 0.03 |
| Spleen | 0 | 1.70 | 3.52 | 5.22 | 0.00 | 0.03 |
| Testes | 0 | 1.70 | 2.67 | 4.37 | 0.00 | 0.00 |
| Thymus | 0 | 1.70 | 2.63 | 4.33 | 0.00 | 0.02 |
| Thyroid | 0 | 1.70 | 2.78 | 4.48 | 0.13 | 0.22 |
| Urinary Bladder Wall | 0 | 1.70 | 3.63 | 5.33 | 0.00 | 0.27 |
| Uterus | 0 | 1.70 | 4.06 | 5.76 | 0.35 | 0.03 |
| Total Body | 0 | 1.79 | 2.67 | 4.46 | 0.00 | 0.00 |

Effective Dose Equivalent 6.12
Effective Dose 6.74

The primary radiation dose-limiting organs were the liver and gallbladder. No acute pharmacologic toxicity at radiotracer doses has been observed. The [$^{18}$F]FPTDG was primarily excreted via the hepatobiliary route, as evidenced by high levels of radioactivity in the liver during the early phase of clearance, followed by transit of radioactivity through the intestines. The renal clearance was insignificant, as evidenced by very low amounts of radioactivity present in the bladder; the radioactivity in the kidneys was localized predominantly to the renal cortex, with almost no radioactivity registered in the renal pelvis and ureters. No substantial uptake or retention of [$^{18}$F]FPTDG was observed in any other organs or tissues. The [$^{18}$F]FPTDG exhibited a rapid bi-exponential clearance from the blood (fast clearance half-time=0.5 min, slow clearance half-time=7.36 min). Minimal, but detectable defluorination was observed as evidenced by very low amounts of [$^{18}$F]-fluoride radioactivity accumulation in the bone. Based on the results of these studies, administration of 10 mCi of [$^{18}$F]FPTDG to human patients will be safe in terms of radiation dose to the whole body and/or individual organs. Higher or lower doses can also be used, considering circumstances.

Example 12

PET/CT imaging of 3-(3-[$^{18}$F]fluorophenyl triazolyl)-3-deoxy-3'-(3-fluorophenyl triazolyl)-3'-deoxy-1-thio-β-D-digalactopyranoside ([$^{18}$F]FPTDG) biodistribution kinetics in immune-deficient mice bearing an orthotopic human breast carcinoma xenograft (MCF10DCIS).

Radiosynthesis of [$^{18}$F]FPTDG

The [$^{18}$F]FPTDG has been radiosynthesized as described above for PET/CT imaging in rats.

Orthotopic Human Breast Carcinoma Xenograft Model in Mice

A single (unilateral) orthotopic breast carcinoma xenograft was established in immunedeficient nu/nu mice by injection of human breast ductal carcinoma in situ cells (MCF10DCIS) in Matrigel into one of the upper mammary fat pad. After about 2 weeks of growth, the tumors reached about 8±2 mm in diameter, at which time, the mice were included into PET/CT imaging studies with [$^{18}$F]FPTDG.

PET/CT Imaging

Tumor-bearing mice (~20-25 g) were anesthetized using inhalation of 2% isoflurane in oxygen, and their body temperature maintained at 38° C. by a heating pad with a feedback temperature control. The mice were positioned inside the microPET R4 (Siemens) with the field of view covering the whole body and injected intravenously with ~150 µCi of [$^{18}$F]FPTDG. Dynamic PET images were acquired in list-mode and reconstructed using OSEM algorithm at multiple time frames post radiotracer administration (0-2, 2-4, 4-6, 6-8, 8-10, 10-20, 20-30, 30-40, 40-50, 50-60 min). Thereafter, while still fixed to the positioning bed, the mice were moved with the bed into the gantry of INVEON SPECT/CT (Siemens), and CT images were acquired over the whole body area for attenuation correction of PET images and for production of PET/CT images. PET/CT fusion images were generated and analyzed in a similar manner as when studying rats.

Pharmacokinetics and Biodistribution of [$^{18}$SF]FPTDG in Tumor-Bearing Mice

Figure 20A:
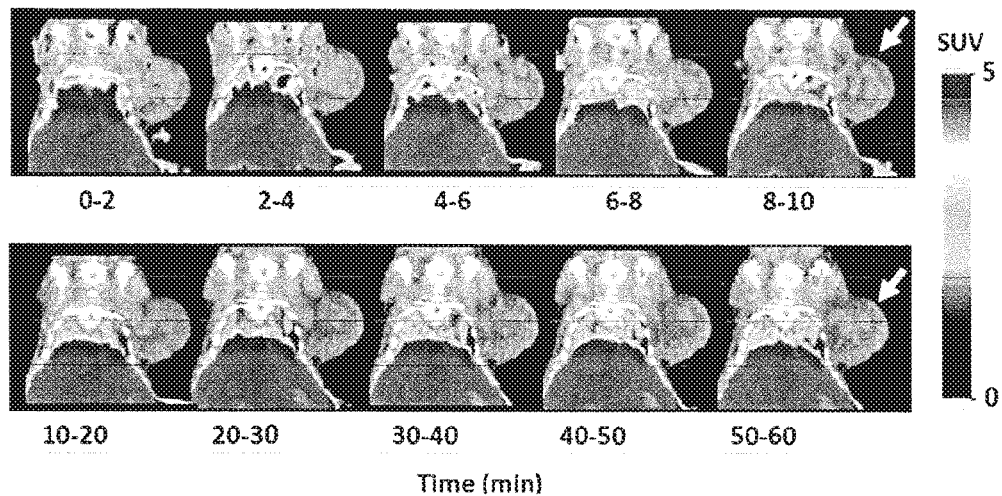
FIG. 20A shows images of dynamic PET/CT images of $^{18}$F-FPTDG accumulation in MCA10DCIS breast tumor xenografts in nude mice in which the arrow indicates the location of subcutaneous xenograft of MCF10DCIS tumor.

FIG. 20 shows PET/CT imaging of 3-(3-[$^{18}$F]fluorophenyl triazolyl)-3-deoxy-3'-(3-fluorophenyl triazolyl)-3'-deoxy-1-thio-βD-digalactopyranoside ([$^{18}$F]FPTDG) biodistribution kinetics in immune-deficient mice bearing an orthotopic human breast carcinoma xenograft (MCF10DCIS).

Figure 20B:
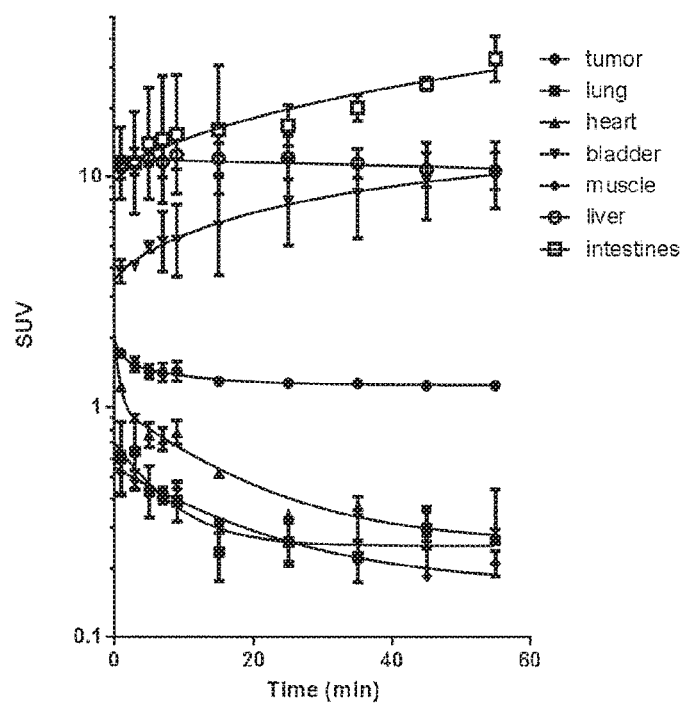
FIG. 20B is a graph showing time activity curves of $^{18}$F-FPTDG in different organs and tissues (SUV av±std err)
Figure 20C:
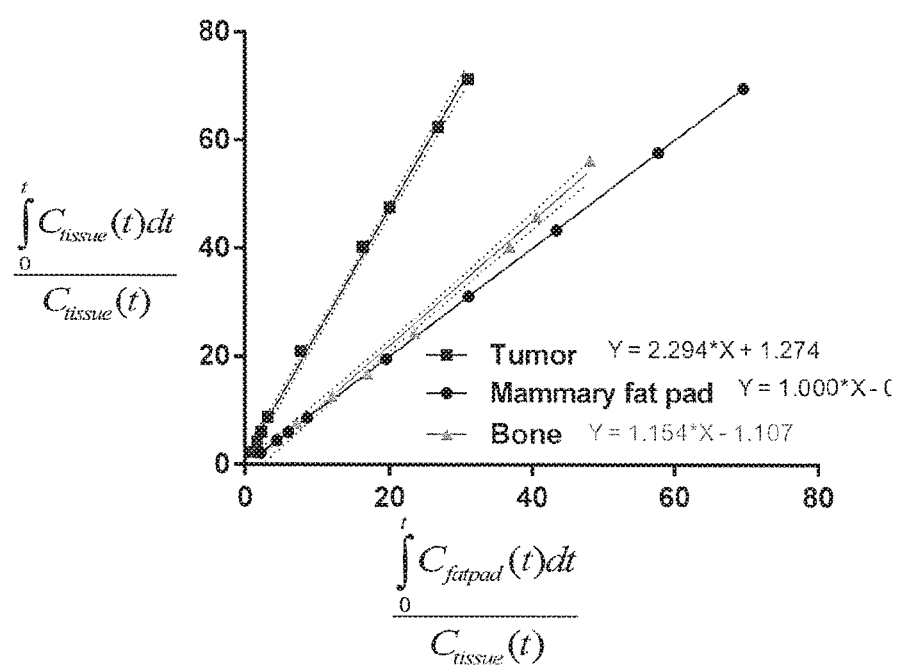
FIG. 20C is a graph showing results of Logan graphical analysis of $^{18}$F-FPTDG accumulation in MCA10DCIS breast tumor using muscle as a reference tissue.

The [$^{18}$F]FPTDG exhibited a rapid bi-exponential clearance from the blood (fast clearance half-time ~0.5 min, slow clearance half-time ~10.5 min; FIG. 20B), which occurred predominantly via the hepatobiliary route of excretion, as evidenced by very high levels of radioactivity in the liver (FIG. 20A), increasing levels in duodenum and upper intestinal tract (with gradual progression of [$^{18}$F]FPTDG-derived radioactivity towards the large intestine by way of peristalsis). Liver and kidney clearance followed mono-exponential kinetics with half-times of ~120 min and 37 min, respectively.

Renal clearance was more active in mice, as compared with rats, as evidenced by higher amounts of radioactivity in the bladder (FIG. 20B). The magnitude of catabolism of [$^{18}$F]FPTDG was negligible, as evidenced by very low levels of [$^{18}$F]F2 accumulation in the bone at 60 min post injection (FIG. 20A). The level of accumulation or retention of [$^{18}$F]FPTDG-derived radioactivity in the lungs, muscles, and other organs and tissues was extremely low. Also, there was no measurable levels of [$^{18}$F]FPTDG-derived radioactivity in the brain, which means that [$^{18}$F]FPTDG does not cross the blood-brain barrier (BBB) in mice either. PET/CT imaging demonstrated increased accumulation and retention of [$^{18}$F]FPDTG in MCF10DCIS xenografts that represent a model of early stage malignant breast lesion, with higher levels of radiotracer retained at 60 min post injection in the central, presumably in hypoxic tumor regions (FIG. 20A), which is consistent with previous reports that hypoxia upregulates Gal-3 expression in breast tumors and other tumor types. There was a significant retention of [18F]FPDTG in MCF10DCIS xenografts with very little clearance from 20 to 60 min post i.v. injection (FIG. 20A), whereas no accumulation of radioactivity was detectable in normal mammary fat pads. Logan graphical analysis (FIG. 20C) demonstrated a 2-3-fold increased binding and accumulation of [$^{18}$F]FPDTG in early stage breast carcinomas MCF10DCIS, as compared to normal breast tissue and muscle. Concurrent administration of non-radiolabeled FPTDG (10 mg/kg i.v. in 200 µl saline) 15 min prior to i.v. injection of [$^{18}$F]FPDTG resulted in an almost complete (>90%) blockade of the radiotracer uptake and retention in DCIS lesion at 60 min post injection (FIG. 20B,C). These results demonstrate a use of [$^{18}$F]FPDTG PET/CT imaging for detection of early stage malignant breast lesions.

Galectin expression in malignant breast tumors versus benign lesions and normal breast tissue.

Figure 21A:
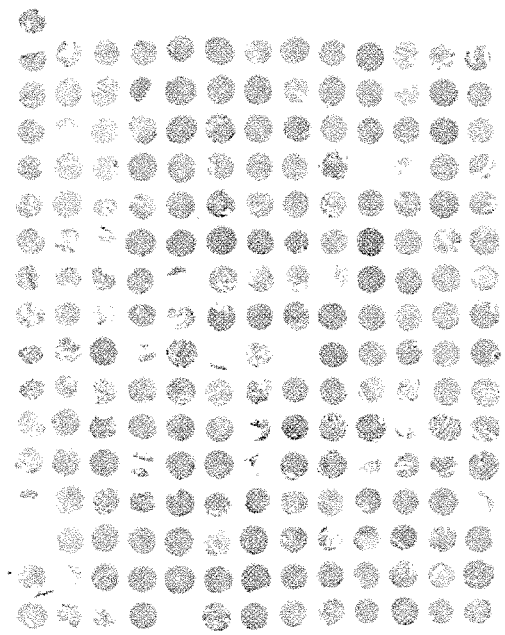
FIG. 21A is an image showing Gal-3 expression progression from normal breast tissue to benign and malignant lesions assessed by immunohistochemical staining of high density tissue array and shows that the level of Gal-3 expression is low-to non-detectable in normal breast tissue and minimally increased in benign lobular hyperplasia and fibroadenomatous epithelial hyperplasia. In contrast, Gal-3 expression is dramatically increased in DCIS and invasive ductal carcinomas.
Figure 21B:
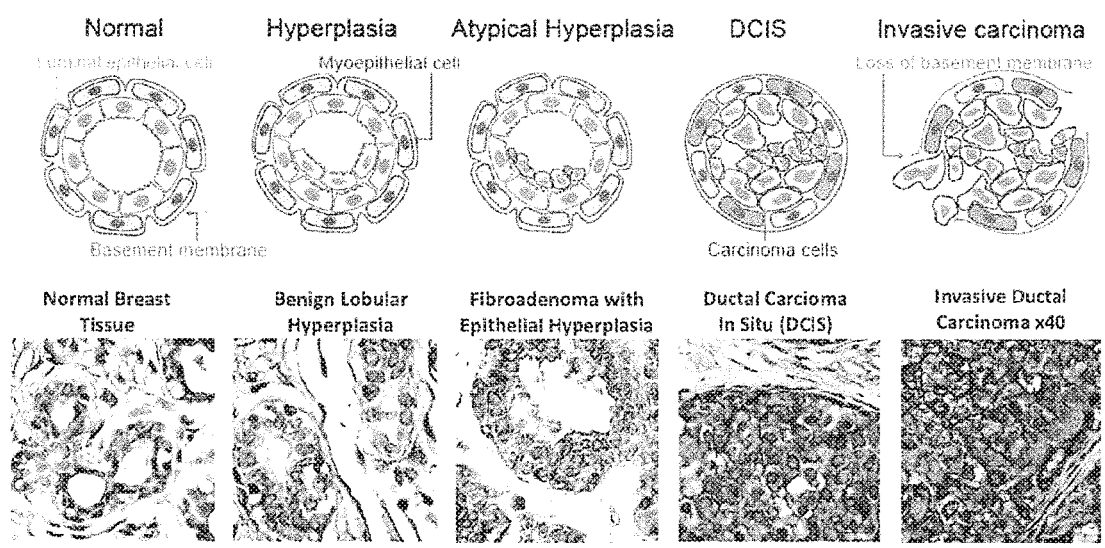
FIG. 21B shows diagrammatic images of progression stages of breast cancer and corresponding images of immunohistochemical staining for Gal-3 showing Gal-3 expression progression from normal breast tissue to benign and malignant lesions as assessed by immunohistochemical staining of high density tissues.
Figure 22:
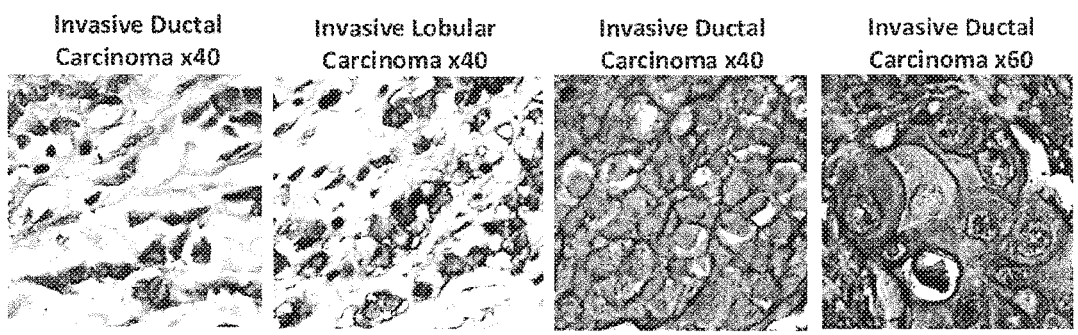
FIG. 22 is an image of immunohistochemical staining for Gal-3 showing high levels of Gal-3 expression in cell membranes and cell cytoplasm of invasive ductal and lobular breast carcinomas.

Gal-3 expression was assessed using immunohistochemical staining of tissue arrays representing breast carcinoma progression from normal to benign to malignant lesions (US Biomax, Rockville, Md.). These arrays included normal breast tissue (N=64), benign hyperplastic and adenomatous lesions (N=86), ductal carcinomas in situ (DCIS; N=248), early stage lobular carcinomas (N=62), and invasive, metastatic ductal (N=172) and lobular carcinomas (N=154). Gal-3 expression was found to be very low to non-detectable in normal breast tissue and very low in benign adenomatous and hyperplastic lesions as shown in FIGS. 21A and 21B. In contrast, there was a dramatic increase in Gal-3 expression in DCIS lesions (p<0.01), and, especially, in invasive ductal and lobular carcinomas, as compared to normal (p<0.001) and benign adenomatous/hyperplastic lesions (p<0.01) as shown in FIGS. 21A, 21B, and FIG. 22. Such IHC studies validate Gal-3 as sensitive and specific tissue biomarker for differential diagnosis of benign versus malignant breast lesions.

Items

Item 1. A composition, comprising: a labeled composition having the structural formula (I):

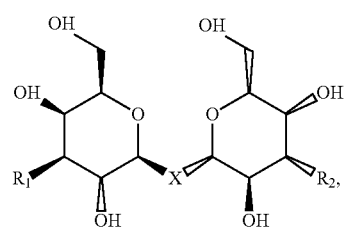

(I)

where $R_1$ is

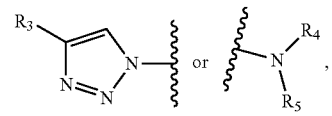

where $R_2$ is

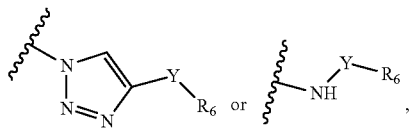

where $R_3$, $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, NCH$_3$, S or Se, where Y is a substituted or unsubstituted aromatic ring, and where $R_6$ is a radioactive or fluorescent label.

Item 2. The composition of item 1, where the labeled composition has the structural formula II where $R_3$ is selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, NCH$_3$, S or Se, where Y is a substituted or unsubstituted aromatic ring, and where $R_6$ is a radioactive or fluorescent label.

Item 3. The composition of item 1, where the labeled composition has the structural formula III, where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, NCH$_3$, S or Se, where Y is a substituted or unsubstituted aromatic ring, and where $R_6$ is a radioactive or fluorescent label.

Item 4. The composition of item 1, where the labeled composition has the structural formula IV, where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, NCH$_3$, S or Se, where Y is a substituted or unsubstituted aromatic ring, and where $R_6$ is a radioactive or fluorescent label.

Item 5. The composition of item 1, where the labeled composition has the structural formula (V):

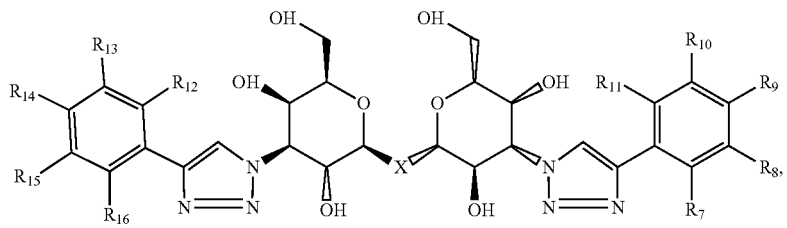

where X is C, Si, O, NH, NCH$_3$, S or Se, and where each of R$_7$, R$_8$, R$_9$, R$_{10}$, R$_{11}$, R$_{12}$, R$_{13}$, R$_{14}$, R$_{15}$ and R$_{16}$ is independently selected from the group consisting of: H, $^{18}$F, $^{76}$Br, $^{123}$I, $^{124}$I, $^{125}$I and $^{131}$I, wherein at least one of R$_7$, R$_8$, R$_9$, R$_{10}$, R$_{11}$, R$_{12}$, R$_{13}$, R$_{14}$, R$_{15}$ and R$_{16}$ is $^{18}$F, $^{76}$Br, $^{123}$I, $^{124}$I, $^{125}$I or $^{131}$I.

Item 6. The composition of item 5, where the labeled composition has the structural formula (V):

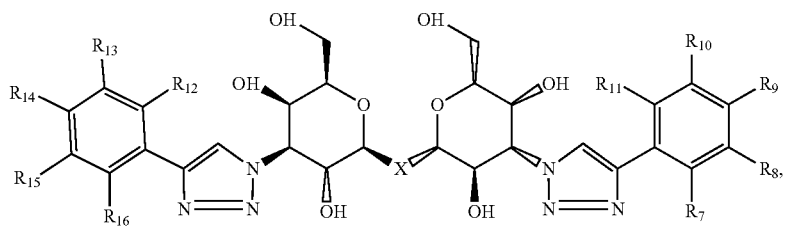

where X is C, Si, O, NH, NCH$_3$, S or Se, and where R$_7$, R$_8$, R$_9$, R$_{10}$, R$_{11}$R$_{12}$, R$_{13}$, R$_{14}$, R$_{15}$ are selected from the combinations 1-93 shown in Table I.

Item 7. The composition of item 6, wherein the labeled composition has the structural formula (VI):

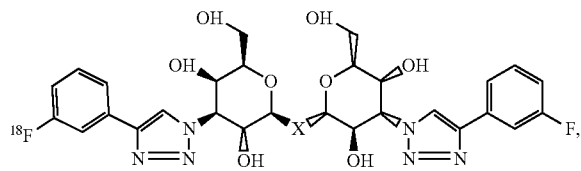

where X is C, Si, O, NH, NCH$_3$, S or Se.

Item 8. The composition of item 6, wherein the labeled composition has the structural formula (VII):

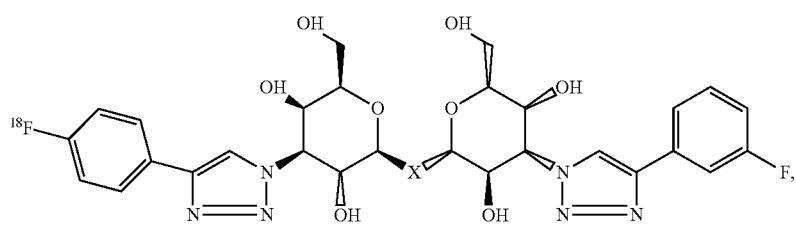

where X is C, Si, O, NH, NCH$_3$, S or Se.

Item 9. The composition of item 6, wherein the labeled composition has the structural formula (VIII):

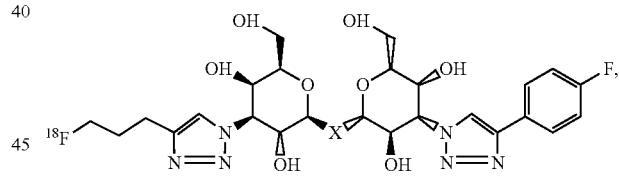

where X is C, Si, O, NH, NCH$_3$, S or Se.

Item 10. The composition of item 1, wherein the labeled composition has the structural formula (IX):

(IX)

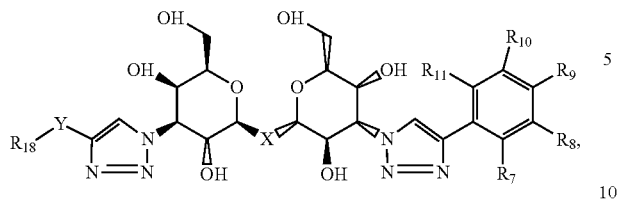

where each of $R_7$, $R_8$, $R_9$, $R_{10}$ and $R_{11}$ is independently selected from the group consisting of: H, F, Br, Cl, I, $NO_2$, $NMe_2$, $NEt_2$, $Sn(Me)_3$, $NH_2$, where X is C, Si, O, NH, $NCH_3$, S or Se, where Y is a substituted or unsubstituted aromatic ring, and where $R_{18}$ is a macrocyclic chelator complexed with a radionuclide.

Item 11. The composition of item 10, wherein the labeled composition has the structural formula (IX): where R7, R8, R9, R10 and R11 are H, F, Br, Cl, I, NO2, NMe2, NEt2, Sn(Me)3 or NH2 shown as combinations 94-357 in Table IT, where Y is a substituted or unsubstituted aromatic ring, and where $R_{18}$ is a macrocyclic chelator complexed with a radionuclide.

Item 12. The composition of any one of items 1 to 4, where the aromatic ring is phenyl, naphthyl, thienyl, furyl or pyrrolyl.

Item 13. The composition of any one of items 1 to 12, where X is S.

Item 14. A composition, comprising: a precursor composition having the structural formula (X):

(X)

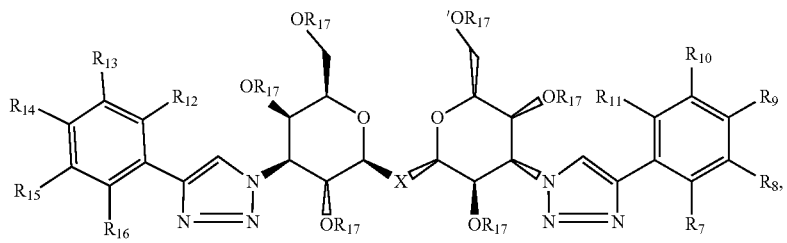

where each $R_{17}$ is a protecting group, where $R_7$, $R_8$, $R_9$, $R_{10}$, $R_{11}$, $R_{12}$, $R_{13}$, $R_{14}$, $R_{15}$ and $R_{16}$ are H, F, Br, I, $NO_2$, $(NMe_3)^+TfO^-$, $(NEt_3)^+TfO^-$, $Sn(Me)_3$ or $NH_2$ as shown in Table II as any one of combinations 94-357, where X is C, Si, O, NH, $NCH_3$, S or Se, wherein at least one of $R_7$, $R_8$, $R_9$, $R_{10}$, $R_{11}$, $R_{12}$, $R_{13}$, $R_{14}$, $R_{15}$ and $R_{16}$ is not H and with the proviso that $R_8$ and $R_{13}$ are not both fluorine.

Item 15. A composition, comprising: a precursor composition having the structural formula (XI):

(XI)

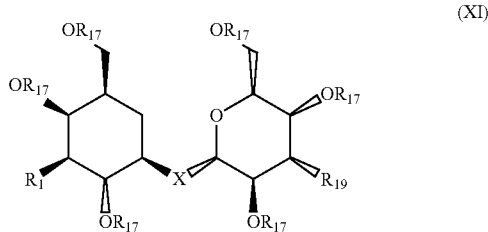

where $R_1$ is

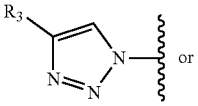 or

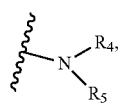

where $R_3$, $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where $R_{17}$ is a protective group and where $R_{19}$ is $N_3$ or $NH_2$.

Item 16. The composition of item 15, comprising: a precursor composition having the structural formula (XII):

(XII)

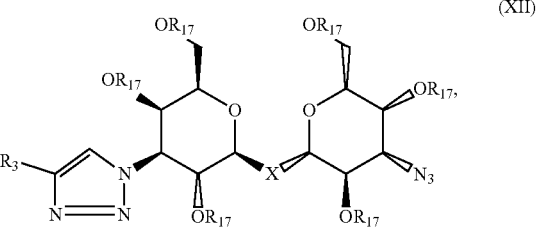

where $R_3$ is selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, and where $R_{17}$ is a protective group.

Item 17. The composition of item 15, comprising: a precursor composition having the structural formula (XIII):

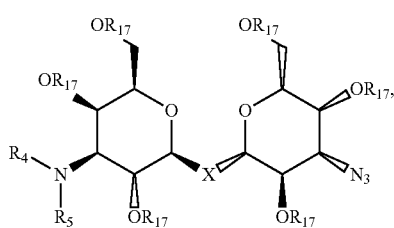

(XIII)

where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, and where $R_{17}$ is a protective group.

Item 18. The composition of item 15, comprising: a precursor composition having the structural formula (XIV):

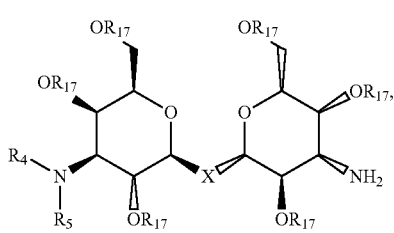

(XIV)

where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, and where $R_{17}$ is a protective group.

Item 19. The composition of item 15, comprising: a precursor composition having the structural formula (XV):

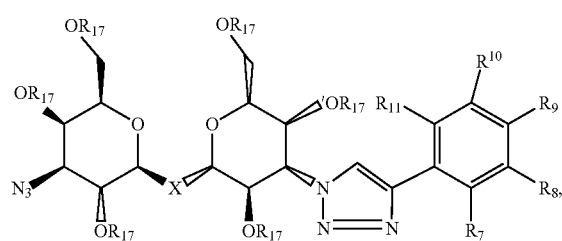

(XV)

where $R_7$, $R_8$, $R_9$, $R_{10}$ and $R_{11}$ are each independently selected from the group consisting of: H, F, Br, Cl, I, $NO_2$, $NMe_2$, $NEt_2$, $Sn(Me)_3$ and $NH_2$, where X is C, Si, O, NH, $NCH_3$, S or Se, and where $R_{17}$ is a protective group.

Item 20. The composition of item 19, where $R_7$, $R_8$, $R_9$, $R_{10}$ and $R_{11}$ are H, F, Br, Cl, I, $NO_2$, $NMe_2$, $NEt_2$, $Sn(Me)_3$ and $NH_2$ as shown in Table II as combinations 94-357.

Item 21. The composition of item 19, comprising: a precursor composition having the structural formula (XVI):

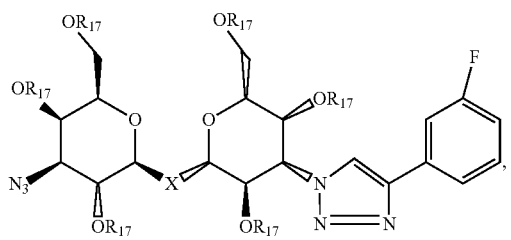

(XVI)

where X is C, Si, O, NH, $NCH_3$, S or Se, and where $R_{17}$ is a protective group.

Item 22. The composition of item 15, comprising: a precursor composition having the structural formula (XVII):

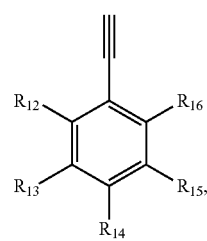

(XVII)

where X is C, Si, O, NH, $NCH_3$, S or Se, and where $R_{17}$ is a protective group.

Item 23. The composition of any one of items 15 to 18, where the aromatic ring is phenyl, naphthyl, thienyl, furyl or pyrrolyl.

Item 24. The composition of any one of items 14 to 23, where X is S.

Item 25. A composition, comprising: a precursor composition having the structural formula (XVIII):

(XVIII)

where $R_{12}$, $R_{13}$, R14, $R_{15}$ and $R_{16}$ are selected from the group consisting of: $^{18}F$, $^{76}Br$, $^{123}I$, $^{124}I$, $^{125}I$ or $^{131}I$, as shown in Table III as combinations 358-446.

Item 26. The composition of item 25, comprising: a precursor composition having the structural formula (XX):

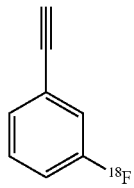

(XX)

Item 27. A composition, comprising: a precursor composition having the structural formula (XVIII):

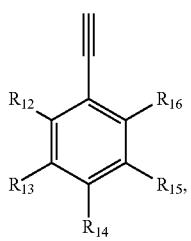

(XVIII)

where $R_{12}$, $R_{13}$, $R_{14}$, $R_{15}$ and $R_{16}$ are selected from the group consisting of: H, F, Br, Cl, I, $NO_2$, $(NMe_3)^+TfO^-$, $(NEt_3)^+$ $TfO^-$, $Sn(Me)_3$ and $NH_2$, as shown in Table IV as combinations 447-646.

Item 28. The composition of item 27, comprising: a precursor composition having the structural formula (XIX):

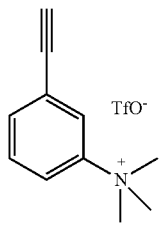

Item 29. A composition, comprising: a precursor composition having the structural formula (XXI):

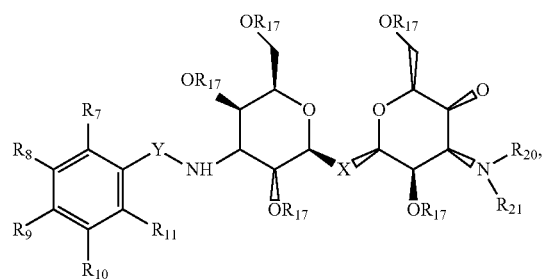

(XXI)

where each $R_{17}$ is a protecting group, where each $R_7$, $R_8$, $R_9$, $R_{10}$ and $R_{11}$ is independently selected from the group consisting of: H, OH, F, Br, Cl, I, $N(Alk)_2$, $Sn(Alk)_3$, $SnCl_2$, $NO_2$ and OTf, where X is C, Si, O, NH, $NCH_3$, S or Se, where Y is selected from the group consisting of $CH_2$, —C=, carbonyl, —C(NH)—, —NH(CO), —NH(CS), where $R_{20}$ and $R_{21}$ are each independently selected from the group consisting of: a substituted or unsubstituted alkyl, alkenyl, alkyne, alkoxy, acyl, carbamoyl, aryl, heteroaryl, and peptidyl, and where at least one of $R_7$, $R_8$, $R_9$, $R_{10}$, and $R_{11}$ is not H.

Item 30. The composition of item 29, where each $R_7$, $R_8$, $R_9$, $R_{10}$ and $R_{11}$ is independently selected from the group consisting of: H, $^{18}F$, $^{76}Br$, $^{123/124/125/131}I$, and $^{11}C$, where X is C, Si, O, NH, $NCH_3$, S or Se, where Y is selected from the group consisting of: CH2, —C=, carbonyl, —C(NH)—, —NH(CO), —NH(CS), where $R_1$ and $R_2$ are each independently selected from the group consisting of: a substituted or unsubstituted alkyl, alkenyl, alkyne, alkoxy, acyl, carbamoyl, aryl, heteroaryl, and peptidyl, and where at least one of $R_7$, $R_8$, $R_9$, $R_{10}$, and $R_{11}$ is not H.

Item 31. The composition of item 29 or 30, where X is S.

Item 32. A pharmaceutical composition comprising a labeled composition of any one of items 1 to 13 further comprising a pharmaceutically acceptable carrier.

Item 33. A method of detecting a galectin, comprising: contacting a galectin with a labeled composition according to any one of items 1 to 13 or 32 under conditions to form a complex of the labeled composition and the galectin; and detecting a signal of the labeled composition in the complex of the labeled composition and the galectin.

Item 34. The method of item 33, wherein the labeled composition comprises a radionuclide and wherein detecting the signal comprises obtaining a PET, SPECT or scintigraphic image.

Item 35. The method of item 33, wherein the labeled composition comprises a fluorophore and wherein detecting the signal comprises obtaining a fluorescence image.

Item 36. The method of any of items 33-35, wherein the galectin is in vitro.

Item 37. The method of any of items 33-35, wherein the galectin is in a subject.

Item 38. The method of item 37, wherein the subject has or is suspected of having cancer, heart failure, ventricular remodeling, an infection, an HIV infection, a pathological autoimmune condition and/or a pathological inflammatory condition.

Item 39. The method of item 38, wherein the cancer is breast cancer.

Item 40. The method of any of items 33-39, wherein the galectin is galectin-1 or galectin-3.

Item 41. A method of chemical synthesis of a labeled composition according to any of items 1 to 13 or 32, comprising chemical reaction of a precursor composition according to any of items 15 to 31.

Item 42. A method of aiding in diagnosis and/or treatment of a condition characterized by upregulation of one or more galectins in a subject in need thereof, comprising: contacting a galectin with a labeled composition according to any one of items 1 to 13 or 32 under conditions to form a complex of the labeled composition and the galectin; detecting a signal of the labeled composition in the complex of the labeled composition and the galectin; and comparing the signal to a control, thereby determining the level of the one or more galectins in the subject.

Item 43. The method of item 42, wherein the labeled composition comprises a radionuclide and wherein detecting the signal comprises obtaining a PET, SPECT or scintigraphic image.

Item 44. The method of item 42, wherein the labeled composition comprises a fluorophore and wherein detecting the signal comprises obtaining a fluorescence image.

Item 45. The method of any of items 42-44, wherein the one or more galectins are in a biological sample obtained from the subject.

Item 46. The method of any of items 42-44, wherein contacting a galectin with a labeled composition comprises administering the labeled composition to the subject.

Item 47. The method of any of items 42-46, wherein the subject has or is suspected of having cancer, heart failure, ventricular remodeling, an infection, an HIV infection, a pathological autoimmune condition and/or a pathological inflammatory condition.

Item 48. The method of any of items 42-47, wherein the subject has or is suspected of having breast cancer.

Item 49. The method of any of items 42-48, wherein the one or more galectins are selected from the group consisting of: galectin-1 and galectin-3.

Item 50. The method of any of items 42-49, wherein the control includes a level of the one or more galectins determined in the subject prior to administration of a treatment for the condition characterized by upregulation of one or more galectins.

Item 51. The method of any of items 42-50, wherein the control includes a reference level of the one or more galectins in a comparable subject or population of comparable subjects.

Item 52. A commercial package comprising a labeled composition or precursor composition described or shown herein, such as in items 1 to 13 or 32 or items 15 to 31.

Item 53. A labeled composition having the structural formula (VI):

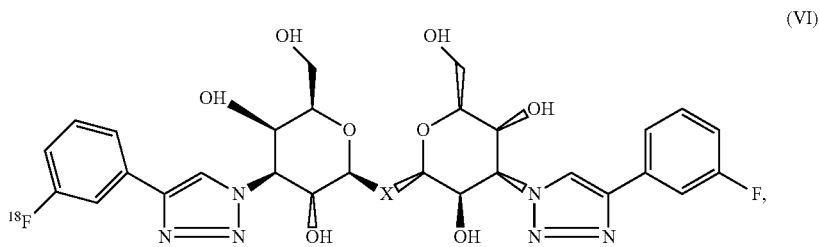

(VI)

where X is S.

Item 54. A labeled composition having the structural formula (VII):

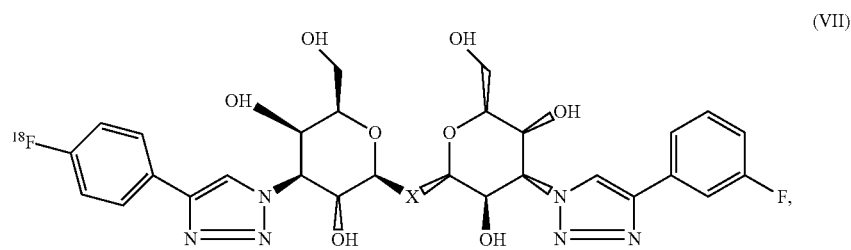

(VII)

where X is S.

Item 55. A labeled composition has the structural formula (VIII):

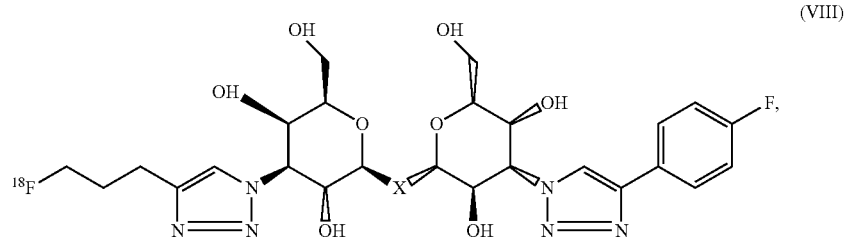

(VIII)

where X is S.

Item 56. A method of detecting a galectin, comprising: contacting a galectin with a labeled composition according to any one of items 53, 54, 55 or a combination of any two or more thereof under conditions to form a complex of the labeled composition and the galectin; and detecting a signal of the labeled composition in the complex of the labeled composition and the galectin.

Item 57. A method of detecting a galectin, comprising: administering a labeled composition according to any one of items 1 to 13 or 32 or a combination of any two or more thereof to a subject, forming a complex of the labeled composition and the galectin in the subject; and detecting a signal of the labeled composition in the complex of the labeled composition and the galectin in the subject.

Item 58. A method of detecting a galectin, comprising: administering a labeled composition according to any one of items 53, 54, 55 or a combination of any two or more thereof to a subject, forming a complex of the labeled composition and the galectin in the subject; and detecting a signal of the labeled composition in the complex of the labeled composition and the galectin in the subject.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A composition, comprising: a labeled compound having the structural formula (I):

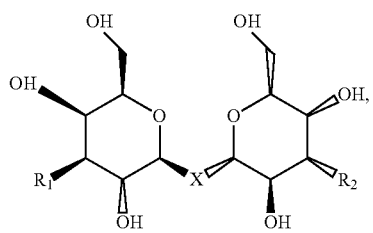

where $R_1$ is

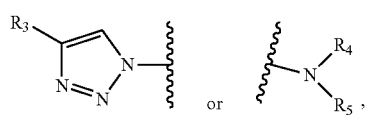

where $R_2$ is

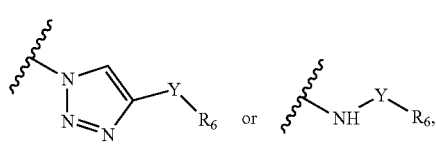

where $R_3$, $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label.

2. The composition of claim 1, where the labeled compound has the structural formula II

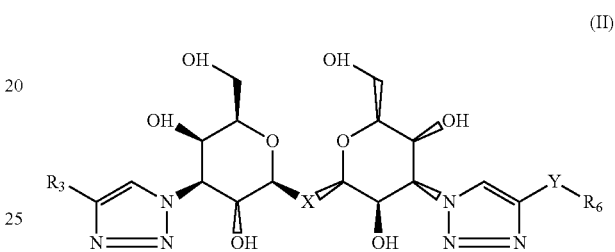

where $R_3$ is selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label.

3. The composition of claim 1, where the labeled compound has the structural formula III

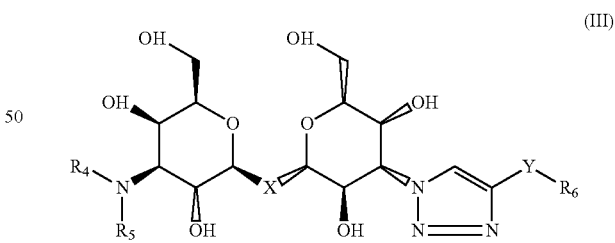

where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label.

4. The composition of claim 1, where the labeled compound has the structural formula IV

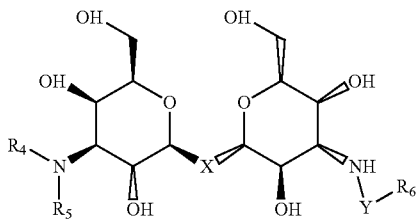
(IV)

where $R_4$ and $R_5$ are each independently selected from the group consisting of: a substituted or unsubstituted alkyl, alkenyl, alkyne or alkoxy group, a carbamoyl substituted with an alkyl, alkenyl, alkyne or alkoxy group, and a substituted or unsubstituted aromatic ring, where X is C, Si, O, NH, $NCH_3$, S or Se, where Y is a substituted or unsubstituted aromatic ring, and where $R_6$ is a radioactive or fluorescent label.

5. The composition of claim 1, where the labeled compound has the structural formula (V):

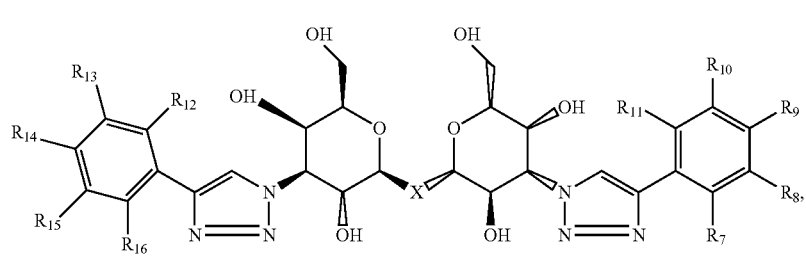
(V)

where each of $R_7$, $R_8$, $R_9$, $R_{10}$, $R_{11}$, $R_{12}$, $R_{13}$, $R_{14}$, $R_{15}$ and $R_{16}$ is independently selected from the group consisting of: H, $^{18}F$, $^{76}Br$, $^{123}I$, $^{124}I$, $^{125}I$ and $^{131}I$ wherein at least one of $R_7$, $R_8$, $R_9$, $R_{10}$, $R_{11}$, $R_{12}$, $R_{13}$, $R_{14}$, $R_{15}$ and $R_{16}$ is $^{18}F$, $^{76}Br$, $^{123}I$, $^{124}I$, $^{125}I$ or $^{131}I$.

6. The composition of claim 5, where the labeled compound has the structural formula (V):

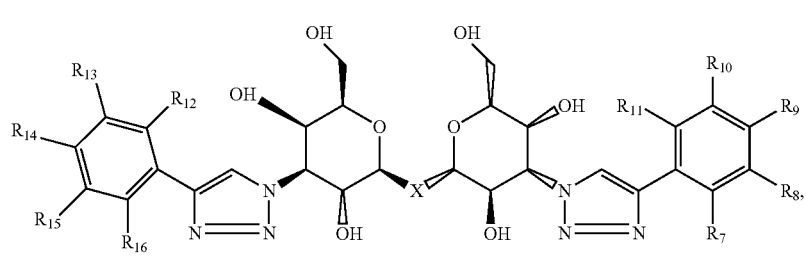
(V)

where $R_7$, $R_8$, $R_9$, $R_{10}$, $R_{11}$, $R_{12}$, $R_{13}$, $R_{14}$, $R_{15}$ are selected from the combinations 1-93 shown in Table I.

7. The composition of claim 6, wherein the labeled compound has the structural formula (VI):

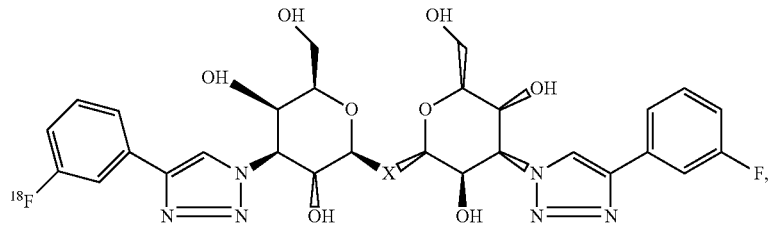

where X is C, Si, O, NH, $NCH_3$, S or Se.

8. The composition of claim 6, wherein the labeled compound has the structural formula (VII):

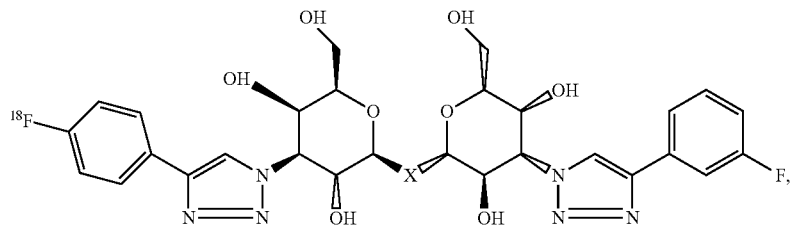

where X is C, Si, O, NH, NCH₃, S or Se.

9. The composition of claim 6, wherein the labeled compound has the structural formula (VIII):

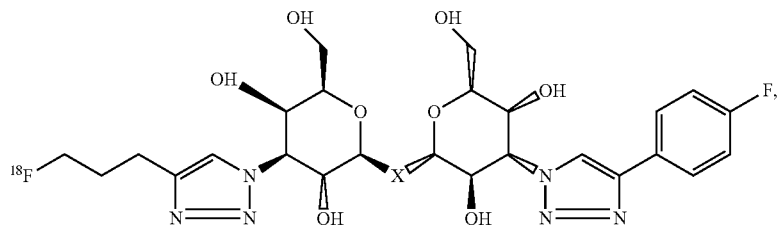

where X is C, Si, O, NH, NCH₃, S or Se.

10. The composition of claim 1, wherein the labeled compound has the structural formula (IX):

(IX)

where each of $R_7$, $R_8$, $R_9$, $R_{10}$ and $R_{11}$ is independently selected from the group consisting of: H, F, Br, Cl, I, $NO_2$, $NMe_2$, $NEt_2$, $Sn(Me)_3$, $NH_2$, where X is C, Si, O, NH, NCH₃, S or Se, where Y is a substituted or unsubstituted aromatic ring, and where $R_{18}$ is a macrocyclic chelator complexed with a radionuclide.

11. The composition of claim 10, wherein the labeled compound has the structural formula (IX): where $R_7$, $R_8$, $R_9$, $R_{10}$ and $R_{11}$ are H, F, Br, Cl, I, $NO_2$, $NMe_2$, $NEt_2$, $Sn(Me)_3$ or $NH_2$ shown as combinations 94-357 in Table II.

12. The composition of claim 1, where the aromatic ring is phenyl, naphthyl, thienyl, furyl or pyrrolyl.

13. The composition of claim 1, where X is S.

14. A method of detecting a galectin, comprising:
contacting a galectin with a labeled composition according to claim 1 under conditions to form a complex of the labeled composition and the galectin; and
detecting a signal of the labeled composition in the complex of the labeled composition and the galectin.

15. The method of claim 14, wherein the labeled composition comprises a radionuclide and wherein detecting the signal comprises obtaining a PET, SPECT or scintigraphic image or wherein the labeled composition comprises a fluorophore and wherein detecting the signal comprises obtaining a fluorescence image.

16. The method of claim 14, wherein the galectin is in vitro.

17. The method of claim 14, wherein the galectin is in a subject, wherein contacting the galectin with a labeled composition according to claim 1, comprises administering the labeled composition to the subject.

18. The method of claim 17, wherein the subject has or is suspected of having cancer, heart failure, ventricular remodeling, an infection, an HIV infection, a pathological autoimmune condition and/or a pathological inflammatory condition.

19. The method of claim 18, wherein the cancer is breast cancer.

20. The method of claim 14, wherein the galectin is galectin-1 or galectin-3.